United States Patent
Lloyd et al.

(10) Patent No.: US 8,993,557 B2
(45) Date of Patent: Mar. 31, 2015

(54) PYRIDINEDIONE CARBOXAMIDE INHIBITORS OF ENDOTHELIAL LIPASE

(71) Applicant: Bristol-Myers Squibb Company, Princeton, NJ (US)

(72) Inventors: John Lloyd, Yardley, PA (US); Jennifer X. Qiao, Princeton, NJ (US); Heather Finlay, Skillman, NJ (US); James Neels, Newtown, PA (US); Zulan Pi, Pennington, NJ (US); Carol Hui Hu, New Hope, PA (US); Tammy C. Wang, Lawrenceville, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 14/347,683

(22) PCT Filed: Sep. 26, 2012

(86) PCT No.: PCT/US2012/057192
§ 371 (c)(1),
(2) Date: Mar. 27, 2014

(87) PCT Pub. No.: WO2013/049104
PCT Pub. Date: Apr. 4, 2013

(65) Prior Publication Data
US 2014/0235608 A1    Aug. 21, 2014

Related U.S. Application Data

(60) Provisional application No. 61/541,146, filed on Sep. 30, 2011.

(51) Int. Cl.
| A61K 31/00 | (2006.01) |
|---|---|
| C07D 213/62 | (2006.01) |
| C07D 213/81 | (2006.01) |
| C07D 213/79 | (2006.01) |
| C07D 401/12 | (2006.01) |
| C07D 413/12 | (2006.01) |
| C07D 417/12 | (2006.01) |

(52) U.S. Cl.
CPC ............ *C07D 213/81* (2013.01); *C07D 213/79* (2013.01); *C07D 401/12* (2013.01); *C07D 413/12* (2013.01); *C07D 417/12* (2013.01)
USPC ....................................... 514/210.2; 546/298

(58) Field of Classification Search
None
See application file for complete search history.

(56) References Cited

U.S. PATENT DOCUMENTS

| 7,217,727 B2 | 5/2007 | Eacho et al. |
| 7,595,403 B2 | 9/2009 | Eacho et al. |
| 2005/0261322 A1 | 11/2005 | Naidu et al. |
| 2006/0211755 A1 | 9/2006 | Eacho et al. |
| 2007/0155744 A1 | 7/2007 | Jones et al. |
| 2008/0287448 A1 | 11/2008 | Zoller et al. |
| 2009/0054478 A1 | 2/2009 | Zoller et al. |
| 2009/0076068 A1 | 3/2009 | Zoller et al. |

FOREIGN PATENT DOCUMENTS

| GB | 2 345 058 | 6/2000 |
| WO | WO99/32611 A1 | 7/1999 |
| WO | WO03/042206 A1 | 5/2003 |
| WO | WO2004/093872 A1 | 11/2004 |
| WO | WO2004/094393 A1 | 11/2004 |
| WO | WO2004/094394 A1 | 11/2004 |
| WO | WO2005/074513 A2 | 8/2005 |
| WO | WO 2005074513 A2 * | 8/2005 |
| WO | WO2007/042178 A1 | 4/2007 |
| WO | WO2007/110215 A1 | 10/2007 |
| WO | WO2007/110216 A1 | 10/2007 |
| WO | WO2008/012352 A2 | 10/2008 |
| WO | WO2009/123164 A1 | 10/2009 |
| WO | WO2009/133834 A1 | 11/2009 |

OTHER PUBLICATIONS

Bevilacqua, M. et al., "Selectins", J. Clinical Invest., vol. 91, pp. 379-387 (1993).
deLemos, A. et al., "Identification of Genetic Variants in Endothelial Lipase in Persons With Elevated High-Density Lipoprotein Cholesterol", Circulation, vol. 106, pp. 1321-1326 (2002).
Folkman, J. et al., "Angiogenic Factors", Science, vol. 235, pp. 442-447 (1987).
Folkman, J. et al., "Angiogenesis" *Minireview*. The J. of Biological Chemistry, vol. 267(16) pp. 10931-10934 (1992).
Gordon, D.J. et al., "High-Density Lipoprotein—The Clinical Implications of Recent studies", New England J. of Medicine, vol. 321(19), pp. 1311-1316 (1989).
Gordon, D.J. et al., "High-Density Lipoprotein Cholesterol and Cardiovascular Disease", Circulation, vol. 79, pp. 8-15 (1989).
Hirata, K. et al., "Cloning of a Unique Lipase from Endothelial Cells Extends the Lipase Gene Family", The J. of Biological Chemistry, vol. 274(20), pp. 14170-14175 (1999).
Janssens, S.P. et al., "Cloning and Expression of a cDNA Encoding Human Endothelium-derived Relaxing Factor/Nitric Oxide Synthase", The J. of Biological Chemistry, vol. 267(21), pp. 14519-14522 (1992).

(Continued)

*Primary Examiner* — Heidi Reese
(74) *Attorney, Agent, or Firm* — Jing G. Sun

(57) ABSTRACT

The present invention provides compounds of Formula (I): as defined in the specification and compositions comprising any of such novel compounds. These compounds are endothelial lipase inhibitors which may be used as medicaments.

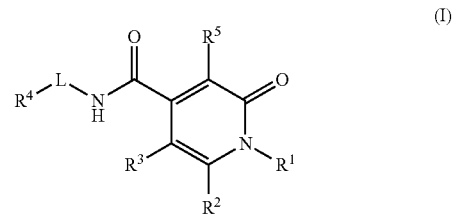

14 Claims, No Drawings

(56) References Cited

OTHER PUBLICATIONS

Jaye, M. et al., "A novel endothelial-derived lipase that modulates HDL metabolism", Nature Genetics, vol. 21, pp. 424-428 (1999).

Jin, W. et al., "Lipases and HDL metabolism" Trends in Endocrinology & Metabolism, vol. 13(4), pp. 174-178 (2002).

Lamas, S. et al., "Endothelial nitric oxide synthase: Molecular cloning and characterization of a distinct constitutive enzyme isoform", PNAS, vol. 89, pp. 6348-6352 (1992).

Lüscher, T.F. et al., "Endothelium-Derived Contracting Factors", Hypertension, vol. 19, pp. 117-130 (1992).

McCoy, M.G. et al., "Characterization of the lipolytic activity of endothelial lipase", Journal of Lipid Research, vol. 43, pp. 921-929 (2002).

Romanovski, V. et al., "Potential Agents for Removal of Actinides from Waste Solutions", Spectrum 96 International Conference on Nuclear and Hazardous Waste Management Conference Proceedings, vol. 3, pp. 2330-2334 (1996).

Ross, R., "The pathogenesis of atherosclerosis: a perspective for the 1990s" Nature, vol. 362(80), pp. 801-809 (1993).

Strauss, J.G. et al., "Endothelial cell-derived lipase mediates uptake and binding of high-density lipoprotein (HDL) particles and the selective uptake of HDL-associated cholesterol esters independent of its enzymic activity", Biochem. J., vol. 368, pp. 69-79 (2002).

Veeck, A. et al., "Hydroxypyridinone Extraction Agents for Pu(IV)", Solvent Extraction and Ion Exchange, vol. 22(6), pp. 1037-1068 (2004).

Williams, T.J. et al., "Adhesion Molecules Involved in the Microvascular Inflammatory Response", Am Rev. Respir. Disease, vol. 146, pp. S45-S50 (1992).

Wong, H. et al., "The lipase gene family", Journal of Lipid Research, vol. 43, pp. 993-999 (2002).

Yanagisawa, M. et al., "A novel potent vasoconstrictor peptide produced by vascular endothelial cells", Nature, vol. 332, pp. 411-415 (1988).

\* cited by examiner

PYRIDINEDIONE CARBOXAMIDE INHIBITORS OF ENDOTHELIAL LIPASE

CROSS-REFERENCE TO RELATED APPLICATIONS

The present application is a 371 application of PCT/US2012/057192 filed Sep. 26, 2012, which claims priority benefit of U.S. provisional application Ser. No. 61/541,146, filed Sep. 30, 2011; each of which is fully incorporated by reference herein.

FIELD OF THE INVENTION

The present invention provides novel pyridinedione carboxamide compounds and analogues, which are endothelial lipase (EL) inhibitors, compositions containing them, and methods of using them, for example, for the treatment and/or prophylaxis of dyslipidemias and the sequelae thereof.

BACKGROUND OF THE INVENTION

Cardiovascular disease is a major health risk throughout the industrialized world. Atherosclerosis, the most prevalent of cardiovascular diseases, is the principal cause of heart attack, and stroke, and thereby the principal cause of death in the United States.

Atherosclerosis is a complex disease involving many cell types and molecular factors (for a detailed review, see Ross, *Nature*, 362(80):1-809 (1993)). Results from epidemiologic studies have clearly established an inverse relationship between levels of high density lipoprotein (HDL), which transports endogenous cholesterol from tissues to the liver as well as mediating selective cholesteryl ester delivery to steroidogenic tissues, and the risk for atherosclerosis (Gordon et al., *N. Engl. J. Med.*, 321:1311-1316 (1989)).

The metabolism of HDL is influenced by several members of the triacylglycerol (TG) lipase family of proteins, which hydrolyze triglycerides, phospholipids, and cholesteryl esters, generating fatty acids to facilitate intestinal absorption, energy production, or storage. Of the TG lipases, lipoprotein lipase (LPL) influences the metabolism of HDL cholesterol by hydrolyzing triglycerides in triglyceride-rich lipoproteins, resulting in the transfer of lipids and apolipoproteins to HDL and is responsible for hydrolyzing chylomicron and very low density lipoprotein (VLDL) in muscle and adipose tissues. Hepatic lipase (HL) hydrolyzes HDL triglyceride and phospholipids, generating smaller, lipid-depleted HDL particles, and plays a role in the uptake of HDL cholesterol (Jin et al., *Trends Endocrinol. Metab.*, 13:174-178 (2002); Wong et al., *J. Lipid Res.*, 43:993-999 (2002)). Endothelial lipase (also known as EDL, EL, LIPG, endothelial-derived lipase, and endothelial cell-derived lipase) is synthesized in endothelial cells, a characteristic that distinguishes it from the other members of the family.

Recombinant endothelial lipase protein has substantial phospholipase activity but has been reported to have less hydrolytic activity toward triglyceride lipids (Hirata et al., *J. Biol. Chem.*, 274:14170-14175 (1999); Jaye et al., *Nat. Genet.*, 21:424-428 (1999)). However, endothelial lipase does exhibit triglyceride lipase activity ex vivo in addition to its HDL phospholipase activity, and endothelial lipase was found to hydrolyze HDL more efficiently than other lipoproteins (McCoy et al., *J. Lipid Res.*, 43:921-929 (2002)). Overexpression of the human endothelial lipase gene in the livers of mice markedly reduces plasma concentrations of HDL cholesterol and its major protein apolipoprotein A-I (apoA-I) (Jaye et al., *Nat. Genet.*, 21:424-428 (1999)).

Various types of compounds have been reported to modulate the expression of endothelial lipase, for example, 3-oxo-1,3-dihydro-indazole-2-carboxamides (WO 2004/093872, US 2006/0211755A1), 3-oxo-3-H-benzo[d]isoxazole-2-carboxamides (WO 2004/094393, U.S. Pat. No. 7,217,727), and benzisothiazol-3-one-2-carboxamides (WO 2004/094394, U.S. Pat. No. 7,595,403) by Eli Lilly & Co.; diacylindazole derivatives (WO 2007/042178, US 2008/0287448A1) and imidazopyridin-2-one derivatives (WO 2007/110215, US 2009/0076068A1), and azolopyridin-3-one derivatives (WO 2007/110216, US 2009/0054478A1) by Sanofi-Aventis; heterocyclic derivatives (WO 2009/123164) and keto-amide derivatives (WO 2009/133834) by Shionogi & Co., Ltd. However, because endothelial lipase is a relatively new member in the lipase gene family, a full understanding of the potential of endothelial lipase inhibitors to human health, as well as the inhibitors of other lipases in general, requires more studies.

Thus, there is a clear need for new types of compounds capable of inhibiting the activity of lipases, particularly endothelial lipase, that would constitute effective treatments to the diseases or disorders associated with the activity of such lipases.

SUMMARY OF THE INVENTION

The present disclosure provides novel pyridinedione carboxamide compounds and their analogues, including stereoisomers, tautomers, pharmaceutically acceptable salts, or solvates thereof, which are useful as EL inhibitors.

The present invention also provides processes and intermediates for making the compounds of the present invention.

The present invention also provides pharmaceutical compositions comprising a pharmaceutically acceptable carrier and at least one of the compounds of the present invention or stereoisomers, tautomers, pharmaceutically acceptable salts, or solvates thereof.

The compounds of the invention may be used in the treatment and/or prophylaxis of dyslipidemias and the sequelae thereof.

The compounds of the invention may be used in therapy.

The compounds of the invention may be used for the manufacture of a medicament for the treatment and/or prophylaxis of dyslipidemias and the sequelae thereof.

The compounds of the invention can be used alone, in combination with other compounds of the present invention, or in combination with one or more, preferably one to two, other agent(s).

Other features and advantages of the invention will be apparent from the following detailed description and claims.

DETAILED DESCRIPTION OF THE INVENTION

I. Compounds of the Invention

In a first aspect, the present invention provides, inter alia, a compound of Formula (I):

$$\text{(I)}$$

or a stereoisomer, a tautomer, a pharmaceutically acceptable salt, or a solvate thereof, wherein:

$R^1$ is selected from the group consisting of: H, $C_{1-6}$ alkyl substituted with 0-3 $R^a$, $C_{2-6}$ alkenyl substituted with 0-3 $R^a$, and $-(CH_2)_n-W-(CH_2)_m-R^{1a}$;

W is selected from the group consisting of: a bond, NH, O, S, N($C_{1-4}$ alkyl), CO, CONH, CON($C_{1-4}$ alkyl), NHCO, $SO_2$, $NHSO_2$, $SO_2NH$, $NHCO_2$, and $CHR^f$;

$R^{1a}$ is selected from the group consisting of: $C_{3-10}$ carbocycle and a 5- to 10-membered heterocycle comprising: carbon atoms and 1-4 heteroatoms selected from N, $NR^e$, O, and $S(O)_p$; and wherein said carbocycle and heterocycle are substituted with 0-3 $R^c$;

$R^2$ and $R^3$ are, independently at each occurrence, selected from the group consisting of: H, halogen, $CF_3$, $OCF_3$, $C_{1-6}$ alkyl substituted with 0-3 $R^a$, $C_{2-6}$ alkenyl substituted with 0-3 $R^a$, —$CO_2(C_{1-4}$ alkyl), —$SO_2$(phenyl), —$(CH_2)_n$—($C_{3-6}$ cycloalkyl substituted with 0-3 $R^c$), —$(CH_2)_n$-(phenyl substituted with 0-3 $R^b$), —$(CH_2)_n$-(naphthyl substituted with 0-3 $R^b$), and —$(CH_2)_n$-(5- to 10 membered heterocycle comprising: carbon atoms and 1-4 heteroatoms selected from N, $NR^e$, O, and $S(O)_p$), wherein said heterocycle is substituted with 0-3 $R^c$;

$R^4$ is selected from the group consisting of: $C_{3-10}$ carbocycle and a 5- to 10-membered heterocycle comprising: carbon atoms and 1-4 heteroatoms selected from N, $NR^e$, O, and $S(O)_p$; wherein said carbocycle and heterocycle are substituted with 0-3 $R^d$;

$R^5$ is selected from the group consisting of: $OR^6$, CN, and $NR^7R^8$;

$R^6$ is selected from the group consisting of: H and $C_{1-6}$ alkyl substituted with 0-1 $CO_2H$;

$R^7$ is selected from the group consisting of: H, $C_{1-6}$ alkyl substituted with 0-1 $R^a$, —$(CH_2)_n$-(phenyl substituted with 0-3 $R^b$), and —$(CH_2)_n$-(5- to 6-membered heterocycle comprising: carbon atoms and 1-4 heteroatoms selected from N, $NR^e$, O, and $S(O)_p$); and wherein said heterocycle is substituted with 0-3 $R^c$;

$R^8$ is selected from the group consisting of: H and $C_{1-6}$ alkyl;

alternatively, $NR^7R^8$ is a 5- to 6-membered heterocycle comprising: carbon atoms and 1-4 heteroatoms selected from N, $NR^e$, O, and $S(O)_p$;

L is $X_1$—Y—$X_2$;

$X_1$, and $X_2$ are, independently at each occurrence, selected from the group consisting of: a bond, a hydrocarbon linker and a hydrocarbon-heteroatom linker; wherein said hydrocarbon linker and hydrocarbon-heteroatom linker may be substituted with 0-2 $R^g$; said hydrocarbon linker has one to five carbon atoms and may be saturated or unsaturated; and said hydrocarbon-heteroatom linker may be saturated or unsaturated and has zero to four carbon atoms and one group selected from O, —CO—, S, —SO—, —$SO_2$—, NH, and N($C_{1-4}$ alkyl);

Y is selected from the group consisting of: $C_{3-10}$ carbocycle and a 4- to 10 membered heterocycle comprising: carbon atoms and 1-4 heteroatoms selected from N, $NR^e$, O, and $S(O)_p$; wherein each said carbocycle and heterocycle may be optionally substituted with one, two or three substituents independently selected from: halogen, OH, $C_{1-4}$ alkyl, $C_{1-4}$ haloalkyl, and $C_{1-4}$ alkyoxy;

alternatively, $R^4$-L- is

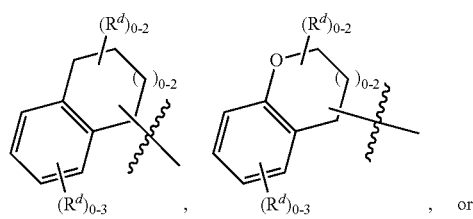, 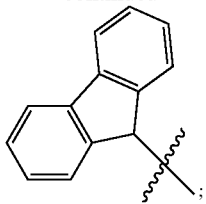

$R^a$ is, independently at each occurrence, selected from the group consisting of: halogen, OH, $C_{1-4}$ alkyl, $C_{1-4}$ alkoxy, $C_{1-4}$ haloalkyl, $C_{1-4}$ haloalkoxy, $CF_3$, $OCF_3$, CN, $NH_2$, $NO_2$, NH($C_{1-4}$ alkyl), N($C_{1-4}$ alkyl)$_2$, $CO_2H$, $CO_2(C_{1-4}$ alkyl), NHCO($C_{1-4}$ alkyl substituted with 0-1 $NH_2$), N($C_{1-4}$ alkyl) CO($C_{1-4}$ alkyl), $NHCO_2(C_{1-4}$ alkyl), $CONHSO_2(C_{1-4}$ alkyl), $SO_2(C_{1-4}$ alkyl), $CONH_2$, CONH($C_{1-4}$ alkyl), $NHSO_2(C_{1-4}$ alkyl), N($C_{1-4}$ alkyl)$SO_2(C_{1-4}$ alkyl), and phenoxy;

$R^b$ is, independently at each occurrence, selected from the group consisting of: halogen, OH, $C_{1-4}$ alkyl, $C_{1-4}$ alkoxy, $C_{1-4}$ haloalkyl, $C_{1-4}$ haloalkoxy, $CF_3$, $OCF_3$, $OCF_2CHF_2$, $OCH_2CF_3$, CN, $NH_2$, $NO_2$, NH($C_{1-4}$ alkyl), N($C_{1-4}$ alkyl)$_2$, $CO_2H$, $CO_2(C_{1-4}$ alkyl), $CONH_2$, CONH($C_{1-4}$ alkyl), CON($C_{1-4}$ alkyl)$_2$, $NHCO_2(C_{1-4}$ alkyl), $NHSO_2(C_{1-4}$ alkyl), N($C_{1-4}$ alkyl)$SO_2(C_{1-4}$ alkyl), $SO_2(C_{1-4}$ alkyl), $SO_2NH_2$, phenyl, benzyl, and phenoxy;

$R^c$ is, independently at each occurrence, selected from the group consisting of: =O and $R^b$;

$R^d$ is, independently at each occurrence, selected from the group consisting of: =O, halogen, OH, $C_{1-6}$ alkyl substituted with 0-1 OH, $C_{1-4}$ alkoxy, $C_{1-4}$ haloalkyl, $C_{1-4}$ haloalkoxy, $CF_3$, $OCF_3$, $OCF_2CF_2H$, $OCH_2CF_3$, CN, $NH_2$, $NO_2$, NH($C_{1-4}$ alkyl), N($C_{1-4}$ alkyl)$_2$, $CO_2H$, $CO_2(C_{1-4}$ alkyl), CO($C_{1-4}$ alkyl), NHCO($C_{1-4}$ alkyl), —$CH_2NHCO(C_{1-4}$ alkyl), $CONH_2$, CONH($C_{1-4}$ alkyl), CON($C_{1-4}$ alkyl)$_2$, $SO_2(C_{1-4}$ alkyl), $SO_2NH_2$, —$SO_2NH(C_{1-4}$ alkyl), —$SO_2NH(C_{3-6}$ cycloalkyl), —$NHSO_2(C_{1-4}$ alkyl), —$CH_2NHSO_2(C_{1-4}$ alkyl), Si($C_{1-4}$ alkyl)$_3$, and phenyl optionally substituted with one or two substituents independently selected from: halogen, OH, $C_{1-4}$ alkyl, $C_{1-4}$ haloalkyl, $C_{1-4}$ alkyoxy, and NHCO ($C_{1-4}$ alkyl);

$R^e$ is, independently at each occurrence, selected from the group consisting of: H, $C_{1-4}$ alkyl, CO($C_{1-4}$ alkyl), $CO_2(C_{1-4}$ alkyl), $CO_2$(benzyl), and —$(CH_2)_n$-(phenyl optionally substituted with 0-2 halogens);

$R^f$ is, independently at each occurrence, selected from the group consisting of: $C_{1-4}$ alkyl, $C_{2-4}$ alkenyl, $CO_2(C_{1-4}$ alkyl), $CONH_2$, $C_{3-6}$ cycloalkyl, phenyl, and benzyl;

$R^g$ is, independently at each occurrence, selected from the group consisting of: halogen, OH, $C_{1-4}$ alkyl, $C_{2-4}$ alkenyl, $C_{1-4}$ haloalkyl, $C_{1-4}$ alkyoxy, $CO_2(C_{1-4}$ alkyl), $C_{3-6}$ cycloalkyl, and phenyl;

m, at each occurrence, is selected from 0, 1, and 2;

n, at each occurrence, is selected from 0, 1, 2, 3, and 4;

p, at each occurrence, is selected from 0, 1, and 2.

In a second aspect, the present invention includes a compound of Formula (I), or a stereoisomer, a tautomer, a pharmaceutically acceptable salt, or a solvate thereof, within the scope of the first aspect, wherein:

$R^1$ is selected from the group consisting of: $C_{1-6}$ alkyl substituted with 0-2 $R^a$, $C_{2-6}$ alkenyl substituted with 0-2 $R^a$, and —$(CH_2)_n$—W—$R^{1a}$;

W is selected from the group consisting of: a bond, NH, N($C_{1-4}$ alkyl), CO, CONH, CON($C_{1-4}$ alkyl), $SO_2$, $NHCO_2$, and $CHR^f$;

$R^{1a}$ is selected from the group consisting of: $C_{3-6}$ cycloalkyl substituted with 0-3 $R^c$, phenyl substituted with 0-3 $R^b$, naphthyl substituted with 0-2 $R^b$, tetrahydronaphthyl substituted with 0-2 $R^b$, dihydroindenyl substituted with 0-2 $R^c$, and a 5- to 10-membered heterocycle comprising: carbon atoms and 1-4 heteroatoms selected from N, $NR^e$, O, and $S(O)_p$; and wherein said heterocycle is substituted with 0-3 $R^c$;

$R^2$ is selected from the group consisting of: H, halogen, $CF_3$, $OCF_3$, $C_{1-6}$ alkyl substituted with 0-2 $R^a$, $C_{2-6}$ alkenyl substituted with 0-2 $R^a$, —$CO_2(C_{1-4}$ alkyl), —$SO_2$(phenyl), —$(CH_2)_n$—$(C_{3-6}$ cycloalkyl substituted with 0-3 $R^c$), —$(CH_2)_n$-(phenyl substituted with 0-3 $R^b$), —$(CH_2)_n$-(naphthyl substituted with 0-3 $R^b$), and —$(CH_2)_n$-(5- to 10 membered heterocycle comprising: carbon atoms and 1-4 heteroatoms selected from N, $NR^e$, O, and $S(O)_p$), wherein said heterocycle is substituted with 0-3 $R^c$;

$R^3$ is selected from the group consisting of: H, halogen, $CF_3$, $OCF_3$, $C_{1-6}$ alkyl substituted with 0-2 $R^a$, and phenyl substituted with 0-2 $R^b$;

$R^4$ is selected from the group consisting of: $C_{5-6}$ cycloalkyl, phenyl, naphthyl, tetrahydronaphthyl, dihydroindenyl, and a 5- to 10-membered heterocycle comprising: carbon atoms and 1-4 heteroatoms selected from N, $NR^e$, O, and $S(O)_p$; and wherein each moiety is substituted with 0-3 $R^d$;

$R^5$ is selected from the group consisting of: OH, $O(C_{1-4}$ alkyl substituted with 0-1 $CO_2H$), CN, and $NR^7R^8$;

L is $X_1$—Y—$X_2$;

$X_1$, and $X_2$ are, independently at each occurrence, selected from the group consisting of: a bond, a hydrocarbon linker and a hydrocarbon-heteroatom linker; wherein said hydrocarbon linker and hydrocarbon-heteroatom linker may be substituted with 0-1 $R^g$; said hydrocarbon linker may be saturated or unsaturated and has one to five carbon atoms; and said hydrocarbon-heteroatom linker may be saturated or unsaturated and has zero to four carbon atoms and one group selected from O, —CO—, S, —SO—, —$SO_2$—, NH, and $N(C_{1-4}$ alkyl);

Y is selected from the group consisting of: $C_{3-7}$ carbocycle and a 4- to 10-membered heterocycle comprising: carbon atoms and 1-4 heteroatoms selected from N, $NR^e$, O, and $S(O)_p$; wherein each said carbocycle and heterocycle may be optionally substituted with one, two or three substituents independently selected from: halogen, OH, $C_{1-4}$ alkyl, $C_{1-4}$ haloalkyl, and $C_{1-4}$ alkyoxy;

alternatively, $R^4$-L- is

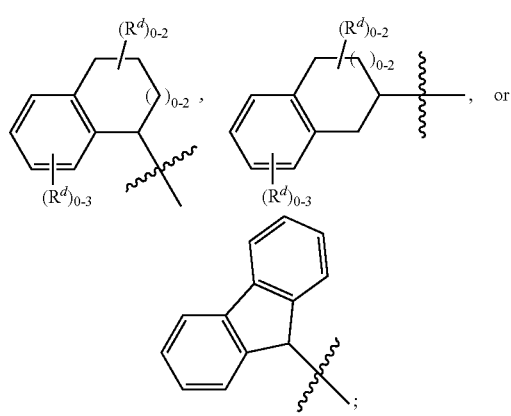

and n, at each occurrence, is selected from 0, 1, 2, and 3.

In a third aspect, the present invention includes a compound of Formula (I), or a stereoisomer, a tautomer, a pharmaceutically acceptable salt, or a solvate thereof, within the scope of the first or second aspect, wherein:

$R^1$ is selected from the group consisting of: $C_{1-6}$ alkyl substituted with 0-2 $R^a$, $C_{2-6}$ alkenyl substituted with 0-2 $R^a$, and —$(CH_2)_n$—W—$R^{1a}$;

W is selected from the group consisting of: a bond, CO, CONH, $CON(C_{1-4}$ alkyl), $SO_2$, and $CHR^f$;

$R^{1a}$ is selected from the group consisting of: $C_{3-6}$ cycloalkyl substituted with 0-3 $R^c$, phenyl substituted with 0-3 $R^b$, and a 5- to 6-membered heterocycle comprising: carbon atoms and 1-4 heteroatoms selected from N, $NR^e$, O, and $S(O)_p$; and wherein said heterocycle is substituted with 0-3 $R^c$;

$R^5$ is selected from the group consisting of: OH and $C_{1-6}$ alkoxy;

L is $X_1$—Y—$X_2$;

$X_1$ is selected from the group consisting of: a bond, a hydrocarbon linker and a hydrocarbon-heteroatom linker; wherein said hydrocarbon linker and hydrocarbon-heteroatom linker may be substituted with 0-1 $R^g$; said hydrocarbon linker has one to four carbon atoms and may be saturated or unsaturated; and said hydrocarbon-heteroatom linker may be saturated or unsaturated and has zero to three carbon atoms and one group selected from O, —CO—, S, —SO—, —$SO_2$—, NH, and $N(C_{1-4}$ alkyl);

$X_2$ is selected from the group consisting of: a bond, a hydrocarbon linker and a hydrocarbon-heteroatom linker; wherein said hydrocarbon linker and hydrocarbon-heteroatom linker may be substituted with 0-1 $R^g$; said hydrocarbon linker has one to five carbon atoms and may be saturated or unsaturated; and said hydrocarbon-heteroatom linker may be saturated or unsaturated and has zero to four carbon atoms and one group selected from O, —CO—, S, —SO—, —$SO_2$—, NH, and $N(C_{1-4}$ alkyl); and Y is, independently at each occurrence, selected from the group consisting of: $C_{3-6}$ cycloalkylene, phenylene, azetidinylene, pyrrolidinylene, piperidinylene, thiazolylene, and oxadiazolylene; wherein said phenylene may be optionally substituted with one or two substituents independently selected from: halogen, OH, $C_{1-4}$ alkyl, $C_{1-4}$ haloalkyl, and $C_{1-4}$ alkyoxy;

alternatively, $R^4$-L- is

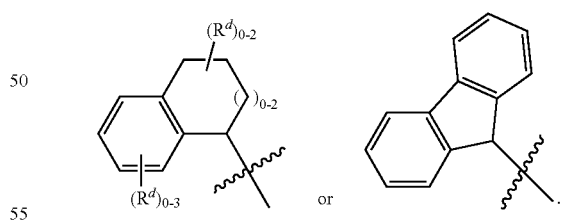

In a fourth aspect, the present invention includes a compound of Formula (I), or a stereoisomer, a tautomer, a pharmaceutically acceptable salt, or a solvate thereof, within the scope of the first or second aspect, wherein:

$R^1$ is selected from the group consisting of: H, $C_{1-4}$ alkyl substituted with 0-1 $CF_3$, —$CH_2CO_2(C_{1-4}$ alkyl), cyclopropyl, cyclopropylmethyl, phenyl, 4-$CF_3$-phenyl, 3-halo-4-$CO_2(C_{1-4}$ alkyl)-phenyl, 2-($C_{1-4}$ alkoxy)-5-halo-phenyl, benzyl, 4-$CO_2$H-benzyl, 4-$CO_2(C_{1-4}$ alkyl)-benzyl, 4-$SO_2(C_{1-4}$ alkyl)-benzyl, 2-halo-phenethyl, 4-halo-phenethyl, 2-OH-phenethyl, —$SO_2$(phenyl), and pyrid-4-yl;

$R^2$ is selected from the group consisting of: H, halogen, $CF_3$, $OCF_3$, $C_{1-4}$ alkyl, $C_{2-4}$ alkenyl, —$SO_2$(phenyl), phenyl substituted with 0-2 $R^c$, naphthyl substituted with 0-2 $R^c$, and a heterocycle selected from: thienyl, oxadiazolyl, pyridyl, indolyl, quinolinyl, and isoquinolinyl; wherein said heterocycle is substituted with 0-2 $R^c$;

$R^3$ is selected from the group consisting of: H, $C_{1-4}$ alkyl and phenyl substituted with 0-2 $R^c$;

$R^4$ is selected from the group consisting of: phenyl substituted with 0-3 $R^d$, naphthyl, pyrrolidinyl, piperidinyl, morpholinyl,

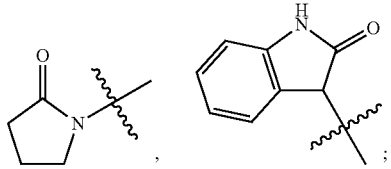 [SMILES: *N1CCCC1=O ; *C1C(=O)Nc2ccccc21]

L is selected from the group consisting of: —$(CH_2)_{0-2}$-phenylene-$C_{1-4}$ alkylene-, -phenylene-O—$C_{1-3}$ alkylene-, —O-phenylene-$C_{1-3}$ alkylene-, —O-phenylene-O—$C_{1-3}$ alkylene-, S-phenylene-$C_{1-3}$ alkylene-, —NH-phenylene-$C_{1-3}$ alkylene-,

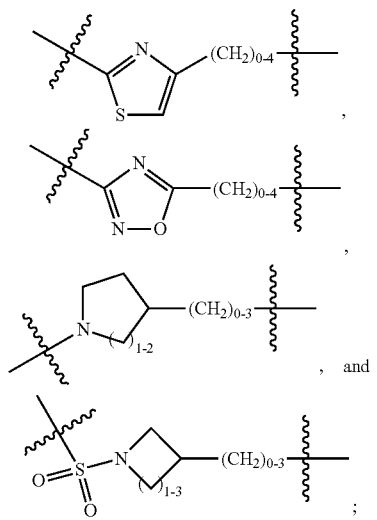

wherein each said alkylene may be straight or branched; and said phenylene may be optionally substituted with one or two substituents independently selected from: halogen, OH, $C_{1-4}$ alkyl, $C_{1-4}$ haloalkyl, and $C_{1-4}$ alkyoxy;

$R^d$ is, independently at each occurrence, selected from the group consisting of: halogen, $C_{1-6}$ alkyl, $C_{1-4}$ alkoxy, $C_{1-4}$ haloalkyl, $CF_3$, $OCF_3$, $CO_2(C_{1-4}$ alkyl), $NO_2$, and phenyl optionally substituted with one or two substituents independently selected from: halogen, OH, $C_{1-4}$ alkyl, $C_{1-4}$ haloalkyl, and $C_{1-4}$ alkyoxy; and alternatively, $R^4$-L- is

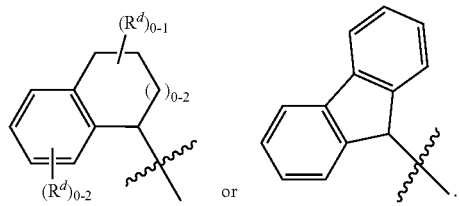

In a fifth aspect, the present invention includes a compound of Formula (II), or a stereoisomer, a tautomer, a pharmaceutically acceptable salt, or a solvate thereof, within the scope of any of the above aspects wherein:

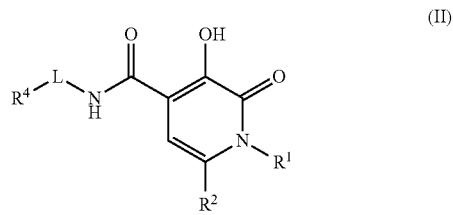

$R^1$ is selected from the group consisting of: H, $C_{1-4}$ alkyl substituted with 0-1 $CF_3$, —$CH_2CO_2(C_{1-4}$ alkyl), cyclopropyl, cyclopropylmethyl, phenyl, 4-$CF_3$-phenyl, 3-halo-4-$CO_2(C_{1-4}$ alkyl)-phenyl, benzyl, 2-halo-benzyl, 4-$CO_2H$-benzyl, 4-$CO_2(C_{1-4}$ alkyl)-benzyl, 4-$SO_2(C_{1-4}$ alkyl)-benzyl, 2-halo-phenethyl, 4-halo-phenethyl, 2-OH-phenethyl, and pyrid-4-yl;

$R^2$ is selected from the group consisting of: H, halogen, $C_{1-4}$ alkyl, $C_{2-4}$ alkenyl, $CF_3$, phenyl, 3-halo-phenyl, 4-halo-phenyl, 3-$C_{1-4}$ alkyl-phenyl, 3-$CF_3$-phenyl, 4-$CF_3$-phenyl, 3-$OCF_3$-phenyl, 4-$OCF_3$-phenyl, 4-OH-phenyl, 4-CN-phenyl, 3-$NH_2$-phenyl, 3-N($C_{1-4}$ alkyl)-2-phenyl, 3-$CO_2H$-phenyl, 3-$CONH_2$-phenyl, 4-$CONH_2$-phenyl, 3-CON($C_{1-4}$ alkyl)-2-phenyl, 4-CON($C_{1-4}$ alkyl)-2-phenyl, 3-$NHSO_2$($C_{1-4}$ alkyl)-phenyl, 4-$NHSO_2$($C_{1-4}$ alkyl)-phenyl, 4-$SO_2$($C_{1-4}$ alkyl)-phenyl, 3-$SO_2NH_2$-phenyl, 3-biphenyl, 4-biphenyl, 3-halo-4-halo-phenyl, 3-halo-5-halo-phenyl, 3-$C_{1-4}$ alkyl-4-halo-phenyl, 3-$CF_3$-5-halo-phenyl, 3-$CF_3$-4-halo-phenyl, 3-halo-4-$CF_3$-phenyl, 3-$CF_3$-4-OH-phenyl, 3,5-di$CF_3$-phenyl, 3-$OCF_2CHF_2$-5-halo-phenyl, 1-naphthyl, 2-naphthyl, thien-2-yl, thien-3-yl, 5-($C_{1-4}$ alkyl)-1,2,4-oxadiazol-3-yl, pyrid-4-yl, 1-$C_{1-4}$ alkyl-indol-5-yl, 3-quinolinyl, 5-quinolinyl, 6-quinolinyl, and 5-isoquinolinyl;

$R^4$ is selected from the group consisting of: phenyl, 2-($C_{1-4}$ alkyl)-phenyl, 3-($C_{1-4}$ alkyl)-phenyl, 4-($C_{1-4}$ alkyl)-phenyl, 2-($C_{1-4}$ alkoxy)-phenyl, 3-($C_{1-4}$ alkoxy)-phenyl, 4-($C_{1-4}$ alkoxy)-phenyl, 2-halo-phenyl, 3-halo-phenyl, 4-halo-phenyl, 2-$CF_3$-phenyl, 3-$CF_3$-phenyl, 4-$CF_3$-phenyl, 3-$OCF_3$-phenyl, 4-$OCF_3$-phenyl, 3-$CO_2(C_{1-4}$ alkyl)-phenyl, 4-$CO_2$($C_{1-4}$ alkyl)-phenyl, 2-$NO_2$-phenyl, 3-$NO_2$-phenyl, 4-$NO_2$-phenyl, 3-halo-4-halo-phenyl, 3-halo-5-halo-phenyl, 2-halo-6-halo-phenyl, 1-naphthyl, 2-naphthyl, pyrrolidin-1-yl, and morpholin-4-yl;

L is selected from the group consisting of: -(1,2-phenylene)-$C_{1-3}$ alkylene-, -(1,3-phenylene)-$C_{1-3}$ alkylene-, -(1,2-phenylene)-O—$C_{1-3}$ alkylene-, -(1,3-phenylene)-O—$C_{1-3}$ alkylene-, -(1,4-phenylene)-O—$C_{1-3}$ alkylene-, —O-(1,4-phenylene)-$C_{1-3}$ alkylene-, —O-(1,3-phenylene)-O—$C_{1-3}$ alkylene-, —O-(1,4-phenylene)-O—$C_{1-3}$ alkylene-, —NH-(1,3-phenylene)-$C_{1-3}$ alkylene-,

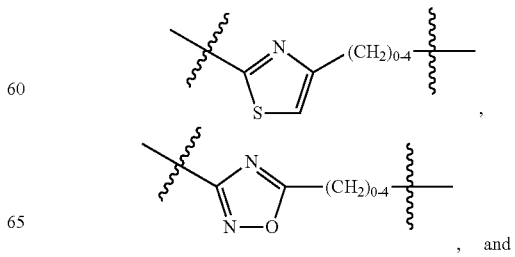

-continued

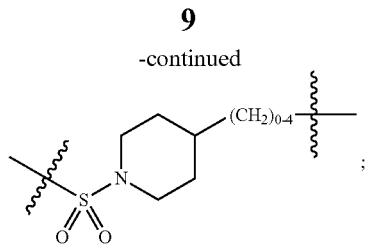

wherein each said alkylene may be straight or branched; and alternatively, $R^4$-L- is

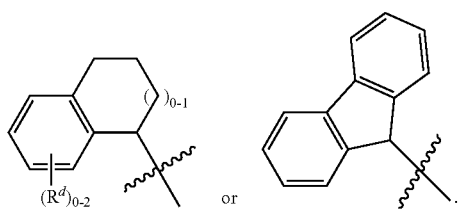

In a sixth aspect, the present invention includes a compound of Formula (II), or a stereoisomer, a tautomer, a pharmaceutically acceptable salt, or a solvate thereof, within the scope of any of the above aspects wherein:

$R^1$ is selected from the group consisting of: $C_{1-4}$ alkyl substituted with 0-1 $CF_3$, and cyclopropylmethyl;

$R^2$ is selected from the group consisting of: H, halogen, $CF_3$, and 3-$CF_3$-5-halo-phenyl;

$R^4$ is selected from the group consisting of: phenyl, 4-halo-phenyl, 2-$CF_3$-phenyl, 3-halo-4-halo-phenyl, pyrrolidin-1-yl, and morpholin-4-yl;

L is selected from the group consisting of: 1,4-cyclohexylene, -(1,2-phenylene)-$CH_2$—, -(1,3-phenylene)-$CH_2$—, -(1,3-phenylene)-CH($C_{1-4}$ alkyl)-, -(1,2-phenylene)-O($CH_2$)$_3$—, -(1,3-phenylene)-O($CH_2$)$_3$—, -(1,4-phenylene)-O($CH_2$)$_3$—, —O-(1,4-phenylene)-$CH_2$—, —O-(1,3-phenylene)-O($CH_2$)$_3$—, —O-(1,4-phenylene)-O($CH_2$)$_3$—, —NH-(1,3-phenylene)-$CH_2$—,

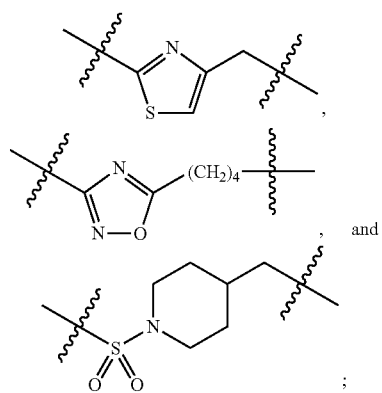

and
alternatively, $R^4$-L- is

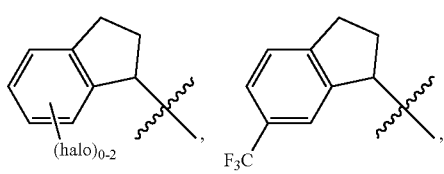

-continued

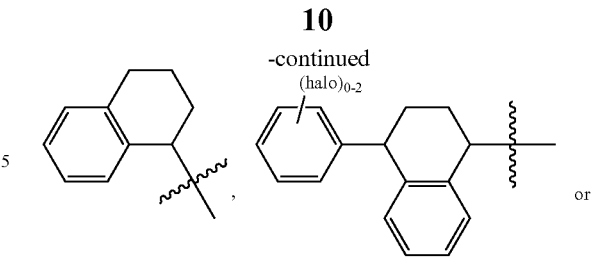

In a seventh aspect, the present invention includes a compound of Formula (II), or a stereoisomer, a tautomer, a pharmaceutically acceptable salt, or a solvate thereof, within the scope of any of the above aspects wherein:

$R^1$ is selected from the group consisting of: methyl, isobutyl, $CH_2CF_3$, $CH_2CH_2CF_3$, and cyclopropylmethyl;

$R^2$ is selected from the group consisting of: H, $C_1$, $CF_3$, and 3-$CF_3$-5-F-phenyl;

$R^4$ is selected from the group consisting of: phenyl, 4-F-phenyl, 4-Cl-phenyl, 2-$CF_3$-phenyl, 3,4-diCl-phenyl, pyrrolidin-1-yl, and morpholin-4-yl; and L is selected from the group consisting of: 1,4-cyclohexylene, -(1,2-phenylene)-$CH_2$—, -(1,3-phenylene)-$CH_2$—, -(1,3-phenylene)-CH($CH_3$)—, -(1,2-phenylene)-O($CH_2$)$_3$—, -(1,3-phenylene)-O($CH_2$)$_3$—, -(1,4-phenylene)-O($CH_2$)$_3$—, —O-(1,4-phenylene)-$CH_2$—, —O-(1,3-phenylene)-O($CH_2$)$_3$—, —O-(1,4-phenylene)-O($CH_2$)$_3$—, —NH-(1,3-phenylene)-$CH_2$—,

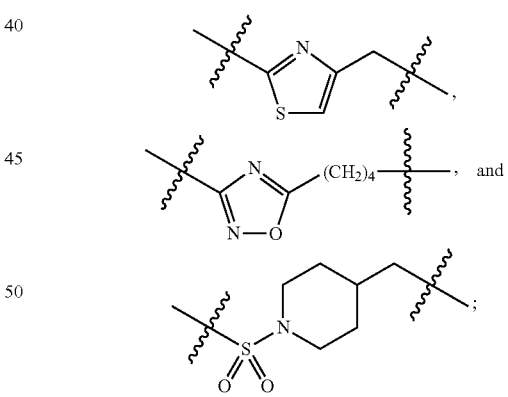

and
alternatively, $R^4$-L- is

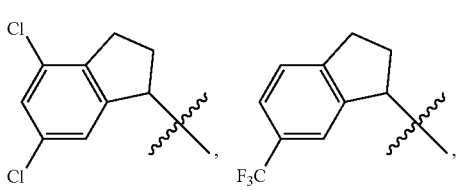

-continued

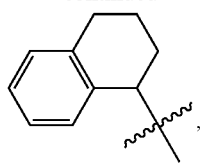

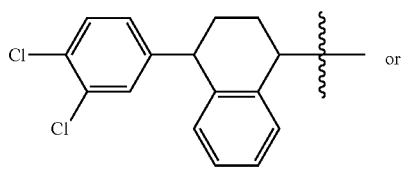 or

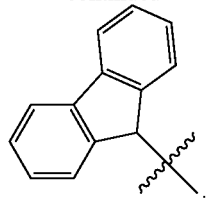

In an eighth aspect, the present invention includes a compound of Formula (II), or a stereoisomer, a tautomer, a pharmaceutically acceptable salt, or a solvate thereof, within the scope of any of the above aspects wherein:

$R^1$, $R^2$, $R^4$ and L are selected in concert from the group consisting of:

| $R^1$ | $R^2$ | $R^4$ | L |
|---|---|---|---|
| $CH_3$ | Cl | 4-Cl—Ph | cyclohexyl |
| $CH_3$ | 3-$CF_3$-5-F—Ph | Ph | cyclohexyl |
| $CH_3$ | H | 3,4-diCl—Ph | piperidinyl sulfonamide |
| $CH_2CF_3$ | H | Ph | cyclohexyl |
| $CH_2CH_2CF_3$ | H | Ph | cyclohexyl |
| cyclopropylmethyl | H | Ph | cyclohexyl |
| $CH_3$ | Cl | Ph | cyclohexyl |
| $CH_3$ | H | 4-F—Ph | -O-phenyl-CH2- |
| $CH_2CF_3$ | H | 4-F—Ph | o-xylyl |

-continued
| R¹ | R² | R⁴ | L |
|---|---|---|---|
| CH₃ | CF₃ | 4-Cl—Ph | 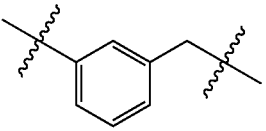 [SMILES: *Cc1cccc(*)c1] |
| CH₃ | H | Ph | 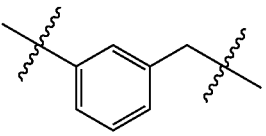 [SMILES: *Cc1cccc(*)c1] |
| CH₃ | H | Ph | 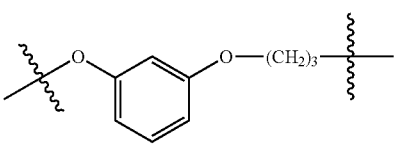 |
| i-Bu | H | 4-F—Ph | 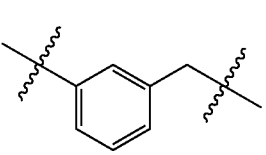 [SMILES: *Cc1cccc(*)c1] |
| CH₃ | H | Ph | 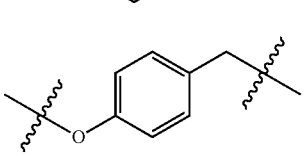 |
| CH₃ | H | Ph | 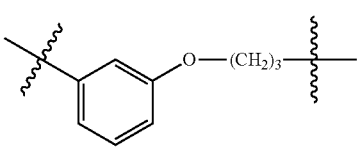 |
| CH₃ | H | 4-F—Ph | 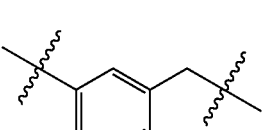 |
| CH₃ | H | Ph | 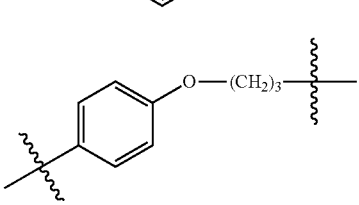 |
| CH₃ | H | Ph | 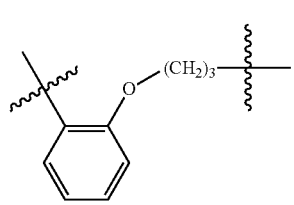 |
| CH₃ | H | Ph | 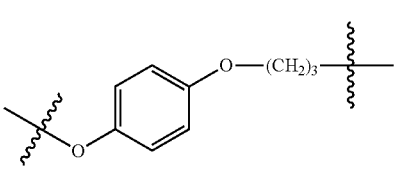 |

| R¹ | R² | R⁴ | L |
|---|---|---|---|
| CH₃ | H | 4-F—Ph | 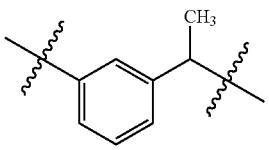 [SMILES: *c1cccc(C(*)C)c1] |
| CH₃ | H | Ph | 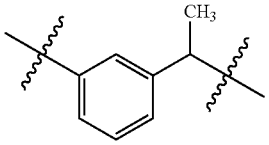 [SMILES: *c1cccc(C(*)C)c1] |
| CH₃ | H | 4-Cl—Ph | 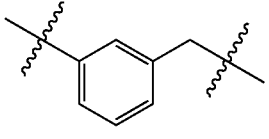 [SMILES: *Cc1cccc(*)c1] |
| CH₃ | H | Ph | 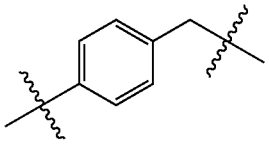 [SMILES: *Cc1ccc(*)cc1] |
| CH₃ | H | 2-CF₃—Ph | 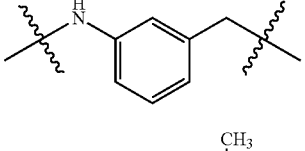 |
| CH₃ | H | morpholin-4-yl | 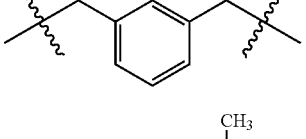 |
| CH₃ | H | pyrrolidin-1-yl | 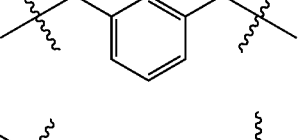 |
| CH₃ | H | 3,4-diCl—Ph | 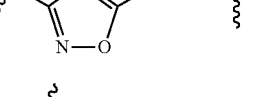 |
| CH₃ | 3-CF₃-5-F—Ph | Ph | 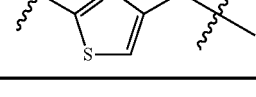 |

In a ninth aspect, the present invention includes a compound of Formula (II), or a stereoisomer, a tautomer, a pharmaceutically acceptable salt, or a solvate thereof, within the scope of any of the above aspects wherein:

$R^1$ is selected from the group consisting of: methyl, isobutyl, and $CH_2CF_3$;

$R^2$ is selected from the group consisting of: H, $C_1$, $CF_3$, and 3-$CF_3$-5-F-phenyl;

$R^4$ is selected from the group consisting of: phenyl, 4-F-phenyl, 4-Cl-phenyl, and 3,4-diCl-phenyl;

L is selected from the group consisting of: 1,4-cyclohexylene, -(1,2-phenylene)-$CH_2$—, -(1,3-phenylene)-$CH_2$—, -(1,3-phenylene)-$CH(CH_3)$—, -(1,2-phenylene)-$O(CH_2)_3$—, -(1,3-phenylene)-$O(CH_2)_3$—, -(1,4-phenylene)-$O(CH_2)_3$—, —O-(1,4-phenylene)-$CH_2$—, —O-(1,3-phenylene)-$O(CH_2)_3$—, —O-(1,4-phenylene)-$O(CH_2)_3$—,

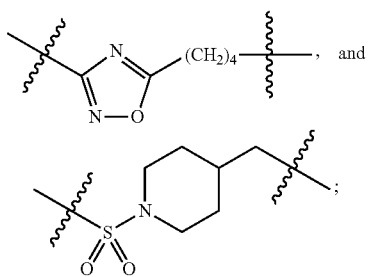

and
alternatively, R⁴-L- is

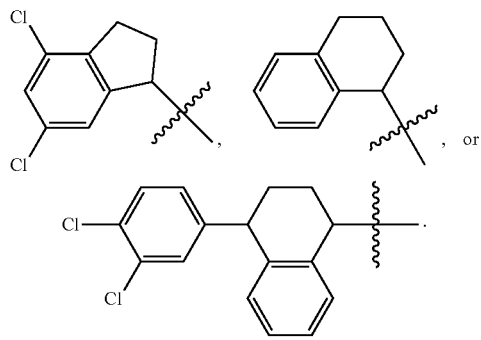

In a tenth aspect, the present invention includes a compound of Formula (II), or a stereoisomer, a tautomer, a pharmaceutically acceptable salt, or a solvate thereof, within the scope of any of the above aspects wherein: $R^1$ is selected from the group consisting of: methyl, isobutyl, and $CH_2CF_3$;

$R^2$ is selected from the group consisting of: H, $C_1$, $CF_3$, and 3-$CF_3$-5-F-phenyl;

$R^4$ is selected from the group consisting of: phenyl, 4-F-phenyl, 4-Cl-phenyl, and 3,4-diCl-phenyl;

L is selected from the group consisting of: 1,4-cyclohexylene, -(1,2-phenylene)-$CH_2$—, -(1,3-phenylene)-$CH_2$—, -(1,2-phenylene)-O($CH_2$)$_3$—, -(1,3-phenylene)-O($CH_2$)$_3$—, -(1,4-phenylene)-O($CH_2$)$_3$—, —O-(1,4-phenylene)-$CH_2$—, —O-(1,3-phenylene)-O($CH_2$)$_3$—, and

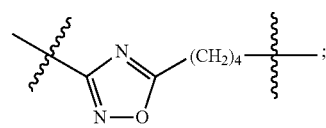

and
alternatively, R⁴-L- is

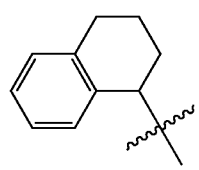

In another aspect, the present invention includes a compound of Formula (I) or (II), or a stereoisomer, a tautomer, a pharmaceutically acceptable salt, or a solvate thereof, within the scope of any of the above aspects wherein:

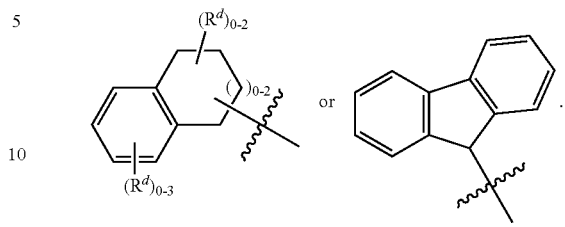

R⁴-L- is

In another aspect, the present invention includes a compound of Formula (I) or (II), or a stereoisomer, a tautomer, a pharmaceutically acceptable salt, or a solvate thereof, within the scope of any of the above aspects wherein:

R⁴-L- is

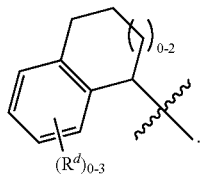

In an eleventh aspect, the present invention provides a compound selected from the exemplified examples or a stereoisomer, a tautomer, a pharmaceutically acceptable salt, or a solvate thereof.

In another aspect, the present invention provides a compound selected from any subset list of the exemplified examples or any one of the exemplified examples or a stereoisomer, a tautomer, a pharmaceutically acceptable salt, or a solvate thereof, within the scope of the eleventh aspect.

II. Other Embodiments of the Invention

In another embodiment, the present invention provides a composition comprising at least one of the compounds of the present invention or a stereoisomer, a tautomer, a pharmaceutically acceptable salt, or a solvate thereof.

In another embodiment, the present invention provides a pharmaceutical composition comprising a pharmaceutically acceptable carrier and at least one of the compounds of the present invention or a stereoisomer, a tautomer, a pharmaceutically acceptable salt, or a solvate thereof.

In another embodiment, the present invention provides a pharmaceutical composition, comprising: a pharmaceutically acceptable carrier and a therapeutically effective amount of at least one of the compounds of the present invention or a stereoisomer, a tautomer, a pharmaceutically acceptable salt, or a solvate thereof.

In another embodiment, the present invention provides a process for making a compound of the present invention.

In another embodiment, the present invention provides an intermediate for making a compound of the present invention.

In another embodiment, the present invention provides a pharmaceutical composition as defined above further comprising additional therapeutic agent(s).

In another embodiment, the present invention provides a method for the treatment and/or prophylaxis of dyslipidemias and the sequelae thereof comprising administering to a patient in need of such treatment and/or prophylaxis a therapeutically effective amount of at least one of the compounds of the present invention, alone, or, optionally, in combination with another compound of the present invention and/or at least one other type of therapeutic agent.

Examples of diseases or disorders associated with the activity of endothelial lipase that can be prevented, modulated, or treated according to the present invention include, but are not limited to, atherosclerosis, coronary heart disease, coronary artery disease, coronary vascular disease, cerebrovascular disorders, Alzheimer's disease, venous thrombosis, peripheral vascular disease, dyslipidemia, hyperbetalipoproteinemia, hypoalphalipoproteinemia, hypercholesterolemia, hypertriglyceridemia, familial-hypercholesterolemia, cardiovascular disorders, angina, ischemia, cardiac ischemia, stroke, myocardial infarction, reperfusion injury, angioplastic restenosis, hypertension, vascular complications of diabetes, obesity or endotoxemia.

In one embodiment, the present invention provides a method for the treatment and/or prophylaxis of atherosclerosis, coronary heart disease, cerebrovascular disorders and dyslipidemia, comprising administering to a patient in need of such treatment and/or prophylaxis a therapeutically effective amount of at least one of the compounds of the present invention, alone, or, optionally, in combination with another compound of the present invention and/or at least one other type of therapeutic agent.

In another embodiment, the present invention provides a compound of the present invention for use in therapy.

In another embodiment, the present invention provides a compound of the present invention for use in therapy for the treatment and/or prophylaxis of dyslipidemias and the sequelae thereof.

In another embodiment, the present invention also provides the use of a compound of the present invention for the manufacture of a medicament for the treatment and/or prophylaxis of dyslipidemias and the sequelae thereof.

In another embodiment, the present invention provides a method for the treatment and/or prophylaxis of dyslipidemias and the sequelae thereof, comprising: administering to a patient in need thereof a therapeutically effective amount of a first and second therapeutic agent, wherein the first therapeutic agent is a compound of the present invention.

In another embodiment, the present invention provides a combined preparation of a compound of the present invention and additional therapeutic agent(s) for simultaneous, separate or sequential use in therapy.

In another embodiment, the present invention provides a combined preparation of a compound of the present invention and additional therapeutic agent(s) for simultaneous, separate or sequential use in the treatment and/or prophylaxis of dyslipidemias and the sequelae thereof.

The compounds of the present invention may be employed in combination with additional therapeutic agent(s) selected from one or more, preferably one to three, of the following therapeutic agents: anti-atherosclerotic agents, anti-dyslipidemic agents, anti-diabetic agents, anti-hyperglycemic agents, anti-hyperinsulinemic agents, anti-thrombotic agents, anti-retinopathic agents, anti-neuropathic agents, anti-nephropathic agents, anti-ischemic agents, anti-hypertensive agents, anti-obesity agents, anti-hyperlipidemic agents, anti-hypertriglyceridemic agents, anti-hypercholesterolemic agents, anti-restenotic agents, anti-pancreatic agents, lipid lowering agents, anorectic agents, memory enhancing agents, anti-dementia agents, cognition promoting agents, appetite suppressants, treatments for heart failure, treatments for peripheral arterial disease, treatment for malignant tumors, and anti-inflammatory agents.

In another embodiment, additional therapeutic agent(s) used in combined pharmaceutical compositions or combined methods or combined uses, are selected from one or more, preferably one to three, of the following therapeutic agents in treating atherosclerosis: anti-hyperlipidemic agents, plasma HDL-raising agents, anti-hypercholesterolemic agents, cholesterol biosynthesis inhibitors (such as HMG CoA reductase inhibitors), acyl-coenzyme A:cholesterol acytransferase (ACAT) inhibitors, LXR agonist, probucol, raloxifene, nicotinic acid, niacinamide, cholesterol absorption inhibitors, bile acid sequestrants (such as anion exchange resins, or quaternary amines (e.g., cholestyramine or colestipol)), low density lipoprotein receptor inducers, clofibrate, fenofibrate, benzofibrate, cipofibrate, gemfibrizol, vitamin $B_6$, vitamin $B_{12}$, anti-oxidant vitamins, β-blockers, anti-diabetes agents, angiotensin II antagonists, angiotensin converting enzyme inhibitors, platelet aggregation inhibitors, fibrinogen receptor antagonists, aspirin or fibric acid derivatives.

In another embodiment, additional therapeutic agent(s) used in combined pharmaceutical compositions or combined methods or combined uses, are selected from one or more, preferably one to three, of the following therapeutic agents in treating cholesterol biosynthesis inhibitor, particularly an HMG-CoA reductase inhibitor. Examples of suitable HMG-CoA reductase inhibitors include, but are not limited to, lovastatin, simvastatin, pravastatin, fluvastatin, atorvastatin, and rivastatin.

The present invention may be embodied in other specific forms without departing from the spirit or essential attributes thereof. This invention encompasses all combinations of preferred aspects of the invention noted herein. It is understood that any and all embodiments of the present invention may be taken in conjunction with any other embodiment or embodiments to describe additional embodiments. It is also understood that each individual element of the embodiments is its own independent embodiment. Furthermore, any element of an embodiment is meant to be combined with any and all other elements from any embodiment to describe an additional embodiment.

III. Chemistry

Throughout the specification and the appended claims, a given chemical formula or name shall encompass all stereo and optical isomers and racemates thereof where such isomers exist. Unless otherwise indicated, all chiral (enantiomeric and diastereomeric) and racemic forms are within the scope of the invention. Many geometric isomers of C=C double bonds, C=N double bonds, ring systems, and the like can also be present in the compounds, and all such stable isomers are contemplated in the present invention. Cis- and trans- (or E- and Z-) geometric isomers of the compounds of the present invention are described and may be isolated as a mixture of isomers or as separated isomeric forms. The present compounds can be isolated in optically active or racemic forms. Optically active forms may be prepared by resolution of racemic forms or by synthesis from optically active starting materials. All processes used to prepare compounds of the present invention and intermediates made therein are considered to be part of the present invention. When enantiomeric or diastereomeric products are prepared, they may be separated by conventional methods, for example, by chromatography or fractional crystallization. Depending on the process conditions the end products of the present invention are obtained either in free (neutral) or salt form. Both the free form and the salts of these end products are within the scope of the invention. If so desired, one form of a compound may be converted into another form. A free base or acid may be converted into a salt; a salt may be converted into the free compound or another salt; a mixture of isomeric compounds of the present invention may be separated into the individual isomers. Compounds of the present invention, free form and salts thereof, may exist in multiple tautomeric forms, in which hydrogen atoms are transposed to other parts of the molecules and the chemical bonds between the atoms of the molecules are consequently rearranged. It should be understood that all tautomeric forms, insofar as they may exist, are included within the invention.

As used herein, the term "alkyl" or "alkylene" is intended to include both branched and straight-chain saturated aliphatic hydrocarbon groups having the specified number of carbon atoms. For example, "$C_1$ to $C_{10}$ alkyl" or "$C_{1-10}$ alkyl" (or alkylene), is intended to include $C_1$, $C_2$, $C_3$, $C_4$, $C_5$, $C_6$, $C_7$, $C_8$, $C_9$, and $C_{10}$ alkyl groups. Additionally, for example, "$C_1$ to $C_6$ alkyl" or "$C_{1-6}$ alkyl" denotes alkyl having 1 to 6 carbon atoms. Alkyl group can be unsubstituted or substituted with at least one hydrogen being replaced by another chemical group. Example alkyl groups include, but are not limited to, methyl (Me), ethyl (Et), propyl (e.g., n-propyl and isopropyl), butyl (e.g., n-butyl, isobutyl, t-butyl), and pentyl (e.g., n-pentyl, isopentyl, neopentyl). When "$C_0$ alkyl" or "$C_0$ alkylene" is used, it is intended to denote a direct bond.

Alkenyl" or "alkenylene" is intended to include hydrocarbon chains of either straight or branched configuration having the specified number of carbon atoms and one or more, preferably one to two, carbon-carbon double bonds that may occur in any stable point along the chain. For example, "$C_2$ to $C_6$ alkenyl" or "$C_{2-6}$ alkenyl" (or alkenylene), is intended to include $C_2$, $C_3$, $C_4$, $C_5$, and $C_6$ alkenyl groups. Examples of alkenyl include, but are not limited to, ethenyl, 1-propenyl, 2-propenyl, 2-butenyl, 3-butenyl, 2-pentenyl, 3, pentenyl, 4-pentenyl, 2-hexenyl, 3-hexenyl, 4-hexenyl, 5-hexenyl, 2-methyl-2-propenyl, and 4-methyl-3-pentenyl.

"Alkynyl" or "alkynylene" is intended to include hydrocarbon chains of either straight or branched configuration having one or more, preferably one to three, carbon-carbon triple bonds that may occur in any stable point along the chain. For example, "$C_2$ to $C_6$ alkynyl" or "$C_{2-6}$ alkynyl" (or alkynylene), is intended to include $C_2$, $C_3$, $C_4$, $C_5$, and $C_6$ alkynyl groups; such as ethynyl, propynyl, butynyl, pentynyl, and hexynyl.

The term "alkoxy" or "alkyloxy" refers to an —O-alkyl group. "$C_1$ to $C_6$ alkoxy" or "$C_{1-6}$ alkoxy" (or alkyloxy), is intended to include $C_1$, $C_2$, $C_3$, $C_4$, $C_5$, and $C_6$ alkoxy groups. Example alkoxy groups include, but are not limited to, methoxy, ethoxy, propoxy (e.g., n-propoxy and isopropoxy), and t-butoxy. Similarly, "alkylthio" or "thioalkoxy" represents an alkyl group as defined above with the indicated number of carbon atoms attached through a sulphur bridge; for example methyl-S— and ethyl-S—.

"Halo" or "halogen" includes fluoro, chloro, bromo, and iodo. "Haloalkyl" is intended to include both branched and straight-chain saturated aliphatic hydrocarbon groups having the specified number of carbon atoms, substituted with one or more halogens. Examples of haloalkyl include, but are not limited to, fluoromethyl, difluoromethyl, trifluoromethyl, trichloromethyl, pentafluoroethyl, pentachloroethyl, 2,2,2-trifluoroethyl, heptafluoropropyl, and heptachloropropyl. Examples of haloalkyl also include "fluoroalkyl" that is intended to include both branched and straight-chain saturated aliphatic hydrocarbon groups having the specified number of carbon atoms, substituted with one or more fluorine atoms.

"Haloalkoxy" or "haloalkyloxy" represents a haloalkyl group as defined above with the indicated number of carbon atoms attached through an oxygen bridge. For example, "$C_1$ to $C_6$ haloalkoxy" or "$C_{1-6}$ haloalkoxy", is intended to include $C_1$, $C_2$, $C_3$, $C_4$, $C_5$, and $C_6$ haloalkoxy groups. Examples of haloalkoxy include, but are not limited to, trifluoromethoxy, 2,2,2-trifluoroethoxy, and pentafluorothoxy. Similarly, "haloalkylthio" or "thiohaloalkoxy" represents a haloalkyl group as defined above with the indicated number of carbon atoms attached through a sulphur bridge; for example trifluoromethyl-S—, and pentafluoroethyl-S—.

The term "cycloalkyl" refers to cyclized alkyl groups, including mono-, bi- or poly-cyclic ring systems. "$C_3$ to $C_7$ cycloalkyll" or "$C_{3-7}$ cycloalkyl" is intended to include $C_3$, $C_4$, $C_5$, $C_6$, and $C_7$ cycloalkyl groups. Example cycloalkyl groups include, but are not limited to, cyclopropyl, cyclobutyl, cyclopentyl, cyclohexyl, and norbornyl. Branched cycloalkyl groups such as 1-methylcyclopropyl and 2-methylcyclopropyl are included in the definition of "cycloalkyl".

As used herein, "carbocycle," "carbocyclyl," or "carbocyclic residue" is intended to mean any stable 3-, 4-, 5-, 6-, 7-, or 8-membered monocyclic or bicyclic or 7-, 8-, 9-, 10-, 11-, 12-, or 13-membered bicyclic or tricyclic ring, any of which may be saturated, partially unsaturated, unsaturated or aromatic. Examples of such carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, [3.3.0]bicyclooctane, [4.3.0]bicyclononane, [4.4.0] bicyclodecane (decalin), [2.2.2]bicyclooctane, fluorenyl, phenyl, naphthyl, indanyl, adamantyl, anthracenyl, and tetrahydronaphthyl (tetralin). As shown above, bridged rings are also included in the definition of carbocycle (e.g., [2.2.2] bicyclooctane). Preferred carbocycles, unless otherwise specified, are cyclopropyl, cyclobutyl, cyclopentyl, cyclohexyl, phenyl, indanyl, and tetrahydronaphthyl. When the term "carbocycle" is used, it is intended to include "aryl." A bridged ring occurs when one or more, preferably one to three, carbon atoms link two non-adjacent carbon atoms. Preferred bridges are one or two carbon atoms. It is noted that a bridge always converts a monocyclic ring into a tricyclic ring. When a ring is bridged, the substituents recited for the ring may also be present on the bridge.

As used herein, the term "bicyclic carbocycle" or "bicyclic carbocyclic group" is intended to mean a stable 9- or 10-membered carbocyclic ring system that contains two fused rings and consists of carbon atoms. Of the two fused rings, one ring is a benzo ring fused to a second ring; and the second ring is a 5- or 6-membered carbon ring which is saturated, partially unsaturated, or unsaturated. The bicyclic carbocyclic group may be attached to its pendant group at any carbon atom which results in a stable structure. The bicyclic carbocyclic group described herein may be substituted on any carbon if the resulting compound is stable. Examples of a bicyclic carbocyclic group are, but not limited to, naphthyl, 1,2-dihydronaphthyl, 1,2,3,4-tetrahydronaphthyl, and indanyl.

"Aryl" groups refer to monocyclic or polycyclic aromatic hydrocarbons, including, for example, phenyl, naphthyl, and phenanthranyl. Aryl moieties are well known and described, for example, in Lewis, R. J., ed., *Hawley's Condensed Chemical Dictionary*, 13th Edition, J. Wiley & Sons, Inc., New York (1997). "$C_6$ or $C_{10}$ aryl" or "$C_{6-10}$ aryl" refers to phenyl and naphthyl. Unless otherwise specified, "aryl", "$C_6$ or $C_{10}$ aryl,"

"C$_{6-10}$ aryl," or "aromatic residue" may be unsubstituted or substituted with 1 to 5 groups, preferably 1 to 3 groups, selected from —OH, —OCH$_3$, —Cl, —F, —Br, —I, —CN, —NO$_2$, —NH$_2$, —N(CH$_3$)H, —N(CH$_3$)$_2$, —CF$_3$, —OCF$_3$, —C(O)CH$_3$, —SCH$_3$, —S(O)CH$_3$, —S(O)$_2$CH$_3$, —CH$_3$, —CH$_2$CH$_3$, —CO$_2$H, and —CO$_2$CH$_3$.

The term "benzyl," as used herein, refers to a methyl group on which one of the hydrogen atoms is replaced by a phenyl group, wherein said phenyl group may optionally be substituted with 1 to 5 groups, preferably 1 to 3 groups, OH, OCH$_3$, Cl, F, Br, I, CN, NO$_2$, NH$_2$, N(CH$_3$)H, N(CH$_3$)$_2$, CF$_3$, OCF$_3$, C(=O)CH$_3$, SCH$_3$, S(=O)CH$_3$, S(=O)$_2$CH$_3$, CH$_3$, CH$_2$CH$_3$, CO$_2$H, and CO$_2$CH$_3$.

As used herein, the term "heterocycle," "heterocyclyl," or "heterocyclic group" is intended to mean a stable 3-, 4-, 5-, 6-, or 7-membered monocyclic or bicyclic or 7-, 8-, 9-, 10-, 11-, 12-, 13-, or 14-membered polycyclic heterocyclic ring that is saturated, partially unsaturated, or fully unsaturated, and that contains carbon atoms and 1, 2, 3 or 4 heteroatoms independently selected from the group consisting of N, O and S; and including any polycyclic group in which any of the above-defined heterocyclic rings is fused to a benzene ring. The nitrogen and sulfur heteroatoms may optionally be oxidized (i.e., N→O and S(O)$_p$, wherein p is 0, 1 or 2). The nitrogen atom may be substituted or unsubstituted (i.e., N or NR wherein R is H or another substituent, if defined). The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. When the term "heterocycle" is used, it is intended to include heteroaryl.

Examples of heterocycles include, but are not limited to, acridinyl, azetidinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, imidazolopyridinyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isothiazolopyridinyl, isoxazolyl, isoxazolopyridinyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolopyridinyl, oxazolidinylperimidinyl, oxindolyl, pyrimidinyl, phenanthridinyl, phenanthrolinyl, phenazinyl, phenothiazinyl, phenoxathiinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolopyridinyl, pyrazolyl, pyridazinyl, pyridooxazolyl, pyridoimidazolyl, pyridothiazolyl, pyridinyl, pyrimidinyl, pyrrolidinyl, pyrrolinyl, 2-pyrrolidonyl, 2H-pyrrolyl, pyrrolyl, quinazolinyl, quinolinyl, 4H-quinolizinyl, quinoxalinyl, quinuclidinyl, tetrazolyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thiazolopyridinyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Also included are fused ring and spiro compounds containing, for example, the above heterocycles.

Examples of 5- to 10-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, triazolyl, benzimidazolyl, 1H-indazolyl, benzofuranyl, benzothiofuranyl, benztetrazolyl, benzotriazolyl, benzisoxazolyl, benzoxazolyl, oxindolyl, benzoxazolinyl, benzthiazolyl, benzisothiazolyl, isatinoyl, isoquinolinyl, octahydroisoquinolinyl, tetrahydroisoquinolinyl, tetrahydroquinolinyl, isoxazolopyridinyl, quinazolinyl, quinolinyl, isothiazolopyridinyl, thiazolopyridinyl, oxazolopyridinyl, imidazolopyridinyl, and pyrazolopyridinyl.

Examples of 5- to 6-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, and triazolyl. Also included are fused ring and spiro compounds containing, for example, the above heterocycles.

As used herein, the term "bicyclic heterocycle" or "bicyclic heterocyclic group" is intended to mean a stable 9- or 10-membered heterocyclic ring system which contains two fused rings and consists of carbon atoms and 1, 2, 3, or 4 heteroatoms independently selected from the group consisting of N, O and S. Of the two fused rings, one ring is a 5- or 6-membered monocyclic aromatic ring comprising a 5-membered heteroaryl ring, a 6-membered heteroaryl ring or a benzo ring, each fused to a second ring. The second ring is a 5- or 6-membered monocyclic ring which is saturated, partially unsaturated, or unsaturated, and comprises a 5-membered heterocycle, a 6-membered heterocycle or a carbocycle (provided the first ring is not benzo when the second ring is a carbocycle).

The bicyclic heterocyclic group may be attached to its pendant group at any heteroatom or carbon atom which results in a stable structure. The bicyclic heterocyclic group described herein may be substituted on carbon or on a nitrogen atom if the resulting compound is stable. It is preferred that when the total number of S and O atoms in the heterocycle exceeds 1, then these heteroatoms are not adjacent to one another. It is preferred that the total number of S and O atoms in the heterocycle is not more than 1.

Examples of a bicyclic heterocyclic group are, but not limited to, quinolinyl, isoquinolinyl, phthalazinyl, quinazolinyl, indolyl, isoindolyl, indolinyl, 1H-indazolyl, benzimidazolyl, 1,2,3,4-tetrahydroquinolinyl, 1,2,3,4-tetrahydroisoquinolinyl, 5,6,7,8-tetrahydro-quinolinyl, 2,3-dihydro-benzofuranyl, chromanyl, 1,2,3,4-tetrahydro-quinoxalinyl, and 1,2,3,4-tetrahydro-quinazolinyl.

As used herein, the term "aromatic heterocyclic group" or "heteroaryl" is intended to mean stable monocyclic and polycyclic aromatic hydrocarbons that include at least one heteroatom ring member such as sulfur, oxygen, or nitrogen. Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrroyl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, purinyl, carbazolyl, benzimidazolyl, indolinyl, benzodioxolanyl, and benzodioxane. Heteroaryl groups are substituted or unsubstituted. The nitrogen atom is substituted or unsubstituted (i.e., N or NR wherein R is H or another substituent, if defined). The nitrogen and sulfur heteroatoms may optionally be oxidized (i.e., N→O and S(O)$_p$, wherein p is 0, 1 or 2).

Bridged rings are also included in the definition of heterocycle. A bridged ring occurs when one or more, preferably one to three, atoms (i.e., C, O, N, or S) link two non-adjacent carbon or nitrogen atoms. Examples of bridged rings include, but are not limited to, one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring may also be present on the bridge.

The term "counter ion" is used to represent a negatively charged species such as chloride, bromide, hydroxide, acetate, and sulfate.

When a dotted ring is used within a ring structure, this indicates that the ring structure may be saturated, partially saturated or unsaturated.

substituted with 0-3 R groups, then said group may optionally be substituted with up to three R groups, and at each occurrence R is selected independently from the definition of R. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom in which such substituent is bonded to the rest of the compound of a given formula, then such substituent may be bonded via any atom in such substituent. Combinations of substituents and/or variables are permissible only if such combinations result in stable compounds.

As a person of ordinary skill in the art would be able to understand, a ketone (—CH—C═O) group in a molecule may tautomerize to its enol form (—C═C—OH), as shown in the following equation:

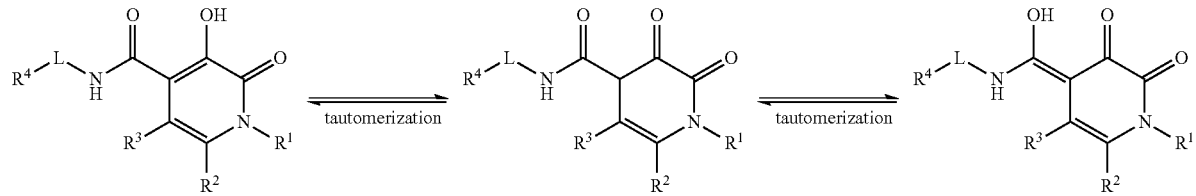

As referred to herein, the term "substituted" means that at least one hydrogen atom is replaced with a non-hydrogen group, provided that normal valencies are maintained and that Likewise, an imine (—CH—C═NHR) group in a molecule may tautomerize to its enamine form (—C═C—NHR), as shown in the following equation:

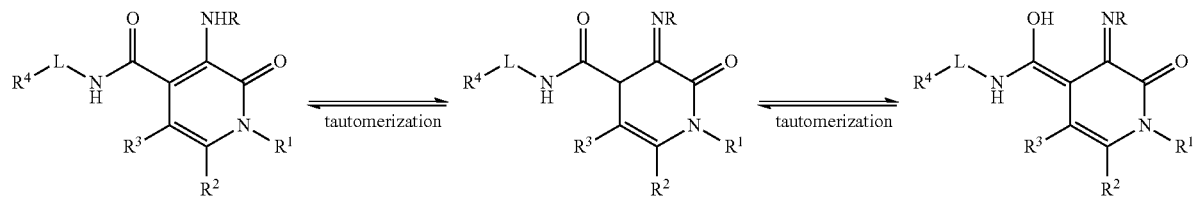

the substitution results in a stable compound. When a substituent is keto (i.e., ═O), then 2 hydrogens on the atom are replaced. Keto substituents are not present on aromatic moieties. When a ring system (e.g., carbocyclic or heterocyclic) is said to be substituted with a carbonyl group or a double bond, it is intended that the carbonyl group or double bond be part (i.e., within) of the ring. Ring double bonds, as used herein, are double bonds that are formed between two adjacent ring atoms (e.g., C═C, C═N, or N═N).

In cases wherein there are nitrogen atoms (e.g., amines) on compounds of the present invention, these may be converted to N-oxides by treatment with an oxidizing agent (e.g., mCPBA and/or hydrogen peroxides) to afford other compounds of this invention. Thus, shown and claimed nitrogen atoms are considered to cover both the shown nitrogen and its N-oxide (N→O) derivative.

When any variable occurs more than one time in any constituent or formula for a compound, its definition at each occurrence is independent of its definition at every other occurrence. Thus, for example, if a group is shown to be Thus, this disclosure is intended to cover all possible tautomers even when a structure depicts only one of them.

The phrase "pharmaceutically acceptable" is employed herein to refer to those compounds, materials, compositions, and/or dosage forms that are, within the scope of sound medical judgment, suitable for use in contact with the tissues of human beings and animals without excessive toxicity, irritation, allergic response, and/or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in *Remington's Pharmaceutical Sciences,* 18th Edition, Mack Publishing Company, Easton, Pa. (1990), the disclosure of which is hereby incorporated by reference.

In addition, compounds of Formula (I), Formula (II), Formula (III), or Formula (IV) may have prodrug forms. Any compound that will be converted in vivo to provide the bioactive agent (i.e., a compound of Formula (I), Formula (II), Formula (III), or Formula (IV)) is a prodrug within the scope and spirit of the invention.

Various forms of prodrugs are well known in the art. For examples of such prodrug derivatives, see:
a) *Design of Prodrugs,* Bundgaard, H., ed., Elsevier (1985), and *Methods in Enzymology,* 112:309-396, Widder, K. et al., eds., Academic Press (1985);
b) Bundgaard, H., Chapter 5, "Design and Application of Prodrugs," *A Textbook of Drug Design and Development,* pp. 113-191, Krosgaard-Larsen, P. et al., eds., Harwood Academic Publishers (1991);
c) Bundgaard, H., *Adv. Drug Deliv. Rev.,* 8:1-38 (1992);
d) Bundgaard, H. et al., *J. Pharm. Sci.,* 77:285 (1988); and
e) Kakeya, N. et al., *Chem. Pharm. Bull.,* 32:692 (1984).

Compounds containing a carboxy group can form physiologically hydrolyzable esters that serve as prodrugs by being hydrolyzed in the body to yield Formula (I), Formula (II), Formula (III), or Formula (IV) compounds per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of Formula (I), Formula (II), Formula (III), or Formula (IV) include $C_1$ to $C_6$ alkyl, $C_1$ to $C_6$ alkylbenzyl, 4-methoxybenzyl, indanyl, phthalyl, methoxymethyl, $C_{1-6}$ alkanoyloxy-$C_{1-6}$ alkyl (e.g., acetoxymethyl, pivaloyloxymethyl or propionyloxymethyl), $C_1$ to $C_6$ alkoxycarbonyloxy-$C_1$ to $C_6$ alkyl (e.g., methoxycarbonyloxymethyl or ethoxycarbonyloxymethyl), glycyloxymethyl, phenylglycyloxymethyl, (5-methyl-2-oxo-1,3-dioxolen-4-yl)-methyl), and other well known physiologically hydrolyzable esters used, for example, in the penicillin and cephalosporin arts. Such esters may be prepared by conventional techniques known in the art.

Preparation of prodrugs is well known in the art and described in, for example, King, F. D., ed., *Medicinal Chemistry: Principles and Practice,* The Royal Society of Chemistry, Cambridge, UK (1994); Testa, B. et al., *Hydrolysis in Drug and Prodrug Metabolism. Chemistry, Biochemistry and Enzymology,* VCHA and Wiley-VCH, Zurich, Switzerland (2003); Wermuth, C. G., ed., *The Practice of Medicinal Chemistry,* Academic Press, San Diego, Calif. (1999).

The present invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds have a variety of potential uses, e.g., as standards and reagents in determining the ability of a potential pharmaceutical compound to bind to target proteins or receptors, or for imaging compounds of this invention bound to biological receptors in vivo or in vitro.

"Stable compound" and "stable structure" are meant to indicate a compound that is sufficiently robust to survive isolation to a useful degree of purity from a reaction mixture, and formulation into an efficacious therapeutic agent. It is preferred that compounds of the present invention do not contain a N-halo, $S(O)_2H$, or $S(O)H$ group.

The term "solvate" means a physical association of a compound of this invention with one or more solvent molecules, whether organic or inorganic. This physical association includes hydrogen bonding. In certain instances the solvate will be capable of isolation, for example when one or more, preferably one to three, solvent molecules are incorporated in the crystal lattice of the crystalline solid. The solvent molecules in the solvate may be present in a regular arrangement and/or a non-ordered arrangement. The solvate may comprise either a stoichiometric or nonstoichiometric amount of the solvent molecules. "Solvate" encompasses both solution-phase and isolable solvates. Exemplary solvates include, but are not limited to, hydrates, ethanolates, methanolates, and isopropanolates. Methods of solvation are generally known in the art.

Abbreviations as used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "µL" for microliter or microliters, "N" for normal, "M" for molar, "nM" for nanomolar, "mol" for mole or moles, "mmol" for millimole or millimoles, "min" for minute or minutes, "h" for hour or hours, "rt" for room temperature, "RT" for retention time, "atm" for atmosphere, "psi" for pounds per square inch, "conc." for concentrate, "sat" or "sat'd" for saturated, "MW" for molecular weight, "mw" for microwave, "mp" for melting point, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "nOe" for nuclear Overhauser effect spectroscopy, "$^1H$" for proton, "δ" for delta, "s" for singlet, "d" for doublet, "t" for triplet, "q" for quartet, "m" for multiplet, "br" for broad, "Hz" for hertz, and "α", "β", "R", "S", "E", and "Z" are stereochemical designations familiar to one skilled in the art.

Me methyl
Et ethyl
Pr propyl
i-Pr isopropyl
Bu butyl i-Bu isobutyl
t-Bu tert-butyl
Ph phenyl
Bn benzyl
Boc tert-butyloxycarbonyl
AcOH or HOAc acetic acid
$AlCl_3$ aluminum chloride
$BBr_3$ boron tribromide
$BCl_3$ boron trichloride
BOP reagent benzotriazol-1-yloxytris(dimethylamino)phosphonium hexafluorophosphate
Cbz carbobenzyloxy
$CH_2Cl_2$ dichloromethane
$CH_3CN$ or ACN acetonitrile
$CDCl_3$ deutero-chloroform
$CDCl_3$ chloroform mCPBA or m-CPBA meta-chloroperbenzoic acid
$Cs_2CO_3$ cesium carbonate
$Cu(OAc)_2$ copper (II) acetate
DCE 1,2 dichloroethane
DCM dichloromethane
DEA diethylamine
DIC or DIPCDI diisopropylcarbodiimide
DIEA, DIPEA or diisopropylethylamine
Hunig's base
DMAP 4-dimethylaminopyridine
DME 1,2-dimethoxyethane
DMF dimethyl formamide
DMSO dimethyl sulfoxide
cDNA complimentary DNA
Dppp (R)-(+)-1,2-bis(diphenylphosphino)propane
EDC N-(3-dimthylaminopropyl)-N'-ethylcarbodiimide
EDTA ethylenediaminetetraacetic acid
$Et_3N$ or TEA triethylamine
EtOAc ethyl acetate
$Et_2O$ diethyl ether
EtOH ethanol
HCl hydrochloric acid
HOBt or HOBT 1-hydroxybenzotriazole
$H_2SO_4$ sulfuric acid
$K_2CO_3$ potassium carbonate
KOAc potassium acetate
$K_3PO_4$ potassium phosphate
LAH lithium aluminum hydride
LG leaving group
LiOH lithium hydroxide
MeOH methanol
$MgSO_4$ magnesium sulfate
MsOH or MSA methylsulfonic acid
NaCl sodium chloride
NaH sodium hydride
$NaHCO_3$ sodium bicarbonate
$Na_2CO_3$ sodium carbonate
NaOH sodium hydroxide
$Na_2SO_3$ sodium sulfite
$Na_2SO_4$ sodium sulfate
$NH_3$ ammonia
$NH_4Cl$ ammonium chloride
$NH_4OH$ ammonium hydroxide
NIS N-iodosuccinimide
OTf triflate or trifluoromethanesulfonate
$Pd_2(dba)_3$ tris(dibenzylideneacetone)dipalladium(0)
$Pd(OAc)_2$ palladium(II) acetate
Pd/C palladium on carbon
$Pd(dppf)Cl_2$ [1,1'-bis(diphenylphosphino)-ferrocene]dichloropalladium(II)
$Ph_3PCl_2$ triphenylphosphine dichloride
PG protecting group
$POCl_3$ phosphorus oxychloride
$PS-Pd(Ph_3)_4$ tetrakis(triphenylphosphine)palladium (0) on polystyrene support
i-PrOH or IPA isopropanol
PS polystyrene
PyBOP (benzotriazol-1-yloxy)tripyrrolidinophosphonium hexafluorophosphate
$SiO_2$ silica oxide
$SnCl_2$ tin(II) chloride
TBAF tetra-n-butylammonium fluoride
TBAI tetra-n-butylammonium iodide
TEA triethylamine
TFA trifluoroacetic acid
THF tetrahydrofuran
$TMSCHN_2$ trimethylsilyldiazomethane Synthesis The compounds of the present invention can be prepared in a number of ways known to one skilled in the art of organic synthesis. The compounds of the present invention can be synthesized using the methods described below, together with synthetic methods known in the art of synthetic organic chemistry, or by variations thereon as appreciated by those skilled in the art. Preferred methods include, but are not limited to, those described below. The reactions are performed in a solvent or solvent mixture appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention.

A particularly useful compendium of synthetic methods which may be applicable to the preparation of compounds of the present invention may be found in Larock, R. C., *Comprehensive Organic Transformations*, VCH, New York (1989). Preferred methods include, but are not limited to, those described below. All references cited herein are hereby incorporated in their entirety herein by reference.

The novel compounds of this invention may be prepared using the reactions and techniques described in this section. Also, in the description of the synthetic methods described below, it is to be understood that all proposed reaction conditions, including choice of solvent, reaction atmosphere, reaction temperature, duration of the experiment and workup procedures, are chosen to be the conditions standard for that reaction, which should be readily recognized by one skilled in the art. Restrictions to the substituents that are compatible with the reaction conditions will be readily apparent to one skilled in the art and alternate methods must then be used.

It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene et al. (*Protective Groups In Organic Synthesis*, Wiley and Sons (1991)).

Compounds of the present invention may be prepared by procedures illustrated in the accompanying schemes.

Scheme 1

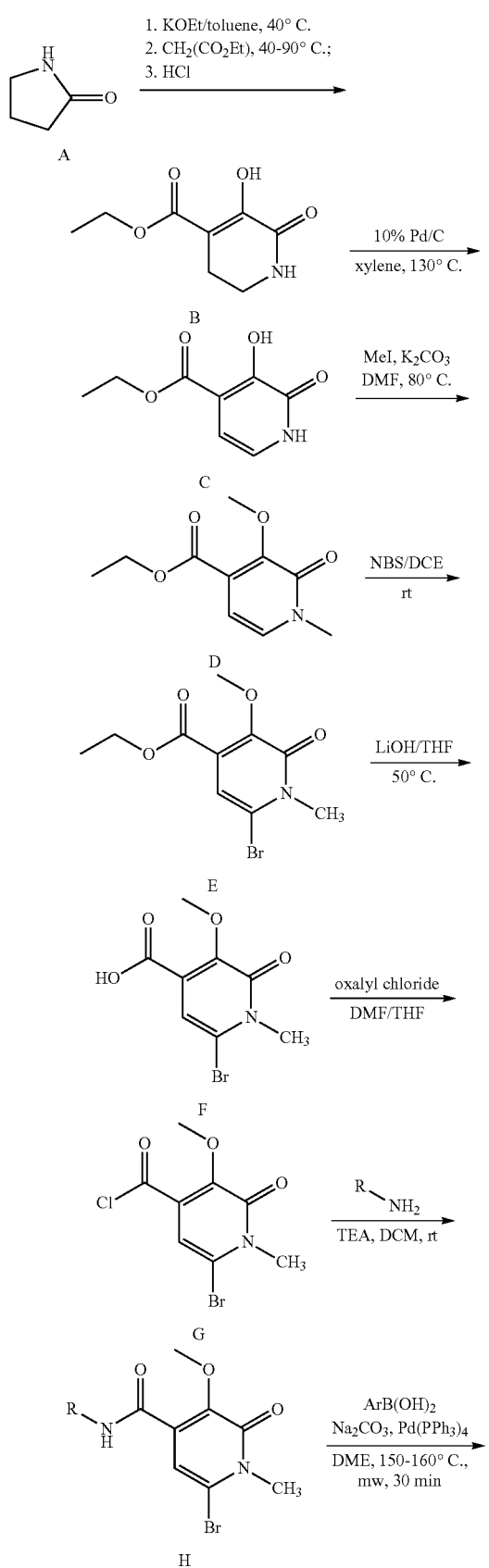

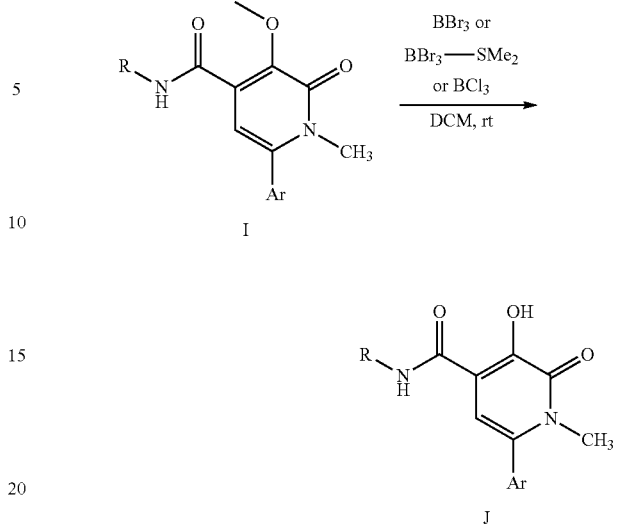

Pyrrolidinone (A) can be treated with a base such as potassium ethoxide and subsequent reaction with diethoxy oxalate followed by decarboxylation of the resulting product can produce the tetrahydropyridinedione (B). The tetrahydropyridinedione (B) can be transformed to the pyridinedione (C) by the treatment with 10% Pd/C in an inert solvent such as xylene. The pyridinedione (C) can be converted to the corresponding dimethylpyridinedione derivative (D) by reacting with a methylating reagent such as methyl iodide in the presence of a base such as potassium carbonate. The pyridinedione derivative (D) can be treated with a brominating agent such as NBS in a solvent such as THF to provide the C6 bromide (E). The resulting ester (E) can be hydrolyzed using an aqueous hydroxide base such as lithium hydroxide or sodium hydroxide with a co-solvent such as THF to give the pyridinedione carboxylic acid (F). The carboxylic acid (F) can be converted to the acid chloride (G) by the treatment with oxalyl chloride in the presence of a catalytic amount of DMF in a solvent such as THF. The acid chloride (G) can be converted to the amide (H) by the treatment with an amine (RNH2) in the presence of a base such as TEA in a solvent such as DCM. The resulting pyridinedione bromide (H) can be converted to the corresponding aryl pyridinedione (I) by reacting with a boronic acid in the presence of a catalyst like tetrakis(triphenylphosphine)palladium and sodium carbonate in an organic solvent such as DME. The methoxy group on the amide (I) could be cleaved using boron tribromide-methyl sulfide complex, boron tribromide solution in dichloromethane or boron trichloride to provide the pyridinedione (J).

Scheme 2

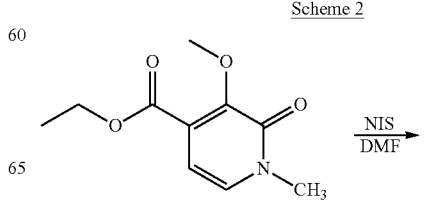

33

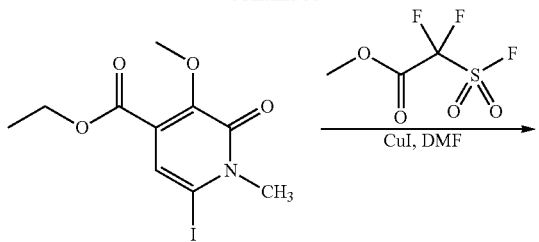

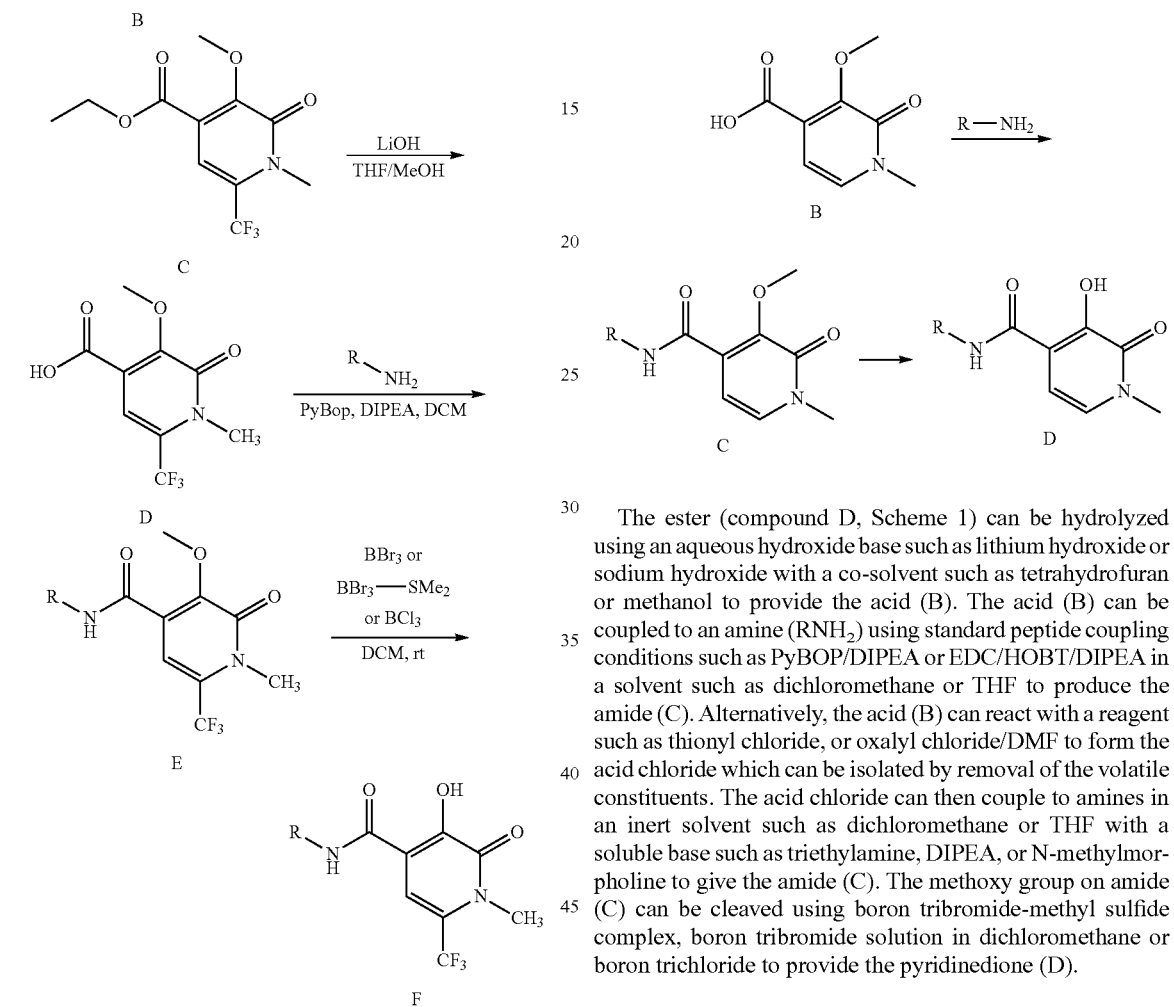

The ester (compound D, Scheme 1) can be treated with NIS in DMF to provide the C6 iodide (B). The resulting iodide (B) can be converted to trifluoromethylpyridinedione (C) by the treatment with methyl 2,2-difluoro-2-(fluorosulfonyl)acetate in the presence of copper (I) iodide in a solvent such as DMF. The ester (C) can be hydrolyzed using an aqueous hydroxide base such as lithium hydroxide or sodium hydroxide with a co-solvent such as tetrahydrofuran or methanol to provide the acid (D). The acid (D) can be coupled to an amine (RNH2) using standard peptide coupling conditions such as PyBOP/DIPEA or EDC/HOBT/DIPEA in a solvent such as dichloromethane or THF to produce the amide (E). The methoxy group on amide (E) could be cleaved using boron tribromide-methyl sulfide complex, boron tribromide solution in dichloromethane or boron trichloride to provide the pyridinedione (F).

34

The ester (compound D, Scheme 1) can be hydrolyzed using an aqueous hydroxide base such as lithium hydroxide or sodium hydroxide with a co-solvent such as tetrahydrofuran or methanol to provide the acid (B). The acid (B) can be coupled to an amine (RNH$_2$) using standard peptide coupling conditions such as PyBOP/DIPEA or EDC/HOBT/DIPEA in a solvent such as dichloromethane or THF to produce the amide (C). Alternatively, the acid (B) can react with a reagent such as thionyl chloride, or oxalyl chloride/DMF to form the acid chloride which can be isolated by removal of the volatile constituents. The acid chloride can then couple to amines in an inert solvent such as dichloromethane or THF with a soluble base such as triethylamine, DIPEA, or N-methylmorpholine to give the amide (C). The methoxy group on amide (C) can be cleaved using boron tribromide-methyl sulfide complex, boron tribromide solution in dichloromethane or boron trichloride to provide the pyridinedione (D).

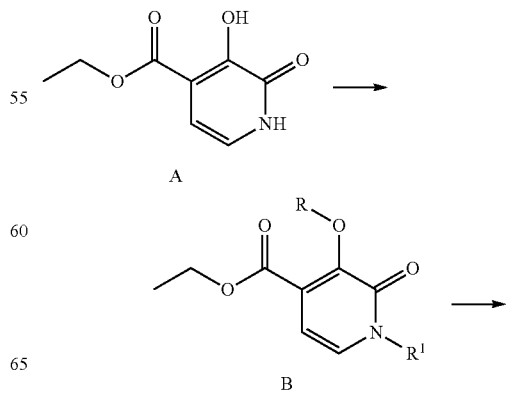

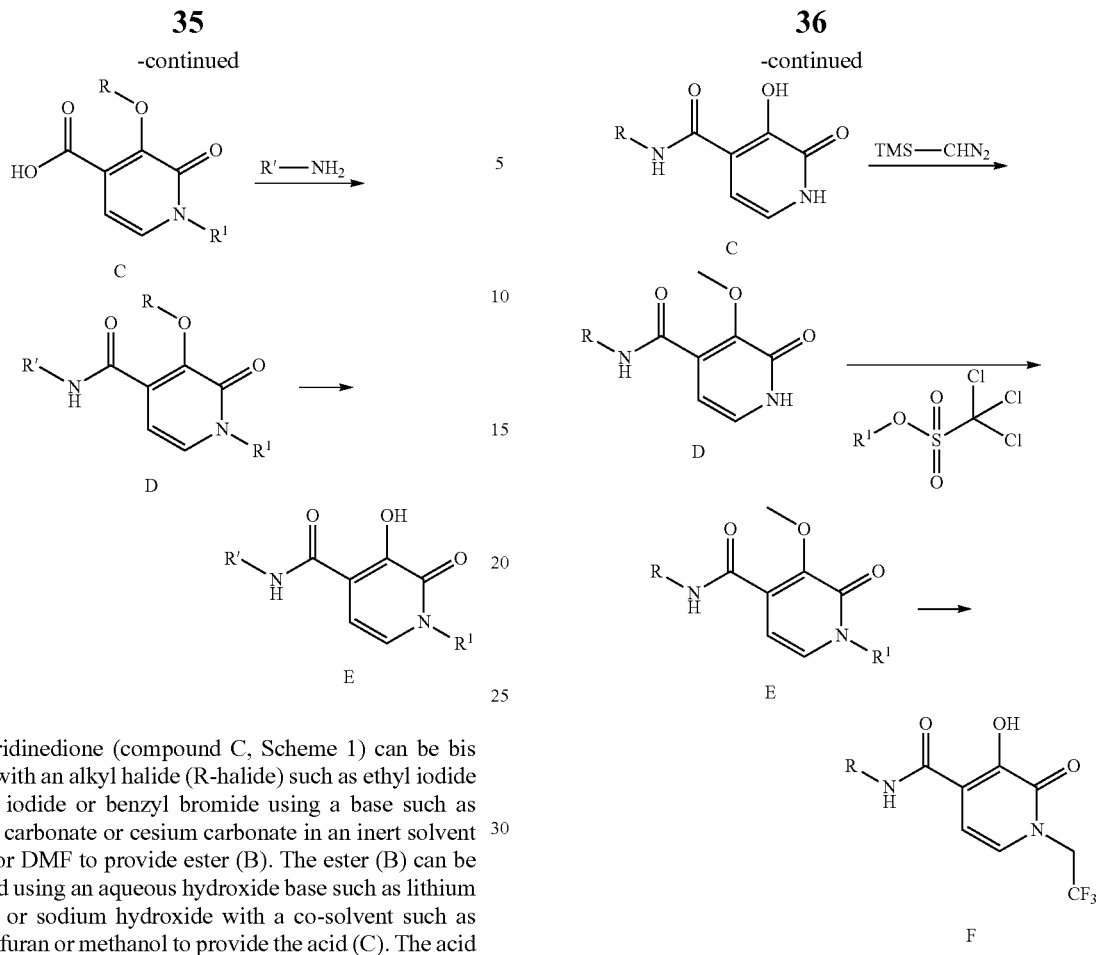

The pyridinedione (compound C, Scheme 1) can be bis alkylated with an alkyl halide (R-halide) such as ethyl iodide or methyl iodide or benzyl bromide using a base such as potassium carbonate or cesium carbonate in an inert solvent like THF or DMF to provide ester (B). The ester (B) can be hydrolyzed using an aqueous hydroxide base such as lithium hydroxide or sodium hydroxide with a co-solvent such as tetrahydrofuran or methanol to provide the acid (C). The acid (C) can be coupled to an amine (R'NH$_2$) using standard peptide coupling conditions such as PyBOP/DIPEA or EDC/HOBT/DIPEA in a solvent such as dichloromethane or THF to produce the amide (D). Alternatively, the acid (C) can react with a reagent such as thionyl chloride, or oxalyl chloride/DMF to form the acid chloride which can be isolated by removal of the volatile constituents. The acid chloride can then couple to amines (R'NH$_2$) in an inert solvent such as dichloromethane or THF with a soluble base such as triethylamine, DIPEA, or N-methylmorpholine to give the amide (D). The alkoxy group on amide (D) could be cleaved using boron tribromide-methyl sulfide complex, boron tribromide solution in dichloromethane or boron trichloride to provide the pyridinedione (E).

Pyridinedione (Compound C, Scheme 1) can be hydrolyzed to the corresponding acid and the resulting acid reacted with a reagent such as thionyl chloride, or oxalyl chloride/DMF to form the acid chloride (B) which can be isolated by removal of the volatile constituents. The acid chloride can then couple to amines (RNH$_2$) in an inert solvent such as dichloromethane or THF with a soluble base such as triethylamine, DIPEA, or N-methylmorpholine to give the amide (C). The amide (C) can be converted with TMS-diazomethane in inert solvent like THF or acetonitrile to compound (D). Compound (D) can be treated with a trichloromethanesulfonate using a base such as cesium carbonate or potassium carbonate in an inert solvent such as dichloromethane or THF to provide the N1-substituted compound (E). The methoxy group on compound (E) can be cleaved using boron trichloride-methyl sulfide complex, boron tribromide solution in dichloromethane or boron trichloride to provide the pyridinedione (F).

Scheme 5

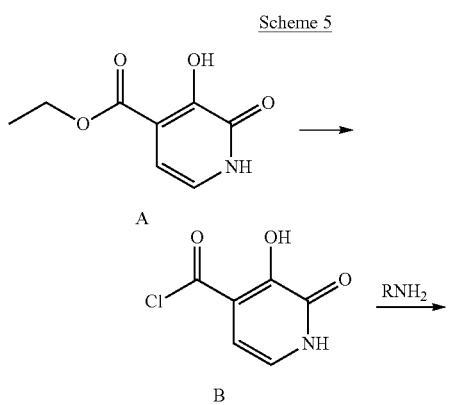

Scheme 6

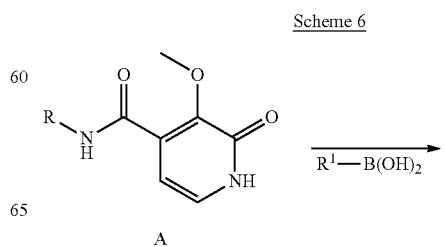

-continued

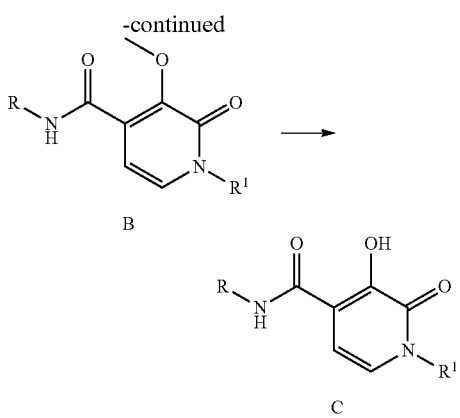

The pyridinedione (Compound D, Scheme 5) can be coupled with and organoboronic acid ($R^1B(OH)_2$) using copper (I) acetate in an inert solvent like THF or dichloromethane to provide compound (B). The methoxy group on compound (B) could be cleaved using boron trichloride-methyl sulfide complex, boron tribromide solution in dichloromethane or boron trichloride to provide the pyridinedione (C).

Scheme 7

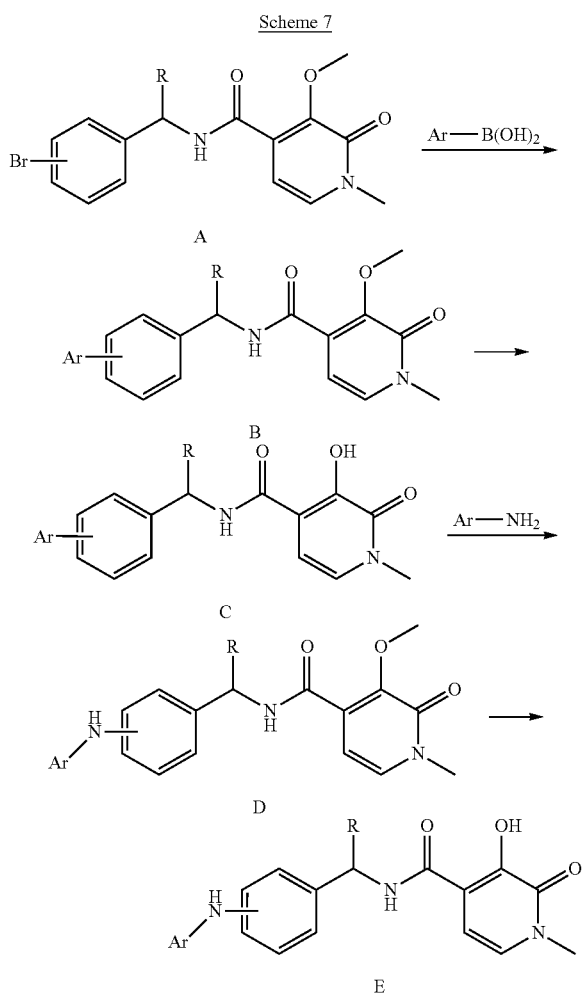

The bromide (A) can be treated with an aryl boronic acid ($ArB(OH)_2$) using a base such as sodium carbonate and a catalyst such as tetrakistriphenylphosphine palladium in a solvent such as DME to provide the product (B). The methoxy group on compound (B) can be cleaved using boron tribromide-methyl sulfide complex, boron tribromide solution in dichloromethane or boron trichloride to provide the pyridinedione (C). The bromide (A) can also be treated with an arylamine ($ArNH_2$) using a base such as sodium t-butoxide and a catalyst such as tris(dibenzylideneacetone)dipalladium and BINAP in a solvent such as toluene to provide the product (D). The methoxy group on compound (D) can be cleaved using boron tribromide-methyl sulfide complex, boron tribromide solution in dichloromethane or boron trichloride to provide the pyridinedione (E).

General Methods

The following methods were used in the exemplified Examples, except where noted otherwise.

Analytical HPLC and LC/MS Methods Employed in Characterization of Examples

Reverse phase analytical HPLC/MS was performed on Shimadzu LC10AS systems coupled with Waters ZMD Mass Spectrometers (Methods A-C, E and F) or Waters Aquity system coupled with a Waters Micromass ZQ Mass Spectrometer (Method D). Chiral analytical LC was performed on a Berger Analytical SFC instrument (Method G).

Method A: Linear gradient of 0 to 100% B over 4 min, with 1 min hold at 100% B;
  UV visualization at 220 nm
  Column: Phenomenex Luna C18 4.6×50 mm
  Flow rate: 4 mL/min
Solvent A: 0.1% trifluoroacetic acid, 90% water, 10% acetonitrile
Solvent B: 0.1% trifluoroacetic acid, 90% acetonitrile, 10% water.

Method B: Linear gradient of 0 to 100% B over 4 min, with 1 min hold at 100% B;
  UV visualization at 220 nm
  Column: Phenomenex Luna C18 4.6×50 mm
  Flow rate: 4 mL/min
Solvent A: 10 mM ammonium acetate, 90% water, 10% acetonitrile
Solvent B: 10 mM ammonium acetate, 90% acetonitrile, 10% water.

Method C: Linear gradient of 0 to 100% B over 4 min, with 1 min hold at 100% B;
  UV visualization at 220 nm
  Column: Phenomenex Luna C18 4.6×50 mm
  Flow rate: 4 mL/min
Solvent A: 0.1% trifluoroacetic acid, 90% water, 10% methanol
Solvent B: 0.1% trifluoroacetic acid, 90% methanol, 10% water.

Method D: Linear gradient of 0 to 100% B over 2 min, with 1 min hold at 100% B;
  UV visualization at 220 nm
  Column: Phenomenex Luna C18 2.0×30 mm
  Flow rate: 1 mL/min
Solvent A: 0.1% trifluoroacetic acid, 90% water, 10% methanol
Solvent B: 0.1% trifluoroacetic acid, 90% methanol, 10% water.

Method E: Linear gradient of 2 to 98% B over 1 min, with 0.5 min hold time at 98% B;
  UV visualization at 220 nm
  Column. Waters BEH C18 2.1×50 mm
  Flow rate: 0.8 mL/min
Solvent A: 0.05% TFA, 100% water
Solvent B: 0.05% TFA, 100% CAN Method F: Linear gradient of 0 to 100% B over 4 min, with 1 min hold at 100% B;
  UV visualization at 220 nm
  Column. Mac-Mod Halo C18, 4.6×50 mm
  Flow rate: 4 mL/min
Solvent A: 10 mM ammonium acetate, 95% water, 5% ACN
Solvent B: 10 mM ammonium acetate, 95% ACN, 5% water
Preparative HPLC Methods Employed in the Purification of Products
Method I: Linear gradient of 0 to 100% B over 10 min, with 5 min hold time at 100% B
  Shimadzu LC-8A binary pumps
  Waters ZQ mass specrometer using Waters Masslynx 4.0 SP4 MS software
  UV visualization at 220 nm
  Column: Waters SunFire 19×100 mm 5 µm C18
  Flow rate: 20 mL/min
  Peak collection triggered by mass spectrometry
Solvent A: 0.1% TFA, 10% ACN, 90% water
Solvent B: 0.1% TFA, 90% ACN, 10% water
Method J: Linear gradient of 20 to 100% B over 10 min, with 5 min hold time at 100% B
  Shimadzu LC-8A binary pumps
  Shimadzu SPD-20A UV detector
  UV visualization at 220 nm
  Column: Phenomenex Luna AXIA 21.1×100 mm 5 µm C18
  Flow rate: 20 mL/min
  Peak collection triggered by UV absorbance
Solvent A: 0.1% TFA, 10% MeOH, 90% water
Solvent B: 0.1% TFA, 90% MeOH, 10% water
Method K: Linear gradient of 20 to 100% B over 10 min, with 2 min hold time at 100% B
  Shimadzu LC-8A binary pumps
  Shimadzu SPD-10A UV detector
  UV visualization at 220 nm
  Column: Phenomenex Luna AXIA 21.1×100 mm 5 µm C18
  Flow rate: 20 mL/min
  Peak collection triggered by UV absorbance
Solvent A: 0.1% TFA, 10% ACN, 90% water
Solvent B: 0.1% TFA, 90% ACN, 10% water
Method L: Linear gradient of 20 to 100% B over 10 min, with 2 min hold time at 100% B
  Shimadzu LC-8A binary pumps
  Shimadzu SPD-10A UV detector
  UV visualization at 220 nm
  Column: YMC Sunfire, 5 µm, C18 column, 30×100 mm
  Flow rate: 40 mL/min
  Peak collection triggered by UV absorbance
  Solvent A: 0.1% TFA, 10% MeOH, 90% water
  Solvent B: 0.1% TFA, 90% MeOH, 10% water
  Method M: Linear gradient of 20 to 55% B over 20 min;
  UV visualization at 220 nm;
  Column. Axia Luna 5 µm C18 30×100 mm;
  Flow rate: 40 mL/min;
  Solvent A: 0.1% TFA, 10% ACN, 90% water;
  Solvent B: 0.1% TFA, 90% ACN, 10% water.
Method N: Linear gradient of 20 to 100% B over 20 min, with 2 min hold time at 100% B
  UV visualization at 220 nm;
  Column. Axia Luna 5 µm C18 30×100 mm;
  Flow rate: 40 mL/min;
  Solvent A: 0.1% TFA, 10% ACN, 90% water;
  Solvent B: 0.1% TFA, 90% ACN, 10% water.

NMR Employed in Characterization of Examples $^1$H NMR spectra were obtained with Bruker or JEOL fourier transform spectrometers operating at frequencies as follows: $^1$H NMR: 400 MHz (Bruker or JEOL) or 500 MHz (JEOL). $^{13}$C NMR: 100 MHz (Bruker or JEOL). Spectra data are reported in the format: chemical shift (multiplicity, coupling constants, number of hydrogens). Chemical shifts are specified in ppm downfield of a tetramethylsilane internal standard (δ units, tetramethylsilane=0 ppm) and/or referenced to solvent peaks, which in $^1$H NMR spectra appear at 2.49 ppm for $CD_2HSOCD_3$, 3.30 ppm for $CD_2HOD$, and 7.24 ppm for $CHCl_3$, and which in $^{13}$C NMR spectra appear at 39.7 ppm for $CD_3SOCD_3$, 49.0 ppm for $CD_3OD$, and 77.0 ppm for $CDCl_3$. All $^{13}$C NMR spectra were proton decoupled.

Biology

The endothelium occupies a pivotal position at the interface between the circulating humoral and cellular elements of the blood, and the solid tissues which constitute the various organs. In this unique position, endothelial cells regulate a large number of critical processes, including leukocyte adherence and transit through the blood vessel wall, local control of blood vessel tone, modulation of the immune response, the balance between thrombosis and thrombolysis, and new blood vessel development. Thus, endothelial cell dysfunction has been postulated as a central feature of vascular diseases such as hypertension and atherosclerosis. (WO 1999/032611 and references cited therein, e.g., Folkman et al., *Science*, 235:442-447 (1987); Yanagisawa et al., *Nature*, 332:411-415 (1988); Folkman et al., *J. Biol. Chem.*, 267:10931-10934 (1992); Janssens et al., *J. Biol. Chem.*, 267:14519-14522 (1992); Lamas et al., *Proc. Natl. Acad. Sci. U.S.A.*, 89:6348-6352 (1992); Luscher et al., *Hypertension*, 19:117-130 (1992); Williams et al., *Am. Rev. Respir. Dis.*, 146:S45-S50 (1992); and Bevilacqua et al., *J. Clin. Invest.*, 91:379-387 (1993)).

Atherosclerosis and its associated coronary artery disease (CAD) is the leading cause of mortality in the industrialized world. Despite attempts to modify secondary risk factors (smoking, obesity, lack of exercise) and treatment of dyslipidemia with dietary modification and drug therapy, coronary heart disease (CHD) remains the most common cause of death in the U.S., where cardiovascular disease accounts for 44% of all deaths, with 53% of these associated with atherosclerotic coronary heart disease.

Risk for development of atherosclerosis has been shown to be strongly correlated with certain plasma lipid levels. While elevated low density lipoprotein-cholesterol (LDL-C) may be the most recognized form of dyslipidemia, it is by no means the only significant lipid associated contributor to CHD. Low high density lipoprotein-cholesterol (HDL-C) is also a known risk factor for CHD (Gordon, D. J. et al., *Circulation*, 79:8-15 (1989)).

High LDL-C and triglyceride levels are positively correlated, while high levels of HDL-C are negatively correlated with the risk for developing cardiovascular diseases. Thus, dyslipidemia is not a unitary risk profile for CHD but may be comprised of one or more, preferably one to three, lipid aberrations.

At least 50% of the variation in HDL cholesterol levels is genetically determined. The phenotype of elevated HDL cholesterol is often dominantly inherited, but homozygous deficiency of HL or of the cholesteryl ester transfer protein (CETP), which result in elevated HDL cholesterol, are recessive conditions. Recently, several genetic variations in the human endothelial lipase gene have been identified, six of which potentially produce functional variants of the protein, and the frequencies of these variants were found to be associated with elevated levels of HDL cholesterol in human subjects (deLemos et al., *Circulation*, 106:1321-1326 (2002)). Notably, the endothelial lipase-mediated binding and uptake of HDL particles and the selective uptake of HDL-derived cholesterol esters have been reported to be independent of its enzymatic lipolytic activity (Strauss et al., *Biochem. J.*, 368:69-79 (2002)).

Because of the beneficial effects widely associated with elevated HDL levels, an agent which inhibits EL activity in humans, by virtue of its HDL increasing ability, are expected to be useful for the treatment, prevention, the arrestment and/or regression of atherosclerosis, coronary heart disease, cerebrovascular disorders etc., especially those (but not restricted thereto) which are characterized by one or more of the following factors: (a) high plasma triglyceride concentrations, high postprandial plasma triglyceride concentrations; (b) low HDL cholesterol concentration; (c) low apoA lipoprotein concentrations; (d) high LDL cholesterol concentrations; (e) small dense LDL cholesterol particles; and (f) high apoB lipoprotein concentrations.

The term "modulator" refers to a chemical compound with capacity to either enhance (e.g., "agonist" activity) or partially enhance (e.g., "partial agonist" activity) or inhibit (e.g., "antagonist" activity or "inverse agonist" activity) a functional property of biological activity or process (e.g., enzyme activity or receptor binding); such enhancement or inhibition may be contingent on the occurrence of a specific event, such as activation of a signal transduction pathway, receptor internalization, and/or may be manifest only in particular cell types.

It is also desirable and preferable to find compounds with advantageous and improved characteristics compared with known anti-atherosclerosis agents, in one or more of the following categories that are given as examples, and are not intended to be limiting: (a) pharmacokinetic properties, including oral bioavailability, half life, and clearance; (b) pharmaceutical properties; (c) dosage requirements; (d) factors that decrease blood drug concentration peak-to-trough characteristics; (e) factors that increase the concentration of active drug at the receptor; (f) factors that decrease the liability for clinical drug-drug interactions; (g) factors that decrease the potential for adverse side-effects, including selectivity versus other biological targets; and (h) improved therapeutic index.

As used herein, the term "patient" encompasses all mammalian species.

As used herein, the term "subject" refers to any human or non-human organism that could potentially benefit from treatment with an anti-atherosclerosis agent, e.g., an endothelial lipase inhibitor. Exemplary subjects include human beings of any age with risk factors for atherosclerosis and its associated coronary artery disease. Common risk factors include, but are not limited to, age, sex, weight, and family history.

As used herein, "treating" or "treatment" cover the treatment of a disease-state in a mammal, particularly in a human, and include: (a) inhibiting the disease-state, i.e., arresting it development; and/or (b) relieving the disease-state, i.e., causing regression of the disease state.

As used herein, "prophylaxis" or "prevention" covers the preventive treatment of a subclinical disease-state in a mammal, particularly in a human, aimed at reducing the probability of the occurrence of a clinical disease-state. Patients are selected for preventative therapy based on factors that are known to increase risk of suffering a clinical disease state compared to the general population. "Prophylaxis" therapies can be divided into (a) primary prevention and (b) secondary prevention. Primary prevention is defined as treatment in a subject that has not yet presented with a clinical disease state, whereas secondary prevention is defined as preventing a second occurrence of the same or similar clinical disease state.

As used herein, "risk reduction" covers therapies that lower the incidence of development of a clinical disease state. As such, primary and secondary prevention therapies are examples of risk reduction.

"Therapeutically effective amount" is intended to include an amount of a compound of the present invention that is effective when administered alone or in combination to inhibit endothelial lipase and/or to prevent or treat the disorders listed herein. When applied to a combination, the term refers to combined amounts of the active ingredients that result in the preventive or therapeutic effect, whether administered in combination, serially, or simultaneously.

Biological Activity

Endothelial lipase activity was measured using a fluorescent substrate, A10070, (Invitrogen, CA) doped into an artificial vesicle containing DMPG (Avanti Polar Lipids) as the excipient. Vesicles were prepared by combining 285 uL of 1 mM DMPG in a 1:1 mixture of MeOH and $CHCl_3$ with 15 uL of 1 mM A10070 in a 1:1 mixture of MeOH and $CHCl_3$. The mixture was dried under nitrogen and resuspended in 150 uL of 50 mM HEPES pH 8.0 buffer containing 100 mM NaCl and 0.2 mM EDTA. The sample was allowed to sit at rt for 15 min and then was sonicated 3×4 mins on ice with a Branson Sonicator using duty cycle 1. This preparation provides vesicles with a mole fraction of 0.05 for the FRET substrate.

The enzymatic assay was measured using white, opaque 96-well half area plates. Each well contained 60 uL of assay buffer (50 mM HEPES pH 8.0, 50 mM NaCl and 1 mM $CaCl_2$) and 2 ul of a DMSO solution containing compound of interest. Conditioned media obtained from HT-1080 cells, which were transformed by RAGE technology (Athersys) to overexpress endogenous EL, was added and the reaction was allowed to incubate for 20 min at 37° C. with gentle agitation. The reaction was started by the addition of 20 uL of a 1:4 dilution of vesicles. The final total reaction volume was 100 uL. The reaction rates were measured on a Gemini plate reader with an excitation wavelength of 488 nm and a emission of 530 nm. Readings were taken every 20 seconds for 10 min with agitation between each reading. The slope of the linear portion of the readout was used to calculate the rate of the reaction.

The exemplified examples disclosed in the present invention were tested in the EL assay described above and found having EL inhibitory activity. The EL $IC_{50}$ values measured for the following examples are listed in Table 1.

TABLE 1

| Ex. No. | HLE_EL_CRC $IC_{50}$ (nM) |
|---|---|
| 16 | 10.00 |
| 21 | 17.92 |
| 29 | 6545.00 |
| 31 | 6453.00 |
| 32 | 11.27 |
| 33 | 4571.00 |
| 37 | 352.00 |
| 39 | 691.80 |
| 41 | 11.06 |
| 44 | 475.10 |

Accordingly, the compounds of the present invention can be administered to mammals, preferably humans, for the treatment of a variety of conditions and disorders, including, but not limited to, atherosclerosis, coronary heart disease, coronary artery disease, coronary vascular disease, cerebrovascular disorders, Alzheimer's disease, venous thrombosis, peripheral vascular disease, dyslipidemia, hyperbetalipoproteinemia, hypoalphalipoproteinemia, hypercholesterolemia, hypertriglyceridemia, familial-hypercholesterolemia, cardiovascular disorders, angina, ischemia, cardiac ischemia, stroke, myocardial infarction, reperfusion injury, angioplastic restenosis, hypertension, vascular complications of diabetes, obesity or endotoxemia.

VI. Pharmaceutical Compositions, Formulations and Combinations

The compounds of this invention can be administered for any of the uses described herein by any suitable means, for example, orally, such as tablets, capsules (each of which includes sustained release or timed release formulations), pills, powders, granules, elixirs, tinctures, suspensions, syrups, and emulsions; sublingually; bucally; parenterally, such as by subcutaneous, intravenous, intramuscular, or intrasternal injection, or infusion techniques (e.g., as sterile injectable aqueous or non-aqueous solutions or suspensions); nasally, including administration to the nasal membranes, such as by inhalation spray; topically, such as in the form of a cream or ointment; or rectally such as in the form of suppositories. They can be administered alone, but generally will be administered with a pharmaceutical carrier selected on the basis of the chosen route of administration and standard pharmaceutical practice.

The term "pharmaceutical composition" means a composition comprising a compound of the invention in combination with at least one additional pharmaceutically acceptable carrier. A "pharmaceutically acceptable carrier" refers to media generally accepted in the art for the delivery of biologically active agents to animals, in particular, mammals, including, i.e., adjuvant, excipient or vehicle, such as diluents, preserving agents, fillers, flow regulating agents, disintegrating agents, wetting agents, emulsifying agents, suspending agents, sweetening agents, flavoring agents, perfuming agents, anti-bacterial agents, anti-fungal agents, lubricating agents and dispensing agents, depending on the nature of the mode of administration and dosage forms. Pharmaceutically acceptable carriers are formulated according to a number of factors well within the purview of those of ordinary skill in the art. These include, without limitation: the type and nature of the active agent being formulated; the subject to which the agent-containing composition is to be administered; the intended route of administration of the composition; and the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, *Remington's Pharmaceutical Sciences*, 18th Edition (1990).

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired.

By way of general guidance, the daily oral dosage of each active ingredient, when used for the indicated effects, will range between about 0.01 to about 5000 mg per day, preferably between about 0.1 to about 1000 mg per day, and most preferably between about 0.1 to about 250 mg per day. Intravenously, the most preferred doses will range from about 0.01 to about 10 mg/kg/minute during a constant rate infusion. Compounds of this invention may be administered in a single daily dose, or the total daily dosage may be administered in divided doses of two, three, or four times daily.

The compounds are typically administered in admixture with suitable pharmaceutical diluents, excipients, or carriers (collectively referred to herein as pharmaceutical carriers) suitably selected with respect to the intended form of administration, e.g., oral tablets, capsules, elixirs, and syrups, and consistent with conventional pharmaceutical practices.

Dosage forms (pharmaceutical compositions) suitable for administration may contain from about 1 milligram to about 2000 milligrams of active ingredient per dosage unit. In these pharmaceutical compositions the active ingredient will ordinarily be present in an amount of about 0.1-95% by weight based on the total weight of the composition.

A typical capsule for oral administration contains at least one of the compounds of the present invention (250 mg), lactose (75 mg), and magnesium stearate (15 mg). The mixture is passed through a 60 mesh sieve and packed into a No. 1 gelatin capsule.

A typical injectable preparation is produced by aseptically placing at least one of the compounds of the present invention (250 mg) into a vial, aseptically freeze-drying and sealing. For use, the contents of the vial are mixed with 2 mL of physiological saline, to produce an injectable preparation.

The present invention includes within its scope pharmaceutical compositions comprising, as an active ingredient, a therapeutically effective amount of at least one of the compounds of the present invention, alone or in combination with a pharmaceutical carrier. Optionally, compounds of the present invention can be used alone, in combination with other compounds of the invention, or in combination with one or more, preferably one to three, other therapeutic agent(s), e.g., HMG-CoA reductase inhibitors or other pharmaceutically active material.

The compounds of the present invention may be employed in combination with other EL inhibitors or one or more, preferably one to three, other suitable therapeutic agents useful in the treatment of the aforementioned disorders including: anti-atherosclerotic agents, anti-dyslipidemic agents, anti-diabetic agents, anti-hyperglycemic agents, anti-hyperinsulinemic agents, anti-thrombotic agents, anti-retinopathic agents, anti-neuropathic agents, anti-nephropathic agents, anti-ischemic agents, anti-hypertensive agents, anti-obesity agents, anti-hyperlipidemic agents, anti-hypertriglyceridemic agents, anti-hypercholesterolemic agents, anti-restenotic agents, anti-pancreatic agents, lipid lowering agents, anorectic agents, memory enhancing agents, anti-dementia agents, cognition promoting agents, appetite suppressants, treatments for heart failure, treatments for peripheral arterial disease, treatment for malignant tumors, and anti-inflammatory agents.

The compounds of the present invention may be employed in combination with additional therapeutic agent(s) selected from one or more, preferably one to three, of the following therapeutic agents in treating atherosclerosis: anti-hyperlipidemic agents, plasma HDL-raising agents, anti-hypercholesterolemic agents, cholesterol biosynthesis inhibitors (such as HMG CoA reductase inhibitors), acyl-coenzyme A:cholesterol acytransferase (ACAT) inhibitors, LXR agonist, probucol, raloxifene, nicotinic acid, niacinamide, cholesterol absorption inhibitors, bile acid sequestrants (such as anion exchange resins, or quaternary amines (e.g., cholestyramine or colestipol)), low density lipoprotein receptor inducers, clofibrate, fenofibrate, benzofibrate, cipofibrate, gemfibrizol, vitamin $B_6$, vitamin $B_{12}$, anti-oxidant vitamins, β-blockers, anti-diabetes agents, angiotensin II antagonists, angiotensin converting enzyme inhibitors, platelet aggregation inhibitors, fibrinogen receptor antagonists, aspirin or fibric acid derivatives.

The compounds of the present invention may be employed in combination with additional therapeutic agent(s) selected from one or more, preferably one to three, of the following therapeutic agents in treating cholesterol biosynthesis inhibitor, particularly an HMG-CoA reductase inhibitor. Examples of suitable HMG-CoA reductase inhibitors include, but are not limited to, lovastatin, simvastatin, pravastatin, fluvastatin, atorvastatin, and rivastatin.

The term HMG-CoA reductase inhibitor is intended to include all pharmaceutically acceptable salt, ester, free acid and lactone forms of compounds which have HMG-CoA reductase inhibitory activity and, therefore, the use of such salts, esters, free acids and lactone forms is included within the scope of this invention. Compounds which have inhibitory activity for HMG-CoA reductase can be readily identified using assays well-known in the art.

The compounds of the invention may be used in combination with one or more, preferably one to three, of the following anti-diabetic agents depending on the desired target therapy. Studies indicate that diabetes and hyperlipidemia modulation can be further improved by the addition of a second agent to the therapeutic regimen. Examples of anti-diabetic agents include, but are not limited to, sulfonylureas (such as chlorpropamide, tolbutamide, acetohexamide, tolazamide, glyburide, gliclazide, glynase, glimepiride, and glipizide), biguanides (such as metformin), thiazolidinediones (such as ciglitazone, pioglitazone, troglitazone, and rosiglitazone), and related insulin sensitizers, such as selective and non-selective activators of PPARα, PPARβ and PPARγ; dehydroepiandrosterone (also referred to as DHEA or its conjugated sulphate ester, DHEA-$SO_4$); anti-glucocorticoids; TNFα inhibitors; α-glucosidase inhibitors (such as acarbose, miglitol, and voglibose), pramlintide (a synthetic analog of the human hormone amylin), other insulin secretagogues (such as repaglinide, gliquidone, and nateglinide), insulin, as well as the therapeutic agents discussed above for treating atherosclerosis.

The compounds of the invention may be used in combination with one or more, preferably one to three, of the following anti-obesity agents selected from phenylpropanolamine, phentermine, diethylpropion, mazindol, fenfluramine, dexfenfluramine, phentiramine, $β_3$-adrenoreceptor agonist agents; sibutramine, gastrointestinal lipase inhibitors (such as orlistat), and leptins. Other agents used in treating obesity or obesity-related disorders include neuropeptide Y, enterostatin, cholecytokinin, bombesin, amylin, histamine $H_3$ receptors, dopamine $D_2$ receptor modulators, melanocyte stimulating hormone, corticotrophin releasing factor, galanin and gamma amino butyric acid (GABA).

The above other therapeutic agents, when employed in combination with the compounds of the present invention may be used, for example, in those amounts indicated in the *Physicians' Desk Reference*, as in the patents set out above, or as otherwise determined by one of ordinary skill in the art.

Particularly when provided as a single dosage unit, the potential exists for a chemical interaction between the combined active ingredients. For this reason, when the compound of the present invention and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material that affects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low viscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

The compounds of the present invention can be administered alone or in combination with one or more, preferably one to three, additional therapeutic agents. By "administered in combination" or "combination therapy" it is meant that the compound of the present invention and one or more, preferably one to three, additional therapeutic agents are administered concurrently to the mammal being treated. When administered in combination, each component may be administered at the same time or sequentially in any order at different points in time. Thus, each component may be administered separately but sufficiently closely in time so as to provide the desired therapeutic effect.

The compounds of the present invention are also useful as standard or reference compounds, for example as a quality standard or control, in tests or assays involving the endothelial lipase. Such compounds may be provided in a commercial kit, for example, for use in pharmaceutical research involving endothelial lipase or HDL activity. For example, a compound of the present invention could be used as a reference in an assay to compare its known activity to a compound with an unknown activity. This would ensure the experimenter that the assay was being performed properly and provide a basis for comparison, especially if the test compound was a derivative of the reference compound. When developing new assays or protocols, compounds according to the present invention could be used to test their effectiveness. The compounds of the present invention may also be used in diagnostic assays involving endothelial lipase.

The present invention also encompasses an article of manufacture. As used herein, article of manufacture is intended to include, but not be limited to, kits and packages. The article of manufacture of the present invention, comprises: (a) a first container; (b) a pharmaceutical composition located within the first container, wherein the composition, comprises: a first therapeutic agent, comprising: a compound of the present invention or a pharmaceutically acceptable salt form thereof; and, (c) a package insert stating that the pharmaceutical composition can be used for the treatment and/or prophylaxis of dyslipidemias and the sequelae thereof. In another embodiment, the package insert states that the pharmaceutical composition can be used in combination (as defined previously) with a second therapeutic agent for the treatment and/or prophylaxis of dyslipidemias and the sequelae thereof. The article of manufacture can further comprise: (d) a second container, wherein components (a) and (b) are located within the second container and component (c) is located within or outside of the second container. Located within the first and second containers means that the respective container holds the item within its boundaries.

The first container is a receptacle used to hold a pharmaceutical composition. This container can be for manufacturing, storing, shipping, and/or individual/bulk selling. First container is intended to cover a bottle, jar, vial, flask, syringe, tube (e.g., for a cream preparation), or any other container used to manufacture, hold, store, or distribute a pharmaceutical product.

The second container is one used to hold the first container and, optionally, the package insert. Examples of the second container include, but are not limited to, boxes (e.g., cardboard or plastic), crates, cartons, bags (e.g., paper or plastic bags), pouches, and sacks. The package insert can be physically attached to the outside of the first container via tape, glue, staple, or another method of attachment, or it can rest inside the second container without any physical means of attachment to the first container. Alternatively, the package insert is located on the outside of the second container. When located on the outside of the second container, it is preferable that the package insert is physically attached via tape, glue, staple, or another method of attachment. Alternatively, it can be adjacent to or touching the outside of the second container without being physically attached.

The package insert is a label, tag, marker, etc. that recites information relating to the pharmaceutical composition located within the first container. The information recited will usually be determined by the regulatory agency governing the area in which the article of manufacture is to be sold (e.g., the United States Food and Drug Administration). Preferably, the package insert specifically recites the indications for which the pharmaceutical composition has been approved. The package insert may be made of any material on which a person can read information contained therein or thereon. Preferably, the package insert is a printable material (e.g., paper, plastic, cardboard, foil, adhesive-backed paper or plastic, etc.) on which the desired information has been formed (e.g., printed or applied).

Other features of the invention should become apparent in the course of the above descriptions of exemplary embodiments that are given for illustration of the invention and are not intended to be limiting thereof.

EXAMPLES

The following Examples have been prepared, isolated and characterized using the methods disclosed herein. The following examples demonstrate a partial scope of the invention and are not meant to be limiting of the scope of the invention.

Intermediate 1. ethyl 3-methoxy-1-methyl-2-oxo-1,2-dihydropyridine-4-carboxylate

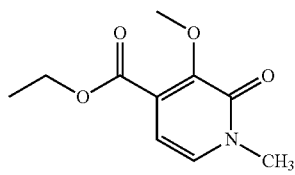

Intermediate 1A. ethyl 5-hydroxy-6-oxo-1,2,3,6-tetrahydropyridine-4-carboxylate

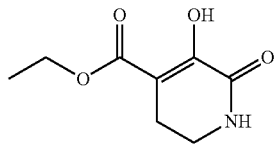

To a vigorously stirred suspension of pentane-washed (3×400 mL) potassium hydride (123 g of pre-washed KH in mineral oil; 1.07 mol) in 1.2 L of toluene in an oven-dried three neck, round-bottom reaction flask was added dropwise 300 mL (5.1 mol) of absolute EtOH over 15 min. The resulting warm homogeneous solution was allowed to cool to 40° C. To this stirred mixture was added a solution of 79 mL (5.0 mol) pyrrolidinone and 144 mL (1.06 mol) of diethyl oxalate in 250 mL of toluene with a slow steady-stream addition. Toluene (300 mL) and ethanol (200 mL) were added to dilute the thick yellow suspension that had formed. The reaction was stirred at 90° C. for 18 h followed by cooling to 40° C. before quenching with 6 N HCl (400 mL). The layers were separated. The aqueous layer was extracted with DCM (2×500 mL). The combined organic layers were dried over MgSO$_4$ and concentrated. The crude solid was purified by recrystallization (EtOAc) and the purified material was recovered by vacuum filtration. The solid was dried in a vacuum oven at 50° C. overnight to afford Intermediate 1A (130 g, 68%) as a yellow crystalline solid. mp. 142-148° C.

Intermediate 1B. ethyl 3-hydroxy-2-oxo-1,2-dihydropyridine-4-carboxylate

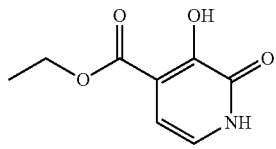

To a solution of Intermediate 1A (20 g) in xylene (400 mL) was added 10% Pd/C (4 g). The mixture was heated at 130° C. for 24 h. The reaction was filtered through a pad of Celite®. Methanol was used for filtration and washing. The filtrate was concentrated and the residue was purified by ISCO flash chromatography (silica gel, 0-100% EtOAc/hexane) to give Intermediate 1B (15 g, 80% yield).

Intermediate 1

To a solution of Intermediate 1B (2.0 g, 10.92 mmol) in DMF (15 mL) was added potassium carbonate (4.53 g, 32.8 mmol) and iodomethane (2.72 mL, 43.7 mmol). The reaction was heated at 80° C. for 3 days. The reaction mixture was diluted with DCM, washed with water, dried over MgSO$_4$, filtered and concentrated. The residue was dissolved in a small amount of DCM and charged to an 80 g silica gel cartridge which was eluted with a 25 min gradient from 0-100% EtOAc/hexane to give Intermediate 1 (1.47 g, 6.96 mmol, 63.7% yield) as an off-white solid. HPLC/MS (Method D) RT=1.2 min, [M+1]$^+$ 212.1; 1H NMR (400 MHz, CHLOROFORM-d) δ ppm 7.07 (1H, d, J=7.28 Hz), 6.33 (1H, d, J=7.03 Hz), 4.36 (2H, q, J=7.03 Hz), 4.01 (3H, s), 3.57 (3H, s), 1.38 (3H, t, J=7.15 Hz).

Intermediate 2. (1-(3,4-dichlorophenylsulfonyl)pyrrolidin-2-yl)methanamine

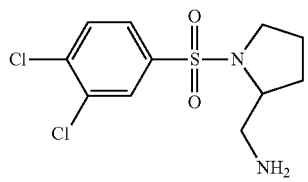 [SMILES: NCC1CCCN1S(=O)(=O)c1ccc(Cl)c(Cl)c1]

Intermediate 2A. tert-butyl (1-(3,4-dichlorophenyl-sulfonyl)pyrrolidin-2-yl)methylcarbamate

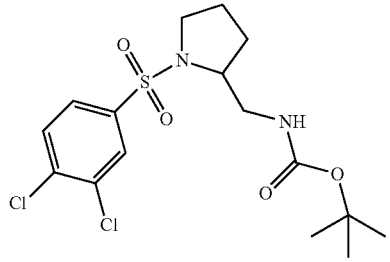 [SMILES: CC(C)(C)OC(=O)NCC1CCCN1S(=O)(=O)c1ccc(Cl)c(Cl)c1]

To a solution of 3,4-dichlorobenzene-1-sulfonyl chloride (490 mg, 2.00 mmol) was added tert-butyl pyrrolidin-2-ylmethylcarbamate (400 mg, 2.00 mmol), followed by triethylamine (0.278 mL, 2.00 mmol). The reaction was stirred at rt overnight. The reaction mixture was diluted with DCM and washed with 1N HCl, H$_2$O and brine, dried over Na$_2$SO$_4$ and decanted. The solvent was evaporated under reduced pressure and the crude product was purified on a 24 g silica gel cartridge using 0 to 100% EtOAc in hexane for 15 min, then 0 to 20% MeOH in DCM for 15 min to provide Intermediate 2A (800 mg, 1.95 mmol, 98% yield) as a white solid. HPLC/MS (Method D) RT=2.12 min, [M+1]$^+$ 309.1.

Intermediate 2

To a solution of Intermediate 2A (340 mg, 0.831 mmol) in DCM (2 mL) was added HCl (4 M in dioxane, 0.831 mL, 3.32 mmol). The reaction mixture was stirred at rt for 16 h. The reaction mixture was concentrated under reduced pressure and the residue was triturated with ether. The solid residue was dried in vacuo to give Intermediate 2 (250 mg, 0.809 mmol, 97% yield). HPLC/MS (Method D) RT=1.47 min, [M+1]$^+$ 309; 1H NMR (400 MHz, MeOD) δ ppm 7.74 (1H, s), 7.46-7.52 (2H, m), 3.52-3.61 (1H, m), 3.17 (1H, ddd, J=10.8, 7.0, 5.2 Hz), 2.98-3.04 (1H, m), 2.71-2.78 (2H, m), 1.53 (1H, ddd, J=12.5, 7.5, 7.3 Hz), 1.34-1.41 (2H, m), 1.20-1.29 (1H, m).

Intermediate 3. (1-(3,4-dichlorophenylsulfonyl)piperidin-4-yl)methanamine

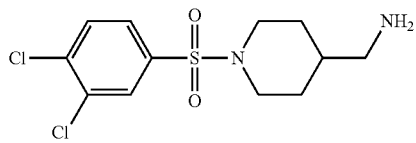 [SMILES: NCC1CCN(S(=O)(=O)c2ccc(Cl)c(Cl)c2)CC1]

Intermediate 3A. tert-butyl (1-(3,4-dichlorophenyl-sulfonyl)piperidin-4-yl)methylcarbamate

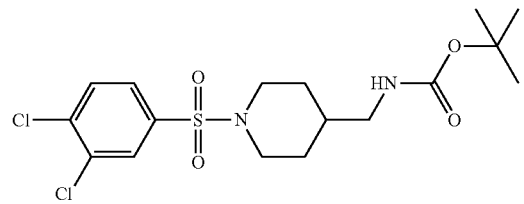 [SMILES: CC(C)(C)OC(=O)NCC1CCN(S(=O)(=O)c2ccc(Cl)c(Cl)c2)CC1]

To a solution of 3,4-dichlorobenzene-1-sulfonyl chloride (470 mg, 1.91 mmol) was added tert-butyl piperidin-4-ylmethylcarbamate (410 mg, 1.91 mmol) followed by triethylamine (0.267 mL, 1.91 mmol). The reaction mixture was stirred at rt overnight. The reaction mixture was diluted with DCM and the organic portion washed with 1N HCl, H$_2$O, and brine, dried over Na$_2$SO$_4$ and decanted. The solvent was evaporated under reduced pressure and the crude residue was purified by flash chromatography on a 24 g silica gel cartridge using 0 to 100% ethyl acetate in hexane over 15 minutes, then 0 to 20% MeOH in DCM over 15 min. to provide Intermediate 3A (800 mg, 1.890 mmol, 99% yield). HPLC/MS (Method M) RT=1.58 min, [M+1]$^+$ 324.1.

Intermediate 3

To a solution Intermediate 3A (100 mg, 0.236 mmol) in DCM (1 mL) was added HCl (4M in dioxane, 0.118 mL, 0.472 mmol). The reaction mixture was stirred at rt for 16 h. The reaction mixture was evaporated to dryness and triturated with ether. Intermediate 3 (75 mg, 0.232 mmol, 98% yield) was collected by filtration and dried in vacuo. HPLC/MS (Method M) RT=2.74 min, [M+1]$^+$ 324.1.

Intermediate 4.
1-(3,4-dichlorophenylsulfonyl)piperidin-4-amine

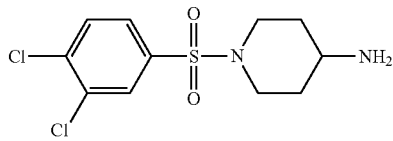 [SMILES: NC1CCN(S(=O)(=O)c2ccc(Cl)c(Cl)c2)CC1]

Intermediate 4A. tert-butyl (1-(3,4-dichlorophenyl-sulfonyl)piperidin-4-yl)methylcarbamate

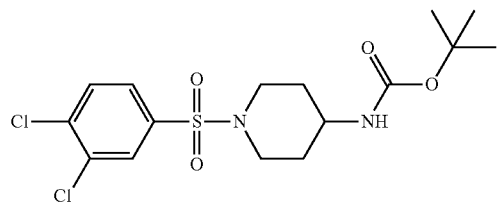 [SMILES: CC(C)(C)OC(=O)NC1CCN(S(=O)(=O)c2ccc(Cl)c(Cl)c2)CC1]

To a solution of 3,4-dichlorobenzene-1-sulfonyl chloride (490 mg, 2.00 mmol) was added tert-butyl piperidin-4-ylcarbamate (400 mg, 2.00 mmol), followed by triethylamine (0.278 mL, 2.00 mmol). The reaction was stirred at rt overnight. The reaction mixture was diluted with DCM and the organic portion washed with 1N HCl, $H_2O$, and brine, dried over $Na_2SO_4$ and decanted. The solvent was evaporated under reduced pressure and the crude residue was purified on a 24 g silica gel cartridge eluting with 0 to 100% EtOAc in hexane, then 0 to 20% MeOH in DCM to provide Intermediate 4A (810 mg, 2.0 mmol, 99% yield). HPLC/MS (Method D) RT=2.12 min, $[M+1]^+$ 309.

Intermediate 4

To a solution of Intermediate 4A (100 mg, 0.244 mmol) in DCM (1 mL) was added HCl (4M in dioxane, 0.122 mL, 0.489 mmol). The reaction mixture was stirred at rt for 16 h. The solvents were removed under vacuum and the residue was triturated with $Et_2O$ and then dried under vacuum to yield Intermediate 4 (71 mg, 0.23 mmol, 94% yield). HPLC/MS (Method D) RT=1.49 min, $[M+1]^+$ 310. 1H NMR (400 MHz, METHANOL-$d_3$) δ ppm 7.96 (1H, d, J=2.2 Hz), 7.80-7.83 (1H, m), 7.71-7.74 (1H, m), 3.88 (2H, d, J=12.7 Hz), 3.08-3.17 (1H, m), 2.51 (2H, td, J=12.3, 2.6 Hz), 2.03-2.09 (2H, m), 1.65 (2H, dd, J=12.3, 4.0 Hz).

Intermediate 5. (1-(3,4-dichlorophenylsulfonyl)azetidin-3-yl)methanamine

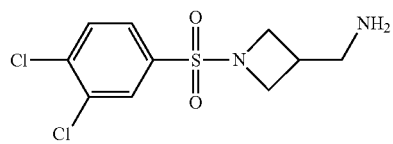 [SMILES: NCC1CN(S(=O)(=O)c2ccc(Cl)c(Cl)c2)C1]

Intermediate 5 (65 mg, 0.22 mmol, 87% yield) was prepared as a white powder following the procedure described for Intermediate 4 by replacing tert-butyl piperidin-4-yl-methylcarbamate with tert-butyl azetidin-3-yl-methylcarbamate. LC-MS (ESI) m/z 295 $(M+H)^+$, RT=1.47 min (Method B).

Intermediate 6. 3-methoxy-1-methyl-2-oxo-1,2-dihydropyridine-4-carboxylic acid

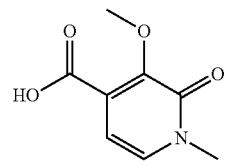

To a solution of Intermediate 1 (2.2 g, 10 mmol) in THF (3 mL) was added LiOH (10.8 mg, 0.451 mmol) and the reaction mixture was stirred at rt for 16 h. The reaction mixture was acidified to pH=1 using HCl (1M aq., 12.50 mL, 12.50 mmol) concentrated and then evaporated to dryness to provide Intermediate 6 (1.9 g, 10 mmol, 100% yield) as a gray solid. HPLC/MS (Method D) RT=0.42 min, $[M+1]^+$ 184. 1H NMR (400 MHz, DMSO-$d_6$) δ ppm 7.28 (1H, d, J=7.1 Hz), 5.97 (1H, d, J=6.6 Hz), 3.62 (3H, s), 3.31 (3H, s).

Intermediates 7-10 were synthesized using the methodology described in Intermediate 6

| Intermediate 7 | 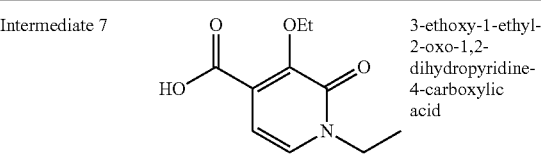 | 3-ethoxy-1-ethyl-2-oxo-1,2-dihydropyridine-4-carboxylic acid |
| --- | --- | --- |
| Intermediate 8 | 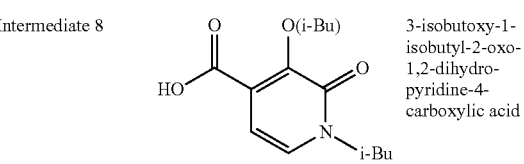 | 3-isobutoxy-1-isobutyl-2-oxo-1,2-dihydro-pyridine-4-carboxylic acid |
| Intermediate 9 | 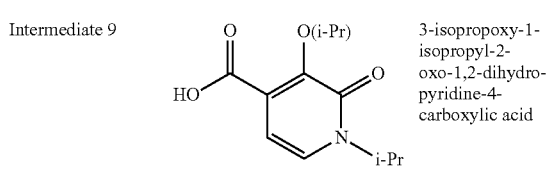 | 3-isopropoxy-1-isopropyl-2-oxo-1,2-dihydro-pyridine-4-carboxylic acid |
| Intermediate 10 | 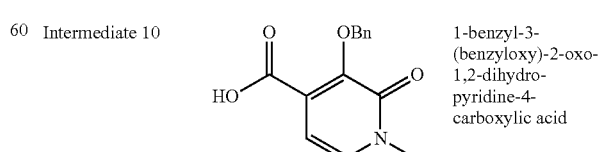 | 1-benzyl-3-(benzyloxy)-2-oxo-1,2-dihydro-pyridine-4-carboxylic acid |

Intermediate 11. ethyl 1-(cyclopropylmethyl)-3-hydroxy-2-oxo-1,2-dihydropyridine-4-carboxylate

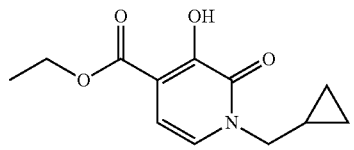 [SMILES: CCOC(=O)c1ccn(CC2CC2)c(=O)c1O]

To a solution of Intermediate 1B (250 mg, 1.370 mmol) in DMF (2 mL) was added cesium carbonate (1.12 g, 3.41 mmol) and (bromomethyl)cyclopropane (553 mg, 4.09 mmol). The reaction was heated at 80° C. for 3 h. The reaction mixture was diluted with EtOAc, washed with brine, dried over $Na_2SO_4$, filtered and concentrated. The residue was dissolved in a small amount of DCM and charged to a 24 g silica gel cartridge which was eluted with a 25 min gradient from 0-100% EtOAc/hexane to give Intermediate 11 (82 mg, 0.350 mmol, 25.3% yield) as an oil. HPLC/MS (Method D) RT=1.64 min, [M+1]$^+$ 238.1; 1H NMR (400 MHz, CHLOROFORM-d) δ ppm 7.20 (1H, d, J=7.28 Hz), 6.30 (1H, d, J=7.03 Hz), 4.21 (2H, q, J=7.03 Hz), 3.65-3.66 (2H, m), 1.29 (1H, m), 1.19 (3H, t, J=7.04 Hz), 0.78 (2H, m), 0.61 (2H, m).

Intermediate 12. (R)—N-(1-(3-bromophenyl)ethyl)-3-methoxy-1-methyl-2-oxo-1,2-dihydropyridine-4-carboxamide

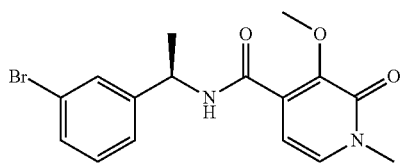 [SMILES: COc1c(C(=O)N[C@H](C)c2cccc(Br)c2)ccn(C)c1=O]

Intermediate 12A. 3-methoxy-1-methyl-2-oxo-1,2-dihydropyridine-4-carbonyl chloride

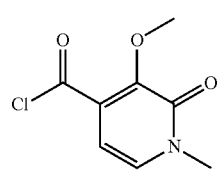

3-Methoxy-1-methyl-2-oxo-1,2-dihydropyridine-4-carboxylic acid (Intermediate 6) (0.44 g, 2.4 mmol) was stirred in thionyl chloride (2.00 mL, 27.4 mmol) at reflux for 2 h. The cooled mixture was concentrated and dried under vacuum. Intermediate 12A was used directly for the next step without further purification.

Intermediate 12

To a solution of Intermediate 12A (484 mg, 2.40 mmol) in DCM (5 mL) was added TEA (1.00 mL, 7.20 mmol) dropwise at 0° C. and (R)-1-(3-bromophenyl)ethanamine (504 mg, 2.52 mmol) in 5 mL of DCM. The reaction mixture was allowed to reach rt and was stirred for 14 h. The reaction mixture was extracted with 1N HCl and the layers were separated. The aqueous layer was extracted with DCM. The organic layers were combined, washed with brine and dried over $Na_2SO_4$ decanted and concentrated. The residue was loaded onto a 24 g silica gel column and purified by silica gel chromatography, eluting with 0-10% MeOH in DCM to give Intermediate 12 (345 mg, 0.945 mmol, 39.4% yield) as a yellow solid. HPLC/MS (Method C) RT=1.75 min [M+H]$^+$ 366.9.

Intermediate 13. (R)-6-(trifluoromethyl)-2,3-dihydro-1H-inden-1-amine hydrochloride

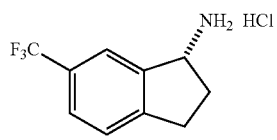

Intermediate 13A. (R)-2-methyl-N-(6-(trifluoromethyl)-2,3-dihydro-1H-inden-1-ylidene)propane-2-sulfinamide

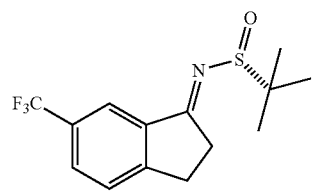 [SMILES: CC(C)(C)[S@@](=O)/N=C1\CCc2ccc(C(F)(F)F)cc21]

To a stirred solution of (R)-2-methylpropane-2-sulfinamide (578 mg, 4.77 mmol) and 6-(trifluoromethyl)-2,3-dihydro-1H-inden-1-one (1000 mg, 5.00 mmol) in THF (4 mL) at rt was added tetraethoxytitanium (1.88 mL, 9.08 mmol). The reaction mixture was heated at 75° C. overnight. The reaction mixture was allowed to cool and used directly in the next step. LC-MS (ESI) 304.0 (M+H), RT=2.20 minutes (Method B).

Intermediate 13B. (R)-2-methyl-N4R)-6-(trifluoromethyl)-2,3-dihydro-1H-inden-1-yl)propane-2-sulfinamide

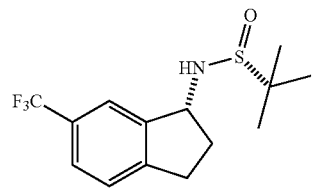 [SMILES: CC(C)(C)[S@@](=O)N[C@@H]1CCc2ccc(C(F)(F)F)cc21]

Sodium borohydride (756 mg, 20.0 mmol) was stirred in a round-bottomed flask under argon at −40 to −50° C. The reaction mixture of Intermediate 13A was added dropwise to the flask, and THF was added to the reaction mixture (ca. 0.6 M). The resulting mixture was allowed to warm to 0° C. over 1.5 h. The reaction mixture was cooled in dry ice and MeOH was added dropwise until gas evolution stopped. The mixture was stirred at rt for 20 min, filtered through Celite® and rinsed with EtOAc then CH$_2$Cl$_2$. The filtrate was washed with brine (2×) and dried over MgSO$_4$, filtered and concentrated. The residue was purified on ISCO flash chromatograph on silica gel (hexanes/EtOAc) to give Intermediate 13B (370 mg, 1.21 mmol, 26.7% yield) as colorless crystals. LC-MS (ESI) 306.0 (M+H), RT=2.10 min (Method B).

Intermediate 13

Intermediate 13B (370 mg, 1.21 mmol) was stirred in MeOH (5 mL) at rt. 4N HCl in dioxane (2 mL) was added. The resulting mixture was stirred at rt for 20 min. The solvents were evaporated and CH$_2$Cl$_2$ (3×) was added and evaporated. The resulting white solids were vacuum dried for 1 h to give intermediate 13 (84 mg, 0.35 mmol, 29% yield) and methyl 2-methylpropane-2-sulfinate. The HCl salt was used directly in the subsequent reactions. $^1$H NMR (400 MHz, MeOD) δ ppm 7.57 (1H, d, J=7.8 Hz), 7.47 (1H, d, J=7.6 Hz), 7.25 (1H, t, J=7.8 Hz), 4.88 (1H, dd, J=7.8, 4.8 Hz), 3.09-3.23 (1H, m), 2.90-3.08 (1H, m), 2.64 (1H, dddd, J=14.1, 8.5, 8.3, 5.7 Hz), 2.01-2.23 (1H, m, J=14.1, 8.7, 5.3, 5.3 Hz).

Intermediate 14. Cis-4-phenylcyclohexanamine

Intermediate 14A.
Cis-N-benzhydryl-4-phenylcyclohexanamine and
Intermediate 14B
trans-N-benzhydryl-4-phenylcyclohexanamine

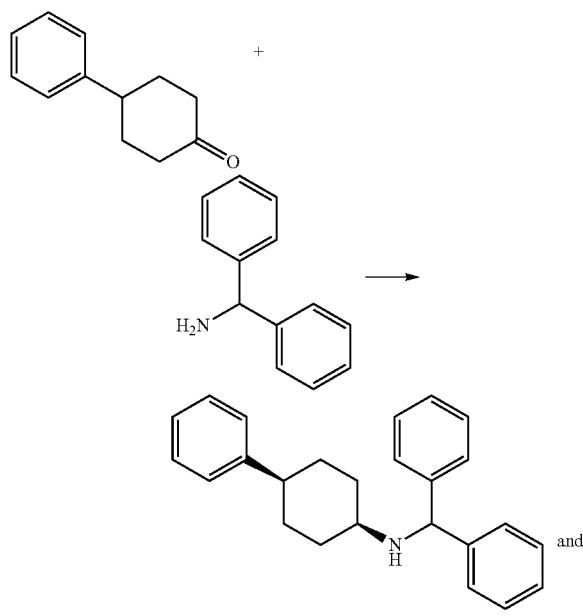

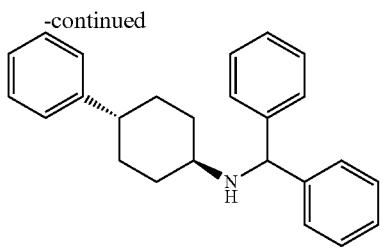

To a solution of 4-phenylcyclohexanone (500 mg, 2.87 mmol) and diphenylmethanamine (526 mg, 2.87 mmol) in DCE (4 mL) at 0° C. was added sodium triacetoxyborohydride (912 mg, 4.30 mmol) by portions slowly. A white suspension resulted and was stirred for 5 min before the ice-water bath was removed. The reaction was stirred at rt for 1.5 h. The reaction was quenched with water carefully, then saturated NaHCO$_3$ was added carefully and the aqueous layer was extracted with DCM (3×). The organic layers were combined, washed with brine, dried over Na$_2$SO$_4$, and concentrated. The residue was purified by ISCO flash chromatography (0-100% hexane/EtOAc) to give cis-N-benzhydryl-4-phenylcyclohexanamine (Intermediate 14A) (734 mg, 2.15 mmol, 74.9% yield) LC-MS (ESI) m/z 342.1 (M+H), RT=1.76 min (Method B); $^1$H NMR (400 MHz, CHLOROFORM-d) δ ppm 7.37 (4H, d, J=7.33 Hz), 7.23-7.31 (6H, m), 7.11-7.23 (5H, m), 4.91 (1H, s), 2.80-2.88 (1H, m), 2.46-2.56 (1H, m), 1.74-1.90 (4H, m), 1.60-1.70 (2H, m), 1.47-1.59 (2H, m); and trans-N-benzhydryl-4-phenylcyclohexanamine (Intermediate 14B) (191 mg, 0.559 mmol, 19.49% yield), LC-MS (ESI) m/z 342.1 (M+H), RT=1.76 min (Method B).

Intermediate 14

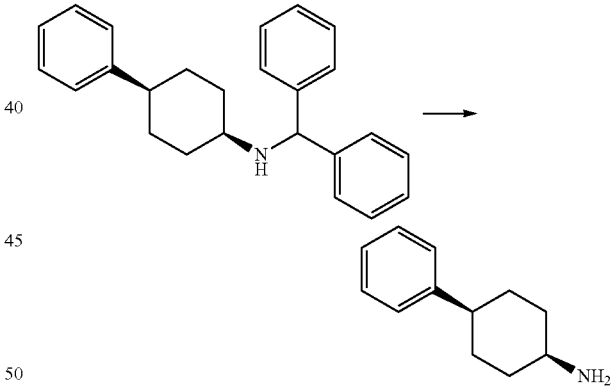

To a solution of Intermediate 14A (714 mg, 2.091 mmol) in MeOH (20 mL) and EtOAc (5 mL) were added 10% palladium on carbon (71.4 mg, 0.067 mmol) and acetic acid (0.120 mL, 2.09 mmol). The reaction was stirred under H$_2$ balloon for 3 h. The reaction mixture was filtered through Celite® and rinsed with EtOAc. The filtrate was concentrated, re-dissolved in DCM, and the organic layer was extracted with 1N HCl. The aqueous layer was made basic with 1N NaOH and extracted with DCM (3×). The combined organic layers were washed with brine, dried over Na$_2$SO$_4$, decanted, and concentrated to give Intermediate 14 (321 mg, 1.83 mmol, 88% yield) as a colorless wax. LC-MS (ESI) m/z 176.1 (M+H), RT=1.43 min (Method B). $^1$H NMR (400 MHz, DMSO-d) δ ppm 7.24-7.30 (4H, m), 7.13-7.18 (1H, m), 3.10-3.16 (1H, m), 2.42-2.50 (1H, m), 1.80-1.93 (2H, m), 1.60-1.66 (4H, m), 1.44-1.54 (2H, m).

Intermediate 15. trans-4-phenylcyclohexanamine

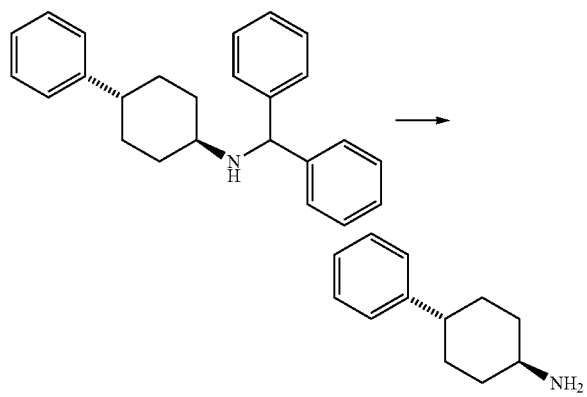

Intermediate 15 was synthesized in a manner similar to intermediate 14 by deprotection of the trans-N-benzhydryl-4-phenylcyclohexanamine obtained above (Intermediate 14B).

Intermediate 16; cis-4-(3,4-dichlorophenyl)-1,2,3,4-tetrahydronaphthalen-1-amine

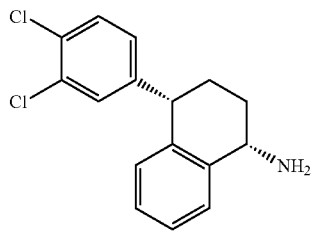 [SMILES: N[C@H]1CC[C@@H](c2ccc(Cl)c(Cl)c2)c2ccccc21]

Intermediate 16 is commercially available.

Intermediate 17:
3-hydroxy-2-oxo-1,2-dihydropyridine-4-carbonyl chloride

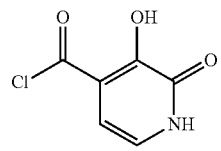 [SMILES: O=C(Cl)c1cc[nH]c(=O)c1O]

Intermediate 17A.
3-hydroxy-2-oxo-1,2-dihydropyridine-4-carboxylic acid

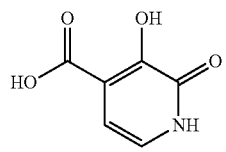

To a heterogeneous solution of ethyl 3-hydroxy-2-oxo-1,2-dihydropyridine-4-carboxylate (200 mg, 1.09 mmol) (Intermediate 1B) in THF (3 mL) was added LiOH (26.1 mg, 1.09 mmol) and H$_2$O (1 mL). The reaction mixture was stirred for 16 h. The reaction mixture was adjusted to pH 2 and filtered. The filter cake was evaporated to dryness to give Intermediate 17A (160 mg, 1.0 mmol, 94% yield). HPLC/MS (Method D) RT=0.45 min, [M+1]$^+$ 155.9.

Intermediate 17

To a solution of Intermediate 17A (400 mg, 2.58 mmol) was added thionyl chloride (0.376 mL, 5.16 mmol). The reaction mixture was stirred at 60° C. for 3 h. The reaction mixture was allowed to cool to rt then concentrated under reduced pressure to give Intermediate 17 (430 mg, 2.5 mmol, 96% yield). HPLC/MS (Method D) RT=0.72 min, [M+1]$^+$ 174.

Intermediate 18. Ethyl 6-bromo-3-methoxy-1-methyl-2-oxo-1,2-dihydropyridine-4-carboxylate

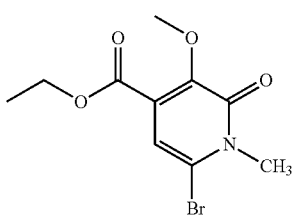 [SMILES: CCOC(=O)c1cc(Br)n(C)c(=O)c1OC]

To a solution of Intermediate 1 (109 mg, 0.516 mmol) in DCE (2.0 mL) was added NBS (110 mg, 0.619 mmol). The reaction mixture was stirred at rt overnight and then was concentrated under reduced pressure. The residue was diluted with EtOAc, washed with water and brine, dried over anhydrous sodium sulfate, filtered and evaporated under reduced pressure. The residue was dissolved in a small amount of DCM and charged to a 12 g silica gel cartridge which was eluted with a 25 min gradient from 0-100% EtOAc/hexane to give Intermediate 18 (138 mg, 0.476 mmol, 69% yield) as a white solid. HPLC/MS (Method D) RT=1.4 min, [M+1]$^+$ 291.9; 1H NMR (400 MHz, CHLOROFORM-d) δ ppm 7.29 (1H, s), 4.42 (2H, q, J=7.28 Hz), 3.99 (3H, s), 3.55 (3H, s), 1.39 (3H, t, J=7.15 Hz).

Intermediate 19. N-(3-(3,4-dichlorophenyl)propyl)-3-hydroxy-1-methyl-2-oxo-6-(trifluoromethyl)-1,2-dihydropyridine-4-carboxamide

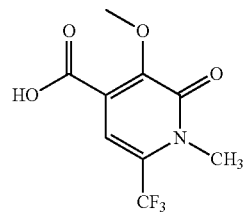

Intermediate 19A. Ethyl 6-iodo-3-methoxy-1-methyl-2-oxo-1,2-dihydropyridine-4-carboxylate

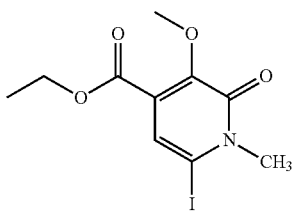 [SMILES: CCOC(=O)c1cc(I)n(C)c(=O)c1OC]

To a solution of Intermediate 1 (101 mg, 0.478 mmol) in DMF (0.5 mL) was added NIS (108 mg, 0.478 mmol) at rt. The reaction was stirred at rt for 3 days. An additional equivalent of NIS (67 mg, 0.30 mmol) was added and the reaction mixture heated at 60° C. overnight. The reaction was allowed to cool, diluted with DCM (40 mL) and the organic portion washed with water and brine, dried over MgSO$_4$, filtered and concentrated under reduced pressure. The residue was dissolved in a small amount of DCM and charged to a 12 g silica gel cartridge which was eluted with a 25 min gradient from 0-100% EtOAc/hexane to give Intermediate 19A (81 mg, 50% yield) as a yellow solid.

Intermediate 19B. ethyl 3-methoxy-1-methyl-2-oxo-6-(trifluoromethyl)-1,2-dihydropyridine-4-carboxylate

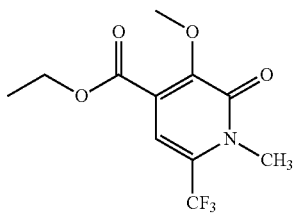 [SMILES: CCOC(=O)c1cc(C(F)(F)F)n(C)c(=O)c1OC]

To a solution of Intermediate 19A (31 mg, 0.092 mmol) in DMF (3 mL) at room temperature under argon was added copper (I) iodide (35.0 mg, 0.184 mmol) and methyl 2,2-difluoro-2-(fluorosulfonyl)acetate (35.3 mg, 0.184 mmol). The reaction mixture was heated at 95° C. overnight. The reaction was allowed to cool to rt. DCM (30 mL) was added to the reaction mixture and the organic portion was washed with water (3×10 mL) and brine (10 mL). The organic phase was dried over MgSO$_4$, filtered and concentrated to give the crude product. The crude product was dissolved in a small amount of DCM and charged to a 12 g silica gel cartridge which was eluted with a 25 min gradient from 0-100% EtOAc/hexane to give Intermediate 19B (18 mg, 0.064 mmol, 70% yield) as a colorless oil.

Intermediate 19

To a solution of Intermediate 19B (18 mg, 0.064 mmol) in THF (1.5 mL) and MeOH (0.5 mL) was added lithium hydroxide (14 mg, 0.59 mmol) and water (0.25 mL). The reaction was heated at 65° C. overnight. Additional lithium hydroxide was added (10. mg, 0.42 mmol) and heated resumed at 65° C. for 5 h. The reaction mixture was concentrated to give Intermediate 19 (16 mg, 0.064 mmol, 99% yield) as an off-white solid which was used without purification.

Intermediate 20: 4-(3-(3,4-dichlorophenyl)-1,2,4-oxadiazol-5-yl)butan-1-amine

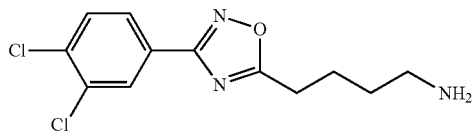 [SMILES: NCCCCc1nc(-c2ccc(Cl)c(Cl)c2)no1]

Intermediate 20A.
(Z)-3,4-dichloro-N'-hydroxybenzimidamide

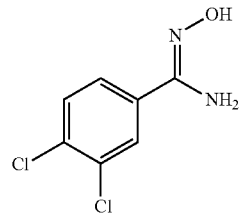 [SMILES: N/C(=N\O)c1ccc(Cl)c(Cl)c1]

A solution of 3,4-dichlorobenzonitrile (2.000 g, 11.63 mmol), hydroxylamine hydrochloride (1.649 mL, 12.79 mmol) and sodium hydroxide (4.15 mL, 12.4 mmol) in ethanol (40 mL) was stirred at rt for 1 h. Concentrated and refluxed in hexane for 30 min and concentrated in vacuo. The product Intermediate 1A was used directly for the next step. HPLC/MS (Method C) RT=1.24 min [M+H]$^+$ 204.9.

Intermediate 20B. tert-butyl 4-(3-(3,4-dichlorophenyl)-1,2,4-oxadiazol-5-yl)butylcarbamate

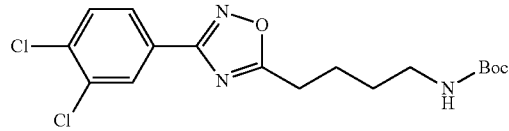 [SMILES: CC(C)(C)OC(=O)NCCCCc1nc(-c2ccc(Cl)c(Cl)c2)no1]

The 5-(tert-butoxycarbonylamino)pentanoic acid (424 mg, 1.95 mmol) was introduced into a microwave vial charged with DMAP (238 mg, 1.95 mmol) and Intermediate 20A (400 mg, 1.95 mmol). The reactants were dissolved in DMF (5 mL) and the DIC (0.304 mL, 1.95 mmol) was added. The reaction mixture was stirred at rt overnight. The reaction mixture was diluted with 3 mL of pyridine. The vial was capped and the reaction was heated in the microwave at 145° C. for 20 min. The reaction mixture was allowed to cool to rt. The reaction mixture was diluted with EtOAc and washed with water and brine. The organic portion was concentrated under reduced pressure and purified by silica gel chromatography with EtOAc/Hexane to give Intermediate 20B as a white solid (230 mg, 0.595 mmol, 30.5% yield). HPLC/MS (Method D) RT=2.40 min [M+H]$^+$ 385.9.

Intermediate 20

To a solution of Intermediate 20B (225 mg, 0.582 mmol) in DCM (3 mL) was added TFA (3.00 mL, 38.9 mmol). The resulting reaction solution was stirred at rt for 3 h. The reaction mixture was quenched with saturated NaHCO$_3$ and the aqueous phase extracted with DCM. The combined organic portions were dried over Na$_2$SO$_4$, and concentrated under reduced pressure to give Intermediate 20 (169 mg, 0.591 mmol, 101% yield) as a white solid. HPLC/MS (Method C) RT=2.60 min [M+H]$^+$ 286.0; 1H NMR (400 MHz, METHANOL-d3) d ppm 8.18 (1H, d, J=2.20 Hz), 7.97 (1H, dd, J=8.35, 2.20 Hz), 7.70 (1H, d, J=8.35 Hz), 3.30-3.31 (2H, m), 3.05 (2H, t, J=7.47 Hz), 2.84 (2H, br.s.), 1.94 (2H, qd, J=7.62, 7.47 Hz), 1.61-1.78 (2H, m, J=7.58, 7.58, 7.47, 7.25 Hz).

Example 1

6-(3-fluoro-5-(trifluoromethyl)phenyl)-3-hydroxy-1-methyl-2-oxo-N-((1s,4s)-4-phenylcyclohexyl)-1,2-dihydropyridine-4-carboxamide

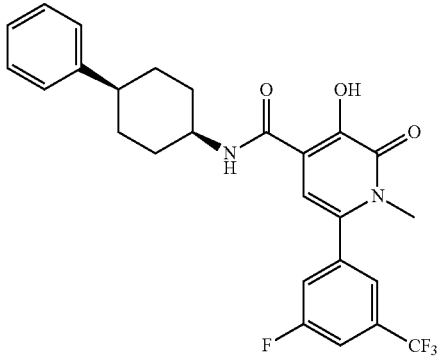 [SMILES: Cn1c(-c2cc(F)cc(C(F)(F)F)c2)cc(C(=O)N[C@H]2CC[C@@H](c3ccccc3)CC2)c(O)c1=O]

Example 1A ethyl 6-(3-fluoro-5-(trifluoromethyl)phenyl)-3-methoxy-1-methyl-2-oxo-1,2-dihydropyridine-4-carboxylate

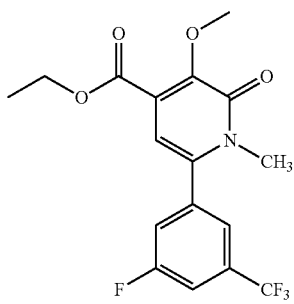 [SMILES: CCOC(=O)c1cc(-c2cc(F)cc(C(F)(F)F)c2)n(C)c(=O)c1OC]

A mixture of Intermediate 18 (319 mg, 1.10 mmol), 3-fluoro-5-(trifluoromethyl)phenylboronic acid (343 mg, 1.65 mmol), sodium carbonate (2 M) (1.649 mL, 3.300 mmol) in DME (9 mL) added to a microwave vial and degassed with argon. Pd(Ph$_3$)$_4$ (63.5 mg, 0.0550 mmol) was added and the resulting reaction mixture degassed with argon. The sealed tube was heated at 160° C. for 30 min in the microwave reactor. The reaction mixture was filtered and the filtrate was concentrated under reduced pressure with Celite® and charged to a 40 g silica gel cartridge which was eluted with a 30 min gradient from 0-100% EtOAc/hexane to provide Example 1A (240 mg, 0.643 mmol, 58.5% yield) as a yellow solid. HPLC/MS (Method D) RT=2.0 min, [M+1]$^+$ 374.1.

Example 1B 6-(3-fluoro-5-(trifluoromethyl)phenyl)-3-methoxy-1-methyl-2-oxo-1,2-dihydropyridine-4-carboxylic acid

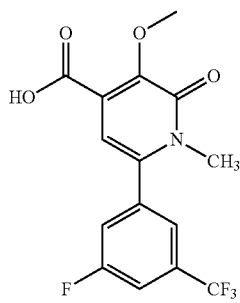 [SMILES: COc1c(C(=O)O)cc(-c2cc(F)cc(C(F)(F)F)c2)n(C)c1=O]

To a solution of Example 1A (102 mg, 0.273 mmol) in THF (3 mL) in MeOH (1 mL) was added lithium hydroxide (19.63 mg, 0.8200 mmol) and water (0.5 mL). The reaction mixture was heated at 65° C. overnight. The reaction mixture was acidified with HCl (0.091 mL, 1.1 mmol) and concentrated to give Example 1B (127 mg, 0.272 mmol, 100% yield) as a gray solid. HPLC/MS (Method D) RT=1.68 min, [M+1]$^+$ 346.0.

Example 1C 6-(3-fluoro-5-(trifluoromethyl)phenyl)-3-methoxy-1-methyl-2-oxo-1,2-dihydropyridine-4-carbonyl chloride

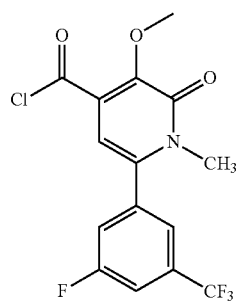 [SMILES: COc1c(C(=O)Cl)cc(-c2cc(F)cc(C(F)(F)F)c2)n(C)c1=O]

A suspension of Example 1B (434 mg, 1.257 mmol) in thionyl chloride (5.00 mL, 68.5 mmol) was heated at 65° C. overnight. The reaction mixture was concentrated under reduced pressure to give Example 1C (410 mg, 1.13 mmol, 90% yield) as a yellow solid.

Example 1D 6-(3-fluoro-5-(trifluoromethyl)phenyl)-3-methoxy-1-methyl-2-oxo-N-(cis-4-phenylcyclohexyl)-1,2-dihydropyridine-4-carboxamide

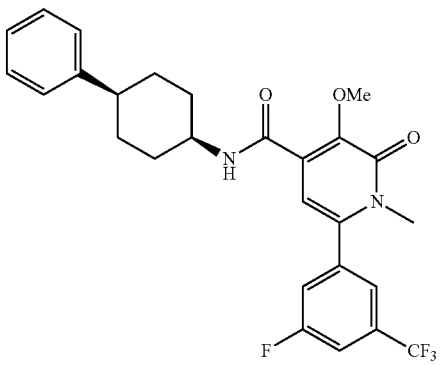

To a solution of 4-phenylcyclohexanamine (Intermediate 14) (71.7 mg, 0.409 mmol) in DCM (3 mL) was added TEA (0.095 mL, 0.68 mmol) followed by a solution of Example 1C (124 mg, 0.341 mmol) in DCM (1 mL). The reaction mixture was stirred at rt for 1 h. The reaction mixture was diluted with EtOAc (15 mL), washed with 1N HCl, saturated NaHCO$_3$ solution, brine and dried over MgSO$_4$, filtered and concentrated under reduced pressure to give Example 1D (151 mg, 0.300 mmol, 88% yield) as a yellow foam. HPLC/MS (Method D) RT=2.2 min, [M+1]$^+$ 503.2.

Example 1

To a solution of Example 1D (151 mg, 0.300 mmol) in DCE (2 mL) was added boron tribromide (1.0 M in heptanes) (0.451 mL, 0.451 mmol) during which the mixture turned to a dark green suspension. The reaction was stirred at rt for 1.5 h. The reaction was quenched with MeOH (0.5 mL) and 5 drops of water. The mixture was concentrated, and the residue was dissolved in MeOH and purified by reverse phase preparative HPLC (phenomenex Luna, 5μ, C18 column, 30×250 mm, 20 min gradient from 50 to 60% B. A=$H_2O$/ACN/TFA 90/10/0.1. B=ACN/$H_2O$/TFA 90/10/0.1) to provide Example 1 (28.9 mg, 0.0590 mmol, 19.7% yield). 1H NMR (400 MHz, CHLOROFORM-d) δ ppm 7.38 (1H, s), 7.12-7.34 (7H, m), 6.86 (1H, s), 6.55 (1H, d, J=7.28 Hz), 4.26 (1H, dt, J=7.03, 3.51 Hz), 3.68 (3H, s), 2.50-2.62 (1H, m), 1.64-1.97 (6H, m), 1.36-1.54 (2H, m).

Examples 2-7 were synthesized from Compound IC and the corresponding amines following the procedure described for Example 1. The HPLC-MS data (retention time, mass and conditions) for Examples 2-7 are listed in Table 2.

Example 8

N-(cis-4-(3,4-dichlorophenyl)-1,2,3,4-tetrahydronaphthalen-1-yl)-3-hydroxy-1-methyl-2-oxo-1,2-dihydropyridine-4-carboxamide

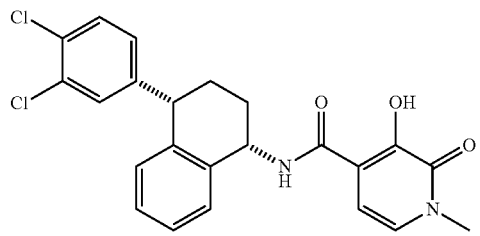

Example 8A

N-(cis-4-(3,4-dichlorophenyl)-1,2,3,4-tetrahydronaphthalen-1-yl)-3-hydroxy-1-methyl-2-oxo-1,2-dihydropyridine-4-carboxamide

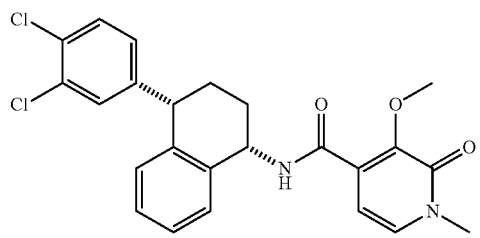

To a solution of cis-4-(3,4-dichlorophenyl)-1,2,3,4-tetrahydronaphthalen-1-amine (10 mg, 0.034 mmol) (Intermediate 16) and 3-methoxy-1-methyl-2-oxo-1,2-dihydropyridine-4-carbonyl chloride (Intermediate 12A) (6.90 mg, 0.034 mmol) in DCM (1 mL) was added $Et_3N$ (0.014 mL, 0.10 mmol). The reaction mixture was stirred for 2 h. The reaction mixture was quenched with $H_2O$ and DCM. The DCM portion was dried over $Na_2SO_4$, filtered and the solvent removed under reduced pressure to give Example 8A which was used without further purification.

Example 8

To a solution of Example 8A (13 mg, 0.028 mmol) in DCM (0.5 mL) and DCE (0.5 mL) was added boron trichloride-methyl sulfide complex (30.6 mg, 0.171 mmol). The reaction mixture was stirred at 70° C. for 16 h. The reaction mixture was quenched with ice and MeOH and example 8 isolated via prep HPLC (10 minute gradient from 5 to 100% B; Column: Phenomenex AXIA Luna 100×20 mm 5 μm; Solvent A: 10% ACN-90% $H_2O$-0.1% TFA; Solvent B: 90% ACN-10% $H_2O$-0.1% TFA). The desired fractions were evaporated to dryness to give Example 8 (5 mg, 0.01 mmol, 40% yield). LCMS RT=2.27 min, [M+1]=443.1 {(MeOH/$H_2O$/TFA) Phenom. Luna C18; 50×4.6 mm; 4 min Grad}; HPLC (150×4.6 mm 3.5 μm, 254 nm): Sunfire {RT=11.2 min, 95%}; Xbridge {RT=9.9 min, 96.3%}. $^1$H NMR (500 MHz, MeOD) δ ppm 2.01-2.06 (m, 3H) 2.19-2.25 (m, 1H) 3.59 (s, 3H) 4.20 (t, J=6.33 Hz, 1H) 5.33 (t, J=5.64 Hz, 1H) 6.74 (d, J=7.43 Hz, 1H) 6.86 (d, J=7.70 Hz, 1H) 7.10 (dd, J=8.25, 1.93 Hz, 1H) 7.14 (d, J=7.43 Hz, 1H) 7.18 (t, J=7.57 Hz, 1H) 7.24 (t, J=7.29 Hz, 1H) 7.34 (d, J=2.20 Hz, 1H) 7.39 (d, J=7.43 Hz, 1H) 7.43-7.46 (m, 1H).

Examples 9-11 were synthesized following the procedure described for Example 8. Examples 12-15 were synthesized following the procedure described for Example 8 using amine Intermediates 2, 3, 4, 5. The analytical data (retention time, mass and conditions of LC-MS) of Example 9-15 are listed in Table 2.

Example 16

N-(4-(4-fluorophenoxy)benzyl)-3-hydroxy-1-methyl-2-oxo-1,2-dihydropyridine-4-carboxamide

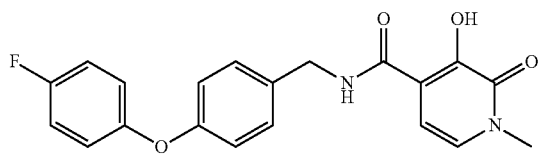 [SMILES: Cn1ccc(C(=O)NCc2ccc(Oc3ccc(F)cc3)cc2)c(O)c1=O]

Example 16A

N-(4-(4-fluorophenoxy)benzyl)-3-hydroxy-1-methyl-2-oxo-1,2-dihydropyridine-4-carboxamide

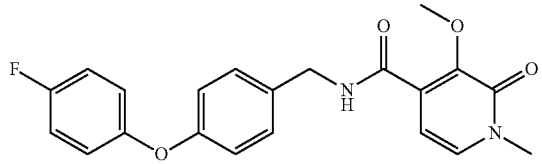 [SMILES: COc1c(C(=O)NCc2ccc(Oc3ccc(F)cc3)cc2)ccn(C)c1=O]

Methoxy-1-methyl-2-oxo-1,2-dihydropyridine-4-carboxylic acid (Intermediate 6) (40 mg, 0.19 mmol) and (4-(4-fluorobenzyl)phenyl)methanamine, HCl (47.3 mg, 0.188 mmol), were dissolved in 1 mL of DMF. EDC (54.0 mg, 0.282 mmol) and HOBT (34.5 mg, 0.225 mmol) were added and the mixture was stirred for 5 min. N-methylmorpholine (0.062 mL, 0.56 mmol) was added and the mixture was stirred at room temperature for 45 min. The reaction mixture was then diluted with ethyl acetate and washed with water followed by 2×50 mL of brine. The organic phase was dried over sodium sulfate and the solvent removed under reduced pressure to provide the crude product which was purified by ISCO flash chromatography on silica gel (12 g) eluting with 20-100% B over 10 min (solvent A: hexanes; solvent B: 10% MeOH in ethyl acetate) to provide Example 16A (52.8 mg, 72%). LCMS RT=0.92 min, [M+1]=383 (BEH C18; 50×2.1 mm column; 10-90% ACN/H₂O gradient over 1 min); ¹H NMR (400 MHz, chloroform-D) δ ppm 3.56 (s, 3H) 4.01 (s, 3H) 4.59 (d, J=5.52 Hz, 2H) 6.81 (d, J=7.28 Hz, 1H) 6.88-7.05 (m, 6H) 7.11 (d, J=7.28 Hz, 1H) 7.28 (d, J=8.53 Hz, 2H) 8.31 (s, 1H).

Example 16

To a solution of Example 16A (50 mg, 0.13 mmol) in CH₂Cl₂ (2 mL) was added trichloroborane (0.353 mL, 0.353 mmol) dropwise. The resulting brown solution was stirred at room temperature for 1 h. The reaction was quenched with MeOH and concentrated to dryness in vacuo to give a yellow oil. Purification by preparative HPLC (YMC Sunfire 5 μm C18 30×100 mm column, 26-90% methanol, water with 0.1% TFA linear gradient over 10 min.) provided Example 16 (14.6 mg, 30.0%). LCMS RT=0.92 min [M+Na]=391 (BEH C18; 50×2.1 mm column; 10-90% ACN water gradient over 1 min.) ¹H NMR (400 MHz, chloroform-D) δ ppm 3.62 (s, 3H) 4.61 (d, J=5.77 Hz, 2H) 6.85-7.06 (m, 8H) 7.30 (d, J=8.53 Hz, 2H) 7.99 (s, 1H).

Examples 17-31 were synthesized from Intermediate 6 following the procedure described for Example 16. Example 32 was synthesized from acid Intermediate 19 and appropriate amine following a similar procedure described for Example 16. The analytical data (retention time, mass and conditions of LC-MS) of Examples 17-32 are listed in Table 2.

Example 33

N-(1-(4-fluorophenyl)piperidin-4-yl)-3-hydroxy-2-oxo-1-(2,2,2-trifluoroethyl)-1,2-dihydropyridine-4-carboxamide

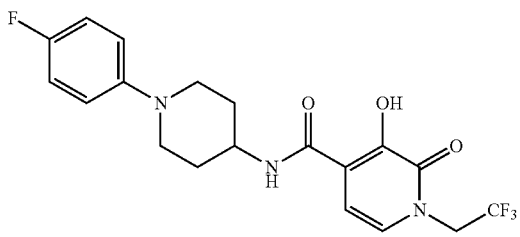 [SMILES: O=C(NC1CCN(c2ccc(F)cc2)CC1)c1ccn(CC(F)(F)F)c(=O)c1O]

Example 33A ethyl 3-methoxy-2-oxo-1,2-dihydropyridine-4-carboxylate

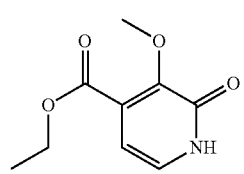

To a solution of ethyl 3-hydroxy-2-oxo-1,2-dihydropyridine-4-carboxylate (Intermediate 1B) (500 mg, 2.73 mmol) in acetonitrile (17 mL) and ethyl ether (1.9 mL) was cooled to 0° C. and trimethylsilyldiazomethane (1.50 mL, 3.00 mmol) was added. The reaction mixture was stirred at rt for 30 h. The reaction mixture was filtered and the filtrate was evaporated under reduced pressure to provide the crude product. The crude product was purified via ISCO flash chromatography on silica gel using a 15 min gradient from 0 to 100% EtOAc in hexane to give Example 33A (330 mg, 1.67 mmol, 61.3% yield).

Example 33B ethyl 3-methoxy-2-oxo-1-(2,2,2-trifluoroethyl)-1,2-dihydropyridine-4-carboxylate

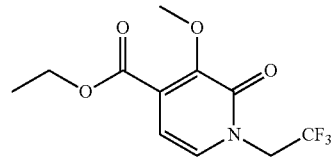 [SMILES: CCOC(=O)c1ccn(CC(F)(F)F)c(=O)c1OC]

To a solution of Example 33A (245 mg, 1.24 mmol) in DCM (3 mL) was added Cs₂CO₃ (810 mg, 2.485 mmol). The reaction mixture was stirred for 10 min at 60° C. then 2,2,2-trifluoroethyl trichloromethanesulfonate (350 mg, 1.24 mmol) was added. The reaction mixture was stirred at rt for 16 h. The reaction mixture was partition between H₂O and DCM. The DCM portion was evaporated under reduced pressure to give the crude product which was purified via ISCO flash chromatography on silica gel using a 10 min gradient eluting from 0 to 15% MeOH in DCM for 15 min to give Example 33B (180 mg, 0.645 mmol, 51.9% yield).

Example 33C 3-methoxy-2-oxo-1-(2,2,2-trifluoroethyl)-1,2-dihydropyridine-4-carboxylic acid

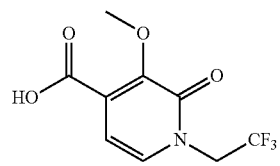 [SMILES: COc1c(C(=O)O)ccn(CC(F)(F)F)c1=O]

To a solution of Example 33C (180 mg, 0.645 mmol) was added LiOH (46.3 mg, 1.93 mmol) and NaOH (0.645 mL, 0.645 mmol). The reaction mixture was stirred at 50° C. for 16 h. The reaction mixture was cooled and the pH adjusted to 2. The reaction mixture was extracted into EtOAc, dried over Na₂SO₄ and dried in vacuo to give Example 33C (150 mg, 0.597 mmol, 93% yield).

Example 33D 3-methoxy-2-oxo-1-(2,2,2-trifluoroethyl)-1,2-dihydropyridine-4-carbonyl chloride

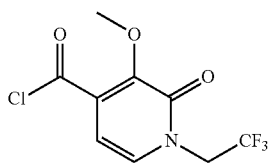 [SMILES: COc1c(C(=O)Cl)ccn(CC(F)(F)F)c1=O]

To a solution of Example 33D (140 mg, 0.557 mmol) in thionyl chloride (407 μL, 5.57 mmol) was stirred at 70° C. for 2 h. The reaction mixture was evaporated to dryness to give Example 33D (140 mg, 0.519 mmol, 93% yield).

Example 33E

N-(1-(4-fluorophenyl)piperidin-4-yl)-3-methoxy-2-oxo-1-(2,2,2-trifluoroethyl)-1,2-dihydropyridine-4-carboxamide

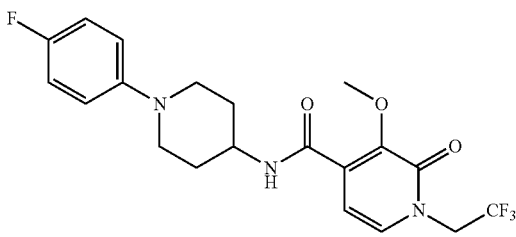 [SMILES: COc1c(C(=O)NC2CCN(c3ccc(F)cc3)CC2)ccn(CC(F)(F)F)c1=O]

To a solution of Example 33D (20 mg, 0.074 mmol) in DCM (1 mL) was added 1-(4-fluorophenyl)piperidin-4-amine (15.85 mg, 0.08200 mmol) and Et$_3$N (0.031 mL, 0.22 mmol). The reaction mixture was stirred at rt for 3 h. The reaction mixture was quenched by addition of brine and the aqueous portion washed with DCM. The combined DCM portions were dried over Na$_2$SO$_4$ and evaporated under reduced pressure to give Example 33E (30 mg, 0.070 mmol, 95% yield).

Example 33

To a solution of Example 33E (31.6 mg, 0.0740 mmol) in DCM (0.5 mL) and DCE (0.5 mL) was added boron trichloride-methyl sulfide complex (80 mg, 0.44 mmol). The reaction mixture was stirred at 70° C. for 3 h. The reaction mixture was quenched by the addition of ice and MeOH. The crude product was purified by prep. HPLC (Column: Phenomenex AXIA Luna 100×20 mm 5 μm; 10 minute gradient from 5 to 100% B; Solvent A: 10% ACN-90% H$_2$O-0.1% TFA; Solvent B: 90% ACN-10% H$_2$O-0.1% TFA). The desired fractions were combined and dried in vacuo to give Example 33 (22 mg, 0.053 mmol, 72% yield). LCMS RT=1.37 min, [M+1]= 414.1 {(MeOH/H$_2$O/TFA) Phenom. Luna C18; 50×4.6 mm; 4 min Grad}; HPLC (150×4.6 mm 3.5 μm, 254 nm): Sunfire {RT=5.03 min, 89%}; Xbridge {RT=5.28 min, 93%}. $^1$H NMR (500 MHz, MeOD) δ ppm 7.37 (2H, dd, J=8.7, 4.3 Hz), 7.12-7.21 (4H, m), 6.70 (1H, d, J=7.4 Hz), 4.78-4.81 (2H, m), 4.20 (1H, ddd, J=10.6, 6.3, 4.3 Hz), 3.63-3.70 (2H, m), 3.35-3.40 (2H, m), 2.23 (2H, d, J=3.0 Hz), 1.91-2.03 (2H, m).

Examples 34-35 were synthesized following the procedure described for Example 33. The analytical data (retention time, mass and conditions of LC-MS) of Example 34-35 are listed in Table 2.

Example 36

3-hydroxy-2-oxo-N-(cis-4-phenylcyclohexyl)-1-(2,2,2-trifluoroethyl)-1,2-dihydropyridine-4-carboxamide

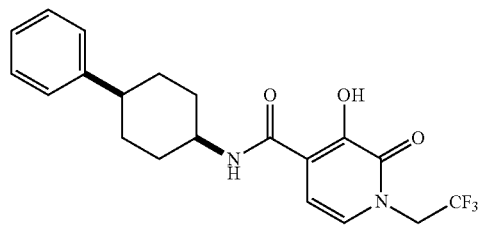 [SMILES: O=C(N[C@H]1CC[C@@H](c2ccccc2)CC1)c1ccn(CC(F)(F)F)c(=O)c1O]

Example 36A 3-hydroxy-2-oxo-N-(cis-4-phenylcyclohexyl)-1,2-dihydropyridine-4-carboxamide

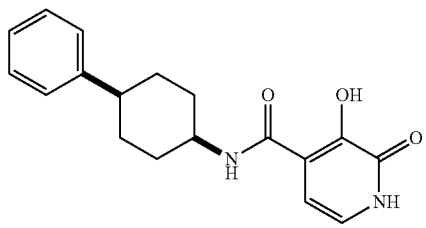 [SMILES: O=C(N[C@H]1CC[C@@H](c2ccccc2)CC1)c1cc[nH]c(=O)c1O]

To a solution of 3-hydroxy-2-oxo-1,2-dihydropyridine-4-carbonyl chloride (Intermediate 17) (38.1 mg, 0.219 mmol) and cis-4-phenylcyclohexanamine (Intermediate 14) (50 mg, 0.29 mmol) in DCM (1 mL) was added Et$_3$N (0.061 mL, 0.44 mmol). The reaction mixture was stirred at rt for 1 h. The reaction mixture was partitioned between H$_2$O and DCM. The DCM layer was dried over Na$_2$SO$_4$ and filtered through a silica gel plug. The solvent was removed under reduced pressure to give Example 36A which was used without further purification.

Example 36B 3-methoxy-2-oxo-N-(cis-4-phenylcyclohexyl)-1,2-dihydropyridine-4-carboxamide

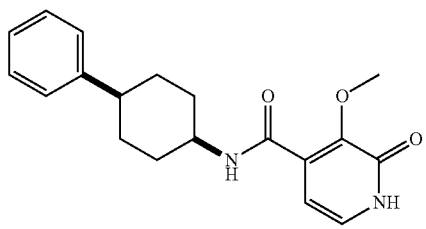 [SMILES: COc1c(C(=O)N[C@H]2CC[C@@H](c3ccccc3)CC2)cc[nH]c1=O]

To a solution of Example 36A (80 mg, 0.26 mmol) in DCM (5 mL) was added (diazomethyl)trimethylsilane (0.128 mL, 0.256 mmol). The reaction mixture was stirred at rt for 16 h. The reaction mixture was evaporated under reduced pressure and dried in vacuo. The residue was purified on ISCO flash chromatography on silica gel using a 4 g column and eluted with 0 to 100% EtOAc in hexane; then 0 to 20% MeOH in DCM to give Example 36B (50 mg, 0.15 mmol, 60% yield).

Example 36C 3-methoxy-2-oxo-N-(cis-4-phenylcyclohexyl)-1-(2,2,2-trifluoroethyl)-1,2-dihydropyridine-4-carboxamide

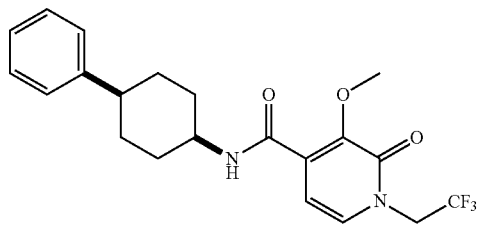 [SMILES: COc1c(C(=O)N[C@H]2CC[C@@H](c3ccccc3)CC2)ccn(CC(F)(F)F)c1=O]

To a solution of Example 36B (20 mg, 0.061 mmol) in DCM (1 mL) was added $Cs_2CO_3$ (39.9 mg, 0.123 mmol). The reaction mixture was stirred for 10 minutes at 60° C. then added 2,2,2-Trifluoroethyl trichloromethanesulfonate (17.25 mg, 0.06100 mmol). The reaction mixture was stirred at rt for 16 h. The reaction mixture was partition between $H_2O$ and DCM and the organic layer was evaporated under reduced pressure. The crude product was chromatographed on silica gel column and eluted with 30% EtOAc in hexane, then 10% MeOH in DCM to give Example 36C (20 mg, 0.049 mmol, 80% yield).

Example 36

To a solution of Example 36C (34 mg, 0.083 mmol) in DCM (0.5 mL) and DCE (0.5 mL) was added boron trichloride-methyl sulfide complex (90 mg, 0.50 mmol). The reaction mixture was stirred at 70° C. for 6 h. The reaction mixture was quenched by the addition of ice and MeOH, purified by prep HPLC using a 10 minutes gradient from 10 to 100% B (Column: Phenomenex AXIA Luna 100×20 mm 5 μm (10 min gradient); Solvent A: 10% ACN-90% $H_2O$-0.1% TFA; Solvent B: 90% ACN-10% $H_2O$-0.1% TFA). Desired fractions were dried in vacuo to give Example 36 (8 mg, 0.020 mmol, 24.37% yield). LCMS=2.1 minutes; [M+1]=395.1 {(MeOH/$H_2O$/TFA) Phenom. Luna C18; 50×4.6 mm; 4 min Grad}; HPLC (150×4.6 mm 3.5 μm, 254 nm): Sunfire {RT=10.4 min, 98%}; Xbridge {RT=9.12 min, 97%}. 1H NMR (500 MHz, MeOD) δ ppm 7.25-7.30 (4H, m), 7.12-7.18 (2H, m), 6.77 (1H, d, J=7.4 Hz), 5.18 (2H, q, J=8.0 Hz), 4.32 (1H, d, J=3.3 Hz), 2.60-2.70 (1H, m), 1.99 (2H, br. s.), 1.73-1.86 (6H, m).

Examples 37-43 were synthesized by following the procedure of Example 36. The HPLC-MS data (retention time, mass and conditions) for Examples 37-43 are listed in Table 2.

Example 44

6-chloro-3-hydroxy-1-methyl-2-oxo-N-(4-phenylcyclohexyl)-1,2-dihydropyridine-4-carboxamide

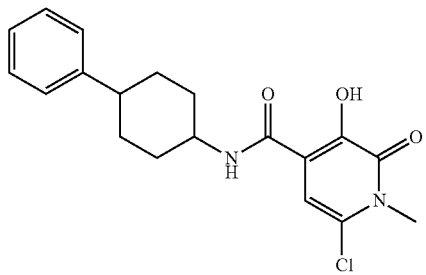 [SMILES: Cn1c(Cl)cc(C(=O)NC2CCC(c3ccccc3)CC2)c(O)c1=O]

Example 44A 3-methoxy-1-methyl-2-oxo-N-(4-phenylcyclohexyl)-1,2-dihydropyridine-4-carboxamide

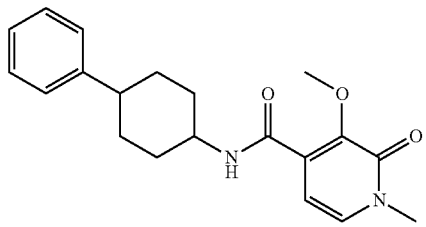 [SMILES: COc1c(C(=O)NC2CCC(c3ccccc3)CC2)ccn(C)c1=O]

Example 44A was synthesized following the procedure described for the synthesis of Example 9B.

Example 44B 6-chloro-3-methoxy-1-methyl-2-oxo-N-(4-phenylcyclohexyl)-1,2-dihydropyridine-4-carboxamide

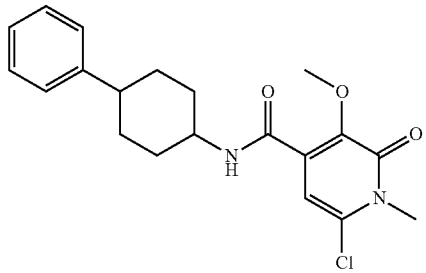 [SMILES: COc1c(C(=O)NC2CCC(c3ccccc3)CC2)cc(Cl)n(C)c1=O]

A solution of Example 44A (20 mg, 0.059 mmol) in DCM (1 mL) was cooled to 0° C. and sulfuryl chloride (4.78 μL, 0.059 mmol) was added. The reaction mixture was stirred at rt for 4 h. The mono-chlorinated product was isolated via preparative HPLC (Column: Phenomenex AXIA Luna 100× 20 mm 5 μm; 0-100% B gradient over 10 min.; Solvent A: 10% ACN-90% H₂O-0.1% TFA; Solvent B: 90% ACN-10% H₂O-0.1% TFA) to give Example 44B (10 mg, 0.027 mmol, 45% yield) as an oil.

Example 44

To a solution of Example 44B (10 mg, 0.027 mmol) in DCM (0.5 mL) and DCE (0.5 mL) was added boron trichloride-methyl sulfide complex (28.7 mg, 0.160 mmol). The reaction mixture was stirred at rt for 16 h. The reaction mixture was quenched by the addition of ice and MeOH. Purification by prep HPLC (Column: Phenomenex AXIA Luna 100×20 mm 5 μm; using a 10 minute gradient from 20 to 100% B; Solvent A: 10% ACN-90% H₂O-0.1% TFA; Solvent B: 90% ACN-10% H₂O-0.1% TFA) provided Example 44 (4 mg, 0.011 mmol, 41.6% yield). LCMS RT=1.82 min, [M+1]= 361 {(MeOH/H₂O/TFA) Phenom. Luna C18; 50×4.6 mm; 4 min Grad}; HPLC (150×4.6 mm 3.5 μm, 254 nm): Sunfire {RT=8.4 min, 90%}; Xbridge {RT=7.8 min, 86%}. $^1$H NMR (500 MHz, MeOD) δ ppm 7.32-7.35 (1H, m), 7.23-7.27 (4H, m), 7.13-7.17 (1H, m), 3.56-3.59 (3H, m), 2.50-2.64 (1H, m), 2.04-2.18 (2H, m), 1.84-1.96 (3H, m), 1.66-1.82 (4H, m).

Examples 45-46 were synthesized by following the procedure in Example 44. The HPLC-MS data (retention time, mass and conditions) for Examples 45-46 are listed in Table 2.

Example 47

(R)—N-(1-(4'-fluorobiphenyl-3-yl)ethyl)-3-hydroxy-1-methyl-2-oxo-1,2-dihydropyridine-4-carboxamide

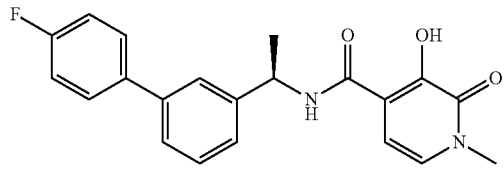 [SMILES: C[C@@H](NC(=O)c1ccn(C)c(=O)c1O)c1cccc(-c2ccc(F)cc2)c1]

Example 47A (R)—N-(1-(4'-fluorobiphenyl-3-yl)ethyl)-3-methoxy-1-methyl-2-oxo-1,2-dihydropyridine-4-carboxamide

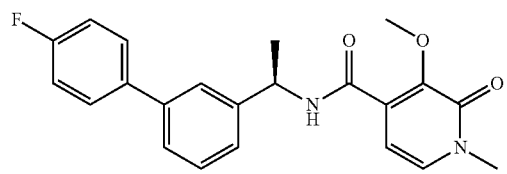 [SMILES: COc1c(C(=O)N[C@H](C)c2cccc(-c3ccc(F)cc3)c2)ccn(C)c1=O]

To a solution of (R)—N-(1-(3-bromophenyl)ethyl)-3-methoxy-1-methyl-2-oxo-1,2-dihydropyridine-4-carboxamide (Intermediate 12) (60 mg, 0.16 mmol) in DME (1.0 mL) was added 4-fluorophenylboronic acid (46.0 mg, 0.329 mmol), sodium carbonate (0.246 mL, 0.493 mmol), and tetrakis(triphenylphosphine)palladium(0) (38.0 mg, 0.0330 mmol) in a microwave vial. The reaction was degassed 3 times under argon and heated at 100° C. overnight. The reaction mixture was diluted with DCM and the organic portion dried over MgSO₄, filtered and concentrated to give Example 47A which was used directly in the next step without further purification.

Example 47

To a solution of Example 47A (62.4 mg, 0.164 mmol) in dichloromethane (0.5 mL) was added boron trichloride (0.492 mL, 0.492 mmol). The reaction mixture was stirred at rt overnight. The reaction mixture was quenched by the addition of MeOH and concentrated under reduced pressure to give a residue which was purified by reverse phase preparative HPLC (5-90% B over 15 min; column: Phenomenex Luna, 5μ, C18, 30×250 mm; A=H₂O/ACN/TFA 90/10/0.1. B=ACN/H₂O/TFA 90/10/0.1) to give Example 47 (32 mg, 0.083 mmol, 50.5% yield) as a white solid. HPLC/MS (Method D) RT=2.02 min, [M+1]$^+$ 367.0; $^1$H NMR (400 MHz, DMSO-d6) δ ppm 8.77 (1H, d, J=7.70 Hz), 7.67-7.73 (2H, m), 7.65 (1H, s), 7.50-7.54 (1H, m), 7.42 (1H, t, J=7.70 Hz), 7.34-7.38 (1H, m), 7.26-7.33 (2H, m), 7.21 (1H, d, J=7.15 Hz), 6.53 (1H, d, J=7.15 Hz), 5.19 (1H, quin, J=7.15 Hz), 3.47 (3H, s), 1.51 (3H, d, J=7.15 Hz).

Example 48 was synthesized from Intermediate 12 and the corresponding boronic acid following the procedure described for Example 47. The HPLC-MS data (retention time, mass and conditions) for Example 48 are listed in Table 2.

TABLE 2

| Ex. # | Structure | Name | RT (min) | [M + 1]$^+$ | LC/MS Methods |
|---|---|---|---|---|---|
| 2 | 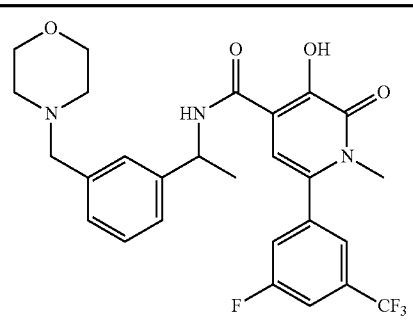 | 6-(3-fluoro-5-(trifluoromethyl)phenyl)-3-hydroxy-1-methyl-N-(1-(3-(morpholinomethyl)phenyl)ethyl)-2-oxo-1,2-dihydropyridine-4-carboxamide | 2.1 | 534.09 | F |

TABLE 2-continued

| Ex. # | Structure | Name | RT (min) | [M + 1]+ | LC/MS Methods |
|---|---|---|---|---|---|
| 3 | 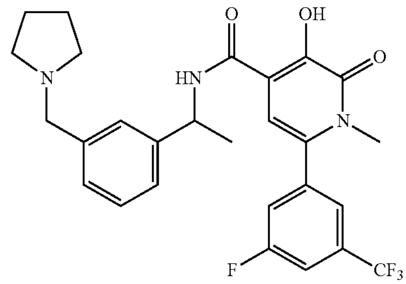 [SMILES: CC(NC(=O)c1cc(-c2cc(F)cc(C(F)(F)F)c2)n(C)c(=O)c1O)c1cccc(CN2CCCC2)c1] | 6-(3-fluoro-5-(trifluoromethyl)phenyl)-3-hydroxy-1-methyl-2-oxo-N-(1-(3-(pyrrolidin-1-ylmethyl)phenyl)ethyl)-1,2-dihydropyridine-4-carboxamide | 1.7 | 518.08 | F |
| 4 | 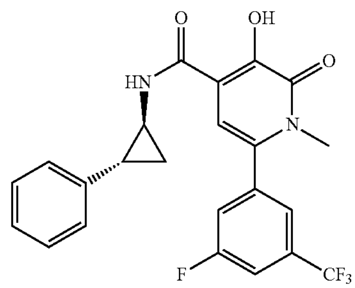 [SMILES: Cn1c(-c2cc(F)cc(C(F)(F)F)c2)cc(C(=O)N[C@H]2C[C@@H]2c2ccccc2)c(O)c1=O] | 6-(3-fluoro-5-(trifluoromethyl)phenyl)-3-hydroxy-1-methyl-2-oxo-N-((1S,2R)-2-phenylcyclopropyl)-1,2-dihydropyridine-4-carboxamide | 2.4 | 446.99 | F |
| 5 | 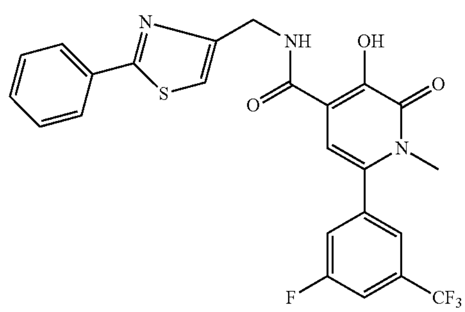 [SMILES: Cn1c(-c2cc(F)cc(C(F)(F)F)c2)cc(C(=O)NCc2csc(-c3ccccc3)n2)c(O)c1=O] | 6-(3-fluoro-5-(trifluoromethyl)phenyl)-3-hydroxy-1-methyl-2-oxo-N-((2-phenylthiazol-4-yl)methyl)-1,2-dihydropyridine-4-carboxamide | 2.4 | 503.97 | F |
| 6 | 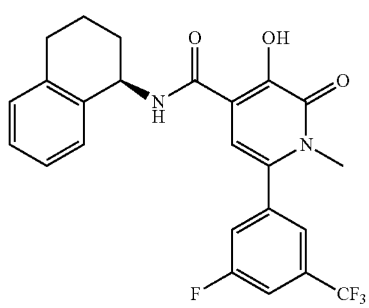 [SMILES: Cn1c(-c2cc(F)cc(C(F)(F)F)c2)cc(C(=O)N[C@@H]2CCCc3ccccc32)c(O)c1=O] | (R)-6-(3-fluoro-5-(trifluoromethyl)phenyl)-3-hydroxy-1-methyl-2-oxo-N-(1,2,3,4-tetrahydronaphthalen-1-yl)-1,2-dihydropyridine-4-carboxamide | 2.1 | 461 | D |
| 7 | 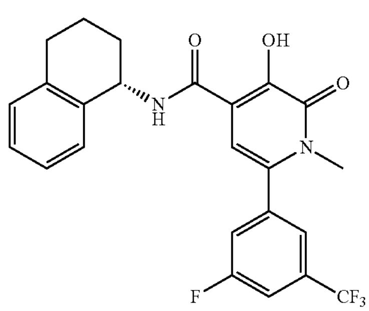 [SMILES: Cn1c(-c2cc(F)cc(C(F)(F)F)c2)cc(C(=O)N[C@H]2CCCc3ccccc32)c(O)c1=O] | (S)-6-(3-fluoro-5-(trifluoromethyl)phenyl)-3-hydroxy-1-methyl-2-oxo-N-(1,2,3,4-tetrahydronaphthalen-1-yl)-1,2-dihydropyridine-4-carboxamide | 2.1 | 461 | D |

TABLE 2-continued

| Ex. # | Structure | Name | RT (min) | [M + 1]+ | LC/MS Methods |
|---|---|---|---|---|---|
| 9 | 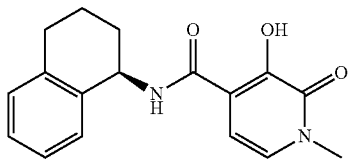 [SMILES: Cn1ccc(C(=O)N[C@@H]2CCCc3ccccc32)c(O)c1=O] | (R)-3-hydroxy-1-methyl-2-oxo-N-(1,2,3,4-tetrahydronaphthalen-1-yl)-1,2-dihydropyridine-4-carboxamide | 1.72 | 299 | D |
| 10 | 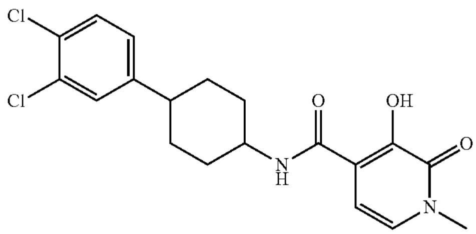 [SMILES: Cn1ccc(C(=O)NC2CCC(c3ccc(Cl)c(Cl)c3)CC2)c(O)c1=O] | N-(4-(3,4-dichlorophenyl)cyclohexyl)-3-hydroxy-1-methyl-2-oxo-1,2-dihydropyridine-4-carboxamide | 2.19 | 395 | D |
| 11 | 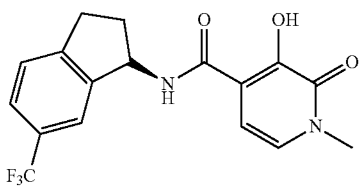 | (R)-3-hydroxy-1-methyl-2-oxo-N-(6-(trifluoromethyl)-2,3-dihydro-1H-inden-1-yl)-1,2-dihydropyridine-4-carboxamide | 2.04 | 353 | D |
| 12 | 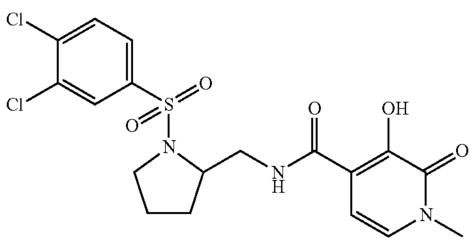 [SMILES: Cn1ccc(C(=O)NCC2CCCN2S(=O)(=O)c2ccc(Cl)c(Cl)c2)c(O)c1=O] | N-((1-(3,4-dichlorophenylsulfonyl)-pyrrolidin-2-yl)methyl)-3-hydroxy-1-methyl-2-oxo-1,2-dihydropyridine-4-carboxamide | 1.81 | 461 | D |
| 13 | 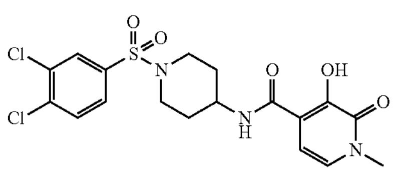 [SMILES: Cn1ccc(C(=O)NC2CCN(S(=O)(=O)c3ccc(Cl)c(Cl)c3)CC2)c(O)c1=O] | N-(1-(3,4-dichlorophenylsulfonyl)-piperidin-4-yl)-3-hydroxy-1-methyl-2-oxo-1,2-dihydropyridine-4-carboxamide | 3.47 | 460 | D |
| 14 | 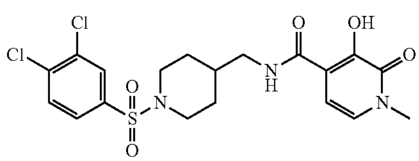 [SMILES: Cn1ccc(C(=O)NCC2CCN(S(=O)(=O)c3ccc(Cl)c(Cl)c3)CC2)c(O)c1=O] | N-((1-(3,4-dichlorophenylsulfonyl)piperidin-4-yl)methyl)-3-hydroxy-1-methyl-2-oxo-1,2-dihydropyridine-4-carboxamide | 3.52 | 461 | D |
| 15 | 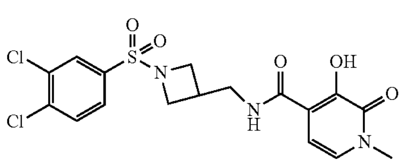 [SMILES: Cn1ccc(C(=O)NCC2CN(S(=O)(=O)c3ccc(Cl)c(Cl)c3)C2)c(O)c1=O] | N-((1-(3,4-dichlorophenylsulfonyl)azetidin-3-yl)methyl)-3-hydroxy-1-methyl-2-oxo-1,2-dihydropyridine-4-carboxamide | 1.59 | 447 | D |
| 17 | 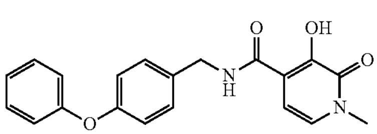 [SMILES: Cn1ccc(C(=O)NCc2ccc(Oc3ccccc3)cc2)c(O)c1=O] | 3-hydroxy-1-methyl-2-oxo-N-(4-phenoxybenzyl)-1,2-dihydropyridine-4-carboxamide | 1.79 | 351.09 | I |

TABLE 2-continued

| Ex. # | Structure | Name | RT (min) | [M + 1]+ | LC/MS Methods |
|---|---|---|---|---|---|
| 18 | 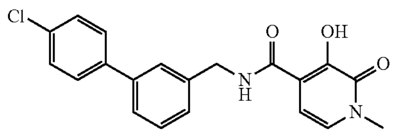 [SMILES: Cn1ccc(C(=O)NCc2cccc(-c3ccc(Cl)cc3)c2)c(O)c1=O] | N-((4'-chlorobiphenyl-3-yl)methyl)-3-hydroxy-1-methyl-2-oxo-1,2-dihydropyridine-4-carboxamide | 2.03 | 369.08 | I |
| 19 | 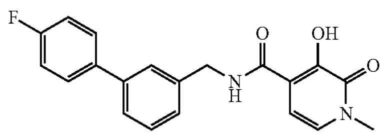 [SMILES: Cn1ccc(C(=O)NCc2cccc(-c3ccc(F)cc3)c2)c(O)c1=O] | N-((4'-fluorobiphenyl-3-yl)methyl)-3-hydroxy-1-methyl-2-oxo-1,2-dihydropyridine-4-carboxamide | 1.81 | 353.04 | I |
| 20 | 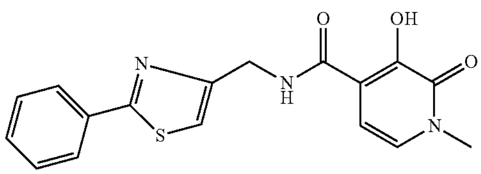 [SMILES: Cn1ccc(C(=O)NCc2csc(-c3ccccc3)n2)c(O)c1=O] | 3-hydroxy-1-methyl-2-oxo-N-((2-phenylthiazol-4-yl)methyl)-1,2-dihydropyridine-4-carboxamide | 1.43 | 342.04 | I |
| 21 | 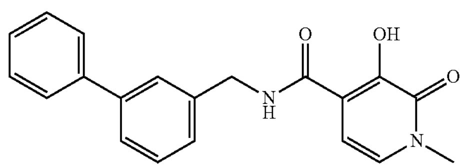 [SMILES: Cn1ccc(C(=O)NCc2cccc(-c3ccccc3)c2)c(O)c1=O] | N-(biphenyl-3-ylmethyl)-3-hydroxy-1-methyl-2-oxo-1,2-dihydropyridine-4-carboxamide | 1.85 | 335.23 | I |
| 22 | 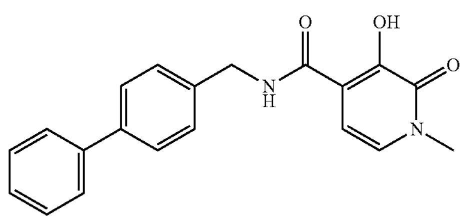 [SMILES: Cn1ccc(C(=O)NCc2ccc(-c3ccccc3)cc2)c(O)c1=O] | N-(biphenyl-4-ylmethyl)-3-hydroxy-1-methyl-2-oxo-1,2-dihydropyridine-4-carboxamide | 1.85 | 335.17 | I |
| 23 | 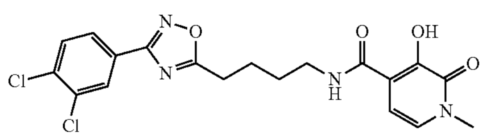 [SMILES: Cn1ccc(C(=O)NCCCCc2nc(-c3ccc(Cl)c(Cl)c3)no2)c(O)c1=O] | N-(4-(3-(3,4-dichlorophenyl)-1,2,4-oxadiazol-5-yl)butyl)-3-hydroxy-1-methyl-2-oxo-1,2-dihydropyridine-4-carboxamide | 3.54 | 437.1 | C |
| 24 | 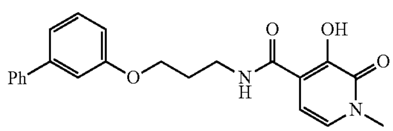 [SMILES: Cn1ccc(C(=O)NCCCOc2cccc(-c3ccccc3)c2)c(O)c1=O] | N-(3-(biphenyl-3-yloxy)propyl)-3-hydroxy-1-methyl-2-oxo-1,2-dihydropyridine-4-carboxamide | 1.99 | 379.12 | F |
| 25 | 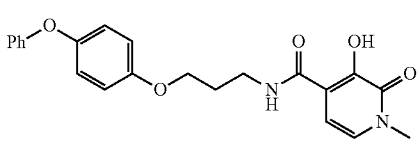 [SMILES: Cn1ccc(C(=O)NCCCOc2ccc(Oc3ccccc3)cc2)c(O)c1=O] | 3-hydroxy-1-methyl-2-oxo-N-(3-(4-phenoxyphenoxy)propyl)-1,2-dihydropyridine-4-carboxamide | 2.00 | 395.09 | F |
| 26 | 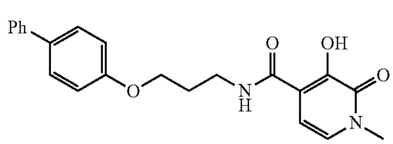 [SMILES: Cn1ccc(C(=O)NCCCOc2ccc(-c3ccccc3)cc2)c(O)c1=O] | N-(3-(biphenyl-4-yloxy)propyl)-3-hydroxy-1-methyl-2-oxo-1,2-dihydropyridine-4-carboxamide | 2.00 | 379.08 | F |
| 27 | 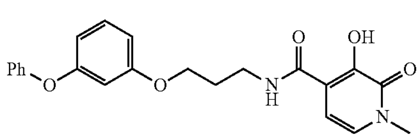 [SMILES: Cn1ccc(C(=O)NCCCOc2cccc(Oc3ccccc3)c2)c(O)c1=O] | 3-hydroxy-1-methyl-2-oxo-N-(3-(3-phenoxyphenoxy)propyl)-1,2-dihydropyridine-4-carboxamide | 2.02 | 395.12 | F |

TABLE 2-continued

| Ex. # | Structure | Name | RT (min) | [M + 1]+ | LC/MS Methods |
|---|---|---|---|---|---|
| 28 | 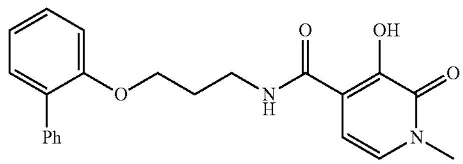 [SMILES: Cn1ccc(C(=O)NCCCOc2ccccc2-c2ccccc2)c(O)c1=O] | N-(3-(biphenyl-2-yloxy)propyl)-3-hydroxy-1-methyl-2-oxo-1,2-dihydropyridine-4-carboxamide | 2.01 | 379.17 | F |
| 29 | 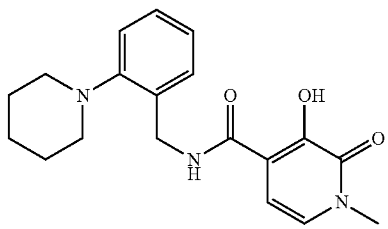 [SMILES: Cn1ccc(C(=O)NCc2ccccc2N2CCCCC2)c(O)c1=O] | 3-hydroxy-1-methyl-2-oxo-N-(2-(piperidin-1-yl)benzyl)-1,2-dihydropyridine-4-carboxamide | 1.97 | 342.21 | I |
| 30 | 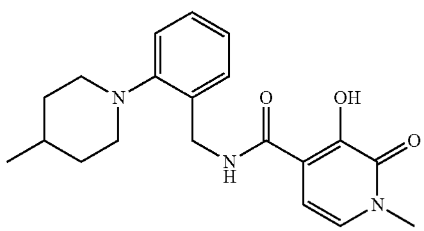 [SMILES: CC1CCN(c2ccccc2CNC(=O)c2ccn(C)c(=O)c2O)CC1] | 3-hydroxy-1-methyl-N-(2-(4-methylpiperidin-1-yl)benzyl)-2-oxo-1,2-dihydropyridine-4-carboxamide | 2.22 | 356.27 | I |
| 31 | 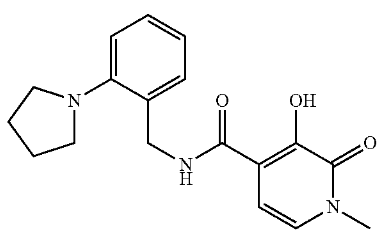 [SMILES: Cn1ccc(C(=O)NCc2ccccc2N2CCCC2)c(O)c1=O] | 3-hydroxy-1-methyl-2-oxo-N-(2-(pyrrolidin-1-yl)benzyl)-1,2-dihydropyridine-4-carboxamide | 1.64 | 328.18 | I |
| 32 | 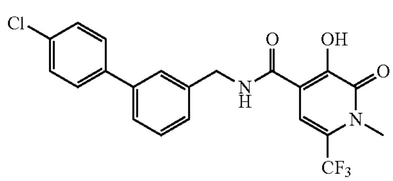 [SMILES: Cn1c(C(F)(F)F)cc(C(=O)NCc2cccc(-c3ccc(Cl)cc3)c2)c(O)c1=O] | N-((4'-chlorobiphenyl-3-yl)methyl)-3-hydroxy-1-methyl-2-oxo-6-(trifluoromethyl)-1,2-dihydropyridine-4-carboxamide | 2.4 | 436.93 | F |
| 34 | 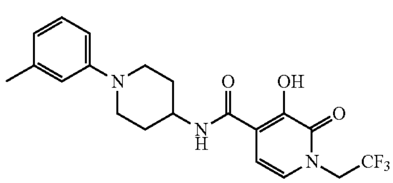 [SMILES: Cc1cccc(N2CCC(NC(=O)c3ccn(CC(F)(F)F)c(=O)c3O)CC2)c1] | 3-hydroxy-2-oxo-N-(1-m-tolylpiperidin-4-yl)-1-(2,2,2-trifluoroethyl)-1,2-dihydropyridine-4-carboxamide | 1.41 | 410 | D |
| 35 | 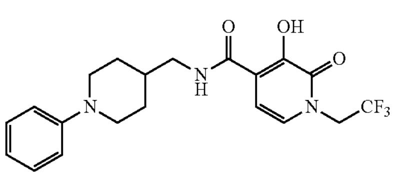 [SMILES: O=C(NCC1CCN(c2ccccc2)CC1)c1ccn(CC(F)(F)F)c(=O)c1O] | 3-hydroxy-2-oxo-N-((1-phenylpiperidin-4-yl)methyl)-1-(2,2,2-trifluoroethyl)-1,2-dihydropyridine-4-carboxamide | 1.43 | 410 | D |

TABLE 2-continued

| Ex. # | Structure | Name | RT (min) | [M + 1]+ | LC/MS Methods |
|---|---|---|---|---|---|
| 37 | 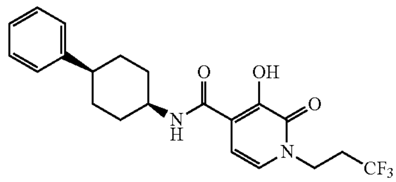 [SMILES: O=C(N[C@H]1CC[C@@H](c2ccccc2)CC1)c1ccn(CCC(F)(F)F)c(=O)c1O] | 3-hydroxy-2-oxo-N-(cis-4-phenylcyclohexyl)-1-(3,3,3-trifluoropropyl)-1,2-dihydropyridine-4-carboxamide | 2.11 | 409 | D |
| 38 | 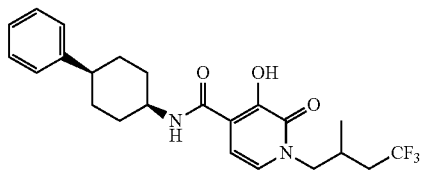 | 3-hydroxy-2-oxo-N-(cis-4-phenylcyclohexyl)-1-(4,4,4-trifluoro-2-methylbutyl)-1,2-dihydropyridine-4-carboxamide | 2.22 | 437 | D |
| 39 | 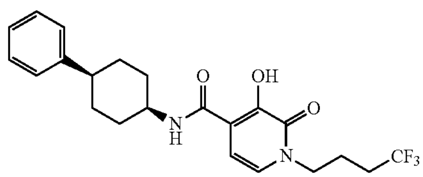 [SMILES: O=C(N[C@H]1CC[C@@H](c2ccccc2)CC1)c1ccn(CCCC(F)(F)F)c(=O)c1O] | 3-hydroxy-2-oxo-N-(cis-4-phenylcyclohexyl)-1-(4,4,4-trifluorobutyl)-1,2-dihydropyridine-4-carboxamide | 3.97 | 423 | C |
| 40 | 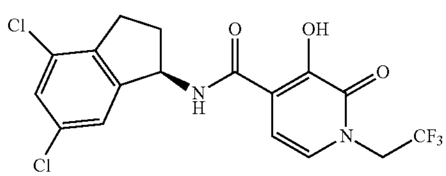 [SMILES: O=C(N[C@@H]1CCc2c(Cl)cc(Cl)cc21)c1ccn(CC(F)(F)F)c(=O)c1O] | (R)-N-(4,6-dichloro-2,3-dihydro-1H-inden-1-yl)-3-hydroxy-2-oxo-1-(2,2,2-trifluoroethyl)-1,2-dihydropyridine-4-carboxamide | 2.16 | 421 | D |
| 41 | 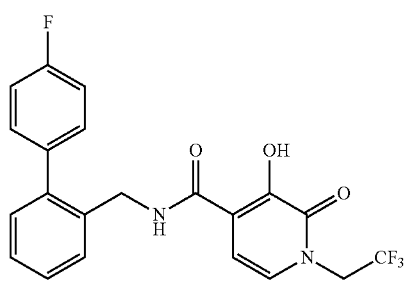 [SMILES: O=C(NCc1ccccc1-c1ccc(F)cc1)c1ccn(CC(F)(F)F)c(=O)c1O] | N-((4'-fluorobiphenyl-2-yl)methyl)-3-hydroxy-2-oxo-1-(2,2,2-trifluoroethyl)-1,2-dihydropyridine-4- | 2.97 | 421 | A |
| 43 | 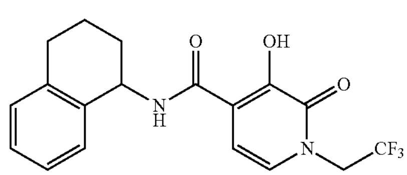 [SMILES: O=C(NC1CCCc2ccccc21)c1ccn(CC(F)(F)F)c(=O)c1O] | 3-hydroxy-2-oxo-N-(1,2,3,4-tetrahydronaphthalen-1-yl)-1-(2,2,2-trifluoroethyl)-1,2-dihydropyridine-4-carboxamide | 2.75 | 367 | D |
| 45 | 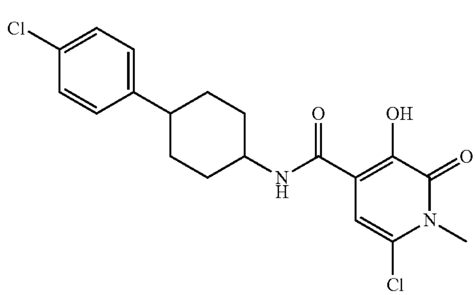 | 6-chloro-N-(4-(4-chlorophenyl)cyclohexyl)-3-hydroxy-1-methyl-2-oxo-1,2-dihydropyridine-4-carboxamide | 2.00 | 395 | D |

Isomer A

TABLE 2-continued

| Ex. # | Structure | Name | RT (min) | [M + 1]+ | LC/MS Methods |
|---|---|---|---|---|---|
| 46 | ![structure] Isomer B | 6-chloro-N-(4-(4-chlorophenyl)cyclohexyl)-3-hydroxy-1-methyl-2-oxo-1,2-dihydropyridine-4-carboxamide | 1.99 | 395 | D |
| 48 | ![structure] | (R)-N-(1-(biphenyl-3-yl)ethyl)-3-hydroxy-1-methyl-2-oxo-1,2-dihydropyridine-4-carboxamide | 1.98 | 349.0 | D |

Example 49

(R)-3-hydroxy-1-methyl-2-oxo-N-(1-(3-(2-(trifluoromethyl)phenylamino)phenyl)ethyl)-1,2-dihydropyridine-4-carboxamide

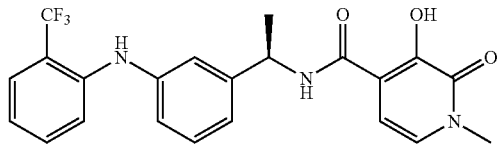 [SMILES: C[C@@H](NC(=O)c1ccn(C)c(=O)c1O)c1cccc(Nc2ccccc2C(F)(F)F)c1]

Example 49A (R)-3-methoxy-1-methyl-2-oxo-N-(1-(3-(2-(trifluoromethyl)phenylamino)phenyl)ethyl)-1,2-dihydropyridine-4-carboxamide

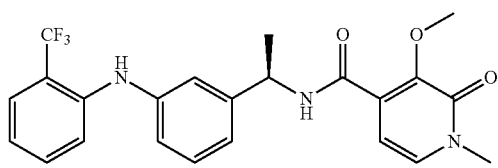 [SMILES: COc1c(C(=O)N[C@H](C)c2cccc(Nc3ccccc3C(F)(F)F)c2)ccn(C)c1=O]

A mixture of 2-(trifluoromethyl)aniline (26.5 mg, 0.164 mmol), (R)—N-(1-(3-bromophenyl)ethyl)-3-methoxy-1-methyl-2-oxo-1,2-dihydropyridine-4-carboxamide (Intermediate 12) (60 mg, 0.16 mmol), $Pd_2(dba)_3$ (30.1 mg, 0.0330 mmol), BINAP (30.7 mg, 0.0490 mmol), and sodium tert-butoxide (22.10 mg, 0.2300 mmol) in toluene (0.8 mL) was degassed twice under argon. The reaction mixture was refluxed at 110° C. overnight then filtered and the residue washed with DCM (2 mL×2). The organic solution was concentrated under reduced pressure and purified by ISCO flash chromatography on a 12 g silica gel cartridge which was eluted with a 12 min gradient from 0-10% MeOH/DCM to give Example 49A (73.1 mg, 100%) which used without further purification. HPLC/MS (Method D) RT=2.10 min, [M+1]+ 446.0.

Example 49

To a solution of Example 49A (73.1 mg, 0.164 mmol) in DCM (1 mL) was added boron trichloride (0.492 mL, 0.492 mmol). The reaction was stirred at room temperature overnight. The reaction mixture was quenched by the addition of MeOH and concentrated under reduced pressure. The crude product was purified by Prep (ACN/water/TFA), 10-90% B over 15 min (column: Phenomenex Luna, 5μ, C18, 30×250 mm, A=$H_2O$/ACN/TFA 90/10/0.1. B=ACN/$H_2O$/TFA 90/10/0.1). Example 46 was collected (at RT=10.02 min) and concentrated to give Example 49 (8 mg, 0.02 mmol, 10% yield) as a white solid. HPLC/MS (Method D) RT=1.65 min, [M+1]+ 432.2; $^1$H NMR (400 MHz, ACETONE-d6) δ ppm 7.62 (1H, d, J=7.70 Hz), 7.45 (1H, t, J=7.70 Hz), 7.36-7.42 (1H, m), 7.22-7.30 (2H, m), 7.12 (1H, d, J=7.15 Hz), 7.05 (3H, d, J=6.05 Hz), 6.63 (1H, d, J=7.15 Hz), 5.17-5.27 (1H, m), 3.55 (3H, s), 1.55 (3H, d, J=7.15 Hz).

Example 50

N-(9H-fluoren-9-yl)-3-hydroxy-1-methyl-2-oxo-1,2-dihydropyridine-4-carboxamide

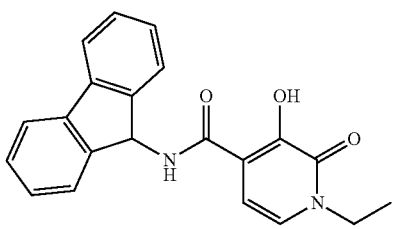 [SMILES: CCn1ccc(C(=O)NC2c3ccccc3-c3ccccc32)c(O)c1=O]

Example 50A 3-ethoxy-1-ethyl-N-(9H-fluoren-9-yl)-2-oxo-1,2-dihydropyridine-4-carboxamide

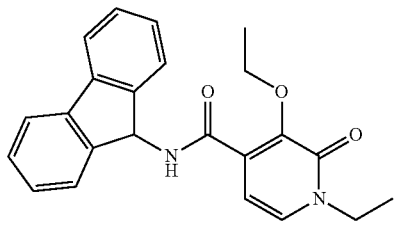 [SMILES: CCOc1c(C(=O)NC2c3ccccc3-c3ccccc32)ccn(CC)c1=O]

To a solution of Intermediate 7 (24 mg, 0.12 mmol) and HOBt (20.5 mg, 0.134 mmol) in DCM (1 mL) was added EDC (35.0 mg, 0.183 mmol), followed by 9H-fluoren-9-amine (24.26 mg, 0.1340 mmol) and N-methylmorpholine (0.040 mL, 0.37 mmol). The reaction mixture was stirred at rt for 72 h. The reaction mixture was quenched by the addition of brine and DCM. The organic layer was separated and dried over $Na_2SO_4$ and dried in vacuo. The crude product was purified by a short silica gel column eluted with 30% EtOAc in hexane to give Example 50A (35 mg, 0.093 mmol, 77% yield).

Example 50

To a solution of Example 50A (20 mg, 0.053 mmol) in DCM (2 mL) was added boron trichloride-methyl sulfide complex (9.58 mg, 0.0530 mmol). The reaction mixture was stirred at 70° C. for 16 h. The reaction mixture was quenched by the addition of ice and MeOH and was purified via prep HPLC (Column: Phenomenex AXIA Luna 100×20 mm 5 µm; using a 10 minute gradient from 10 to 100%; Solvent A: 10% ACN-90% $H_2O$-0.1% TFA, Solvent B: 90% ACN-10% $H_2O$-0.1% TFA). The desired fractions were dried in vacuo to give Example 50 (11 mg, 0.032 mmol, 60% yield). LCMS=1.98 minutes [M+1]=347.1 {(MeOH/$H_2O$/TFA) Phenom. Luna C18; 50×4.6 mm; 4 min Grad}; HPLC (150×4.6 mm 3.5 µm, 254 nm): Sunfire {RT=9.24 min, 92%}; Xbridge {RT=8.3 min, 89%}. $^1$H NMR (400 MHz, MeOD) δ ppm 1.34 (t, J=7.07 Hz, 3H) 4.04 (q, J=7.07 Hz, 2H) 6.32 (s, 1H) 6.77 (d, J=7.33 Hz, 1H) 7.14 (d, J=7.33 Hz, 1H) 7.31 (s, 2H) 7.34 (d, J=7.33 Hz, 2H) 7.43 (t, J=7.45 Hz, 2H) 7.59 (d, J=7.33 Hz, 2H) 7.79 (d, J=7.58 Hz, 2H).

Example 51

1-(cyclopropylmethyl)-3-hydroxy-2-oxo-N-(cis-4-phenylcyclohexyl)-1,2-dihydropyridine-4-carboxamide

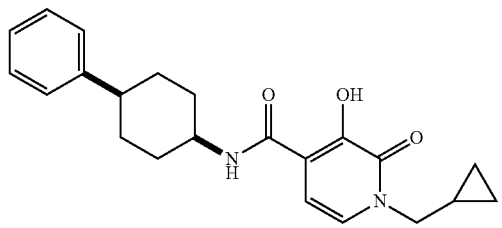

To a solution of 1-(cyclopropylmethyl)-3-hydroxy-2-oxo-1,2-dihydropyridine-4-carboxylic acid (Intermediate 11), (30 mg, 0.14 mmol), (1s,4s)-4-phenylcyclohexanamine (Intermediate 14) (30.2 mg, 0.172 mmol) and PyBOP (74.6 mg, 0.143 mmol) in DMF (1 mL) were treated with DIEA (0.075 mL, 0.43 mmol). The reaction mixture was then stirred at rt for 2 h. The reaction mixture was diluted with DCM, washed with 1N HCl, water and brine, dried over $MgSO_4$, filtered and concentrated in vacuo to give the crude product which was purified by ISCO flash chromatography (4 g silica gel cartridge, 0 to 100% EtOAc/Hex over 15 min gradient) to afford Example 51 (12.2 mg, 0.0330 mmol, 23.2% yield). LCMS RT=2.2 min; [M+1]=367 {(MeOH/$H_2O$/TFA) Phenom. Luna C18; 50×4.6 mm; 4 min Grad}; HPLC (150×4.6 mm 3.5 µm, 254 nm): Sunfire {RT=10.4 min, 99.5%}; Xbridge {RT=9.09 min, 96.3%}. $^1$H NMR (500 MHz, MeOD) δ ppm 0.42-0.46 (m, 1H) 0.56-0.60 (m, 1H) 1.28-1.34 (m, 1H) 1.75-1.82 (m, 6H) 2.00 (d, J=12.10 Hz, 2H) 2.52 (q, J=7.15 Hz, 1H) 2.62-2.68 (m, 1H) 3.88 (d, J=7.15 Hz, 1H) 4.08 (t, J=7.02 Hz, 1H) 4.32 (d, J=2.75 Hz, 1H) 5.03-5.09 (m, 1H) 6.75 (dd, J=14.17, 7.29 Hz, 1H) 7.10-7.13 (m, 1H) 7.10-7.22 (m, 2H) 7.16 (td, J=5.50, 3.30 Hz, 1H) 7.26-7.29 (m, 4H).

Example 52

N-((4'-fluorobiphenyl-3-yl)methyl)-3-hydroxy-1-isobutyl-2-oxo-1,2-dihydropyridine-4-carboxamide

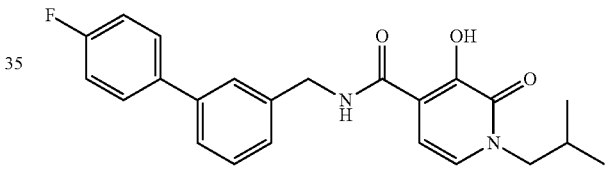

Example 52A 3-isobutoxy-1-isobutyl-2-oxo-1,2-dihydropyridine-4-carbonyl chloride

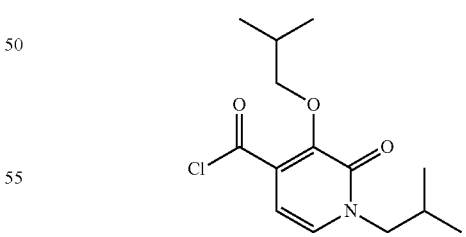

To a solution of ethyl 3-isobutoxy-1-isobutyl-2-oxo-1,2-dihydropyridine-4-carboxylate (Intermediate 8) (100 mg, 0.339 mmol) was added thionyl chloride (24.71 µL, 0.3390 mmol). The reaction mixture was stirred at 80° C. for 3 h. The solvent was evaporated under reduced pressure to give Example 52A which was used without further purification (90 mg, 0.315 mmol, 93% yield). LCMS RT=1.89 min [M+MeO+1]=282 {(MeOH/$H_2O$/TFA) Phenom. Luna C18; 50×4.6 mm; 4 min Grad}.

Example 52B

N-((4'-fluorobiphenyl-3-yl)methyl)-3-isobutoxy-1-isobutyl-2-oxo-1,2-dihydropyridine-4-carboxamide

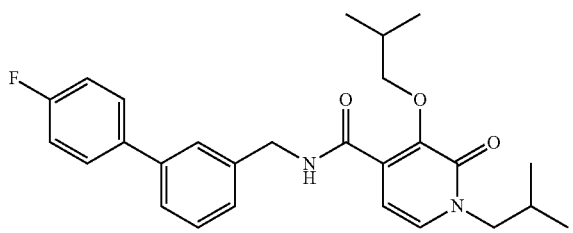 [SMILES: CC(C)COc1c(C(=O)NCc2cccc(-c3ccc(F)cc3)c2)ccn(CC(C)C)c1=O]

To a solution of Example 52A (30 mg, 0.11 mmol) in DCM (1 mL) was added (4'-fluorobiphenyl-3-yl)methanamine (19.21 mg, 0.09500 mmol) and Et$_3$N (0.020 mL, 0.14 mmol). The reaction was stirred at rt for 30 min. The reaction mixture was quenched by the addition of brine and extracted into DCM. The combined organic portions were dried over Na$_2$SO$_4$. The filtrate was evaporated under reduced pressure to give Example 52B (32 mg, 0.071 mmol, 74% yield). LCMS RT=2.25 min [M+1]=451 {(MeOH/H$_2$O/TFA) Phenom. Luna C18; 50×4.6 mm; 4 min Grad}.

Example 52

To a solution of Example 52B (31.5 mg, 0.0700 mmol) was added boron tri-chloride-methyl sulfide complex (75 mg, 0.42 mmol). The reaction mixture was stirred at 70° C. for 2 h. The reaction mixture was cooled and quenched by the addition of ice and MeOH. The reaction mixture was evaporated under reduced pressure and the crude product was purified by Prep HPLC (Column: Phenomenex AXIA Luna 100× 20 mm 5 μm; using a 10 min gradient for 10 to 100% B; Solvent A: 10% ACN-90% H$_2$O-0.1% TFA; Solvent B: 90% ACN-10% H$_2$O-0.1% TFA to give Example 52 (22 mg, 0.056 mmol, 80% yield). LCMS RT=2.10 min, [M+1]=395. {(MeOH/H$_2$O/TFA) Phenom. Luna C18; 50×4.6 mm; 4 min Grad}; HPLC (150×4.6 mm 3.5 μm, 254 nm): Sunfire {RT=10.4 min, 92.3%}; Xbridge {RT=9.3 min, 93.7%}. $^1$H NMR (400 MHz, chloroform-D) δ ppm 8.19 (1H, br. s.), 7.51-7.58 (3H, m), 7.46-7.49 (1H, m), 7.42 (1H, t, J=7.6 Hz), 7.34 (1H, d, J=7.3 Hz), 7.13 (2H, t, J=8.7 Hz), 6.92-6.96 (1H, m), 6.86-6.89 (1H, m), 4.74 (2H, d, J=5.6 Hz), 3.82 (2H, d, J=7.6 Hz), 2.14-2.25 (1H, m), 0.96 (6H, d, J=6.8 Hz).

What is claimed is:

1. A compound of Formula (I):

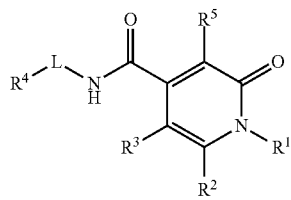

or a stereoisomer, a tautomer, or a pharmaceutically acceptable salt thereof, wherein:

R$^1$ is selected from the group consisting of: H, C$_{1-6}$ alkyl substituted with 0-3 R$^a$, C$_{2-6}$ alkenyl substituted with 0-3 R$^a$, and —(CH$_2$)$_n$—W—(CH$_2$)$_m$—R$^{1a}$;

W is selected from the group consisting of: a bond, NH, O, S, N(C$_{1-4}$ alkyl), CO, CONH, CON(C$_{1-4}$ alkyl), NHCO, SO$_2$, NHSO$_2$, SO$_2$NH, NHCO$_2$, and CHR;

R$^{1a}$ is selected from the group consisting of: C$_{3-10}$ carbocycle and a 5- to 10-membered heterocycle comprising: carbon atoms and 1-4 heteroatoms selected from N, NR$^e$, O, and S(O)$_p$; and wherein said carbocycle and heterocycle are substituted with 0-3 R$^c$;

R$^2$ and R$^3$ are, independently at each occurrence, selected from the group consisting of: H, halogen, CF$_3$, OCF$_3$, C$_{1-6}$ alkyl substituted with 0-3 R$^a$, C$_{2-6}$ alkenyl substituted with 0-3 R$^a$, —CO$_2$(C$_{1-4}$ alkyl), —SO$_2$(phenyl), —(CH$_2$)$_n$—(C$_{3-6}$ cycloalkyl substituted with 0-3 R$^c$), —(CH$_2$)$_n$-(phenyl substituted with 0-3 R$^b$), —(CH$_2$)$_n$-(naphthyl substituted with 0-3 R$^b$), and —(CH$_2$)$_n$-(5- to 10 membered heterocycle comprising: carbon atoms and 1-4 heteroatoms selected from N, NR$^e$, O, and S(O)$_p$), wherein said heterocycle is substituted with 0-3 R$^c$;

R$^4$ is selected from the group consisting of: C$_{3-10}$ carbocycle and a 5- to 10-membered heterocycle comprising: carbon atoms and 1-4 heteroatoms selected from N, NR$^e$, O, and S(O)$_p$; wherein said carbocycle and heterocycle are substituted with 0-3 R$^d$;

R$^5$ is selected from the group consisting of: OR$^6$, CN, and NR$^7$R$^8$;

R$^6$ is selected from the group consisting of: H and C$_{1-6}$ alkyl substituted with 0-1 CO$_2$H;

R$^7$ is selected from the group consisting of: H, C$_{1-6}$ alkyl substituted with 0-1 R$^a$, —(CH$_2$)$_n$-(phenyl substituted with 0-3 R$^b$), and —(CH$_2$)$_n$-(5- to 6-membered heterocycle comprising: carbon atoms and 1-4 heteroatoms selected from N, NR$^e$, O, and S(O)$_p$); and wherein said heterocycle is substituted with 0-3 R$^c$;

R$^8$ is selected from the group consisting of: H and C$_{1-6}$ alkyl;

alternatively, NR$^7$R$^8$ is a 5- to 6-membered heterocycle comprising: carbon atoms and 1-4 heteroatoms selected from N, NR$^e$, O, and S(O)$_p$;

L is X$_1$—Y—X$_2$;

X$_1$, and X$_2$ are, independently at each occurrence, selected from the group consisting of: a bond, a hydrocarbon linker and a hydrocarbon-heteroatom linker; wherein said hydrocarbon linker and hydrocarbon-heteroatom linker may be substituted with 0-2 R$^g$; said hydrocarbon linker has one to five carbon atoms and may be saturated or unsaturated; and said hydrocarbon-heteroatom linker may be saturated or unsaturated and has zero to four carbon atoms and one group selected from O, —CO—, S, —SO—, —SO$_2$—, NH, and N(C$_{1-4}$ alkyl);

Y is selected from the group consisting of: C$_{3-10}$ carbocycle and a 4- to 10 membered heterocycle comprising: carbon atoms and 1-4 heteroatoms selected from N, NR$^e$, O, and S(O)$_p$; wherein each said carbocycle and heterocycle may be optionally substituted with one, two or three substituents independently selected from: halogen, OH, C$_{1-4}$ alkyl, C$_{1-4}$ haloalkyl, and C$_{1-4}$ alkyoxy;

alternatively, R⁴-L- is

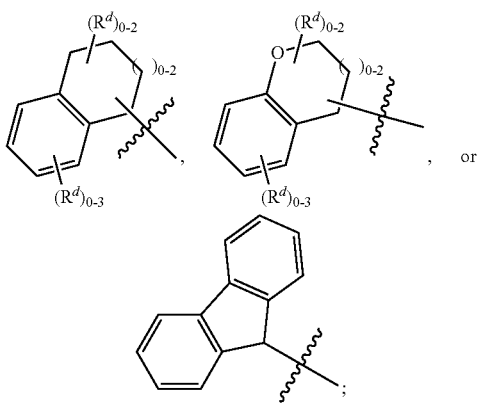

$R^a$ is, independently at each occurrence, selected from the group consisting of: halogen, OH, $C_{1-4}$ alkyl, $C_{1-4}$ alkoxy, $C_{1-4}$ haloalkyl, $C_{1-4}$ haloalkoxy, $CF_3$, $OCF_3$, CN, $NH_2$, $NO_2$, $NH(C_{1-4}$ alkyl), $N(C_{1-4}$ alkyl)$_2$, $CO_2H$, $CO_2(C_{1-4}$ alkyl), $NHCO(C_{1-4}$ alkyl substituted with 0-1 $NH_2$), $N(C_{1-4}$ alkyl)$CO(C_{1-4}$ alkyl), $NHCO_2(C_{1-4}$ alkyl), $CONHSO_2(C_{1-4}$ alkyl), $SO_2(C_{1-4}$ alkyl), $CONH_2$, $CONH(C_{1-4}$ alkyl), $NHSO_2(C_{1-4}$ alkyl), $N(C_{1-4}$ alkyl)$SO_2(C_{1-4}$ alkyl), and phenoxy;

$R^b$ is, independently at each occurrence, selected from the group consisting of: halogen, OH, $C_{1-4}$ alkyl, $C_{1-4}$ alkoxy, $C_{1-4}$ haloalkyl, $C_{1-4}$ haloalkoxy, $CF_3$, $OCF_3$, $OCF_2CHF_2$, $OCH_2CF_3$, CN, $NH_2$, $NO_2$, $NH(C_{1-4}$ alkyl), $N(C_{1-4}$ alkyl)$_2$, $CO_2H$, $CO_2(C_{1-4}$ alkyl), $CONH_2$, $CONH(C_{1-4}$ alkyl), $CON(C_{1-4}$ alkyl)$_2$, $NHCO_2(C_{1-4}$ alkyl), $NHSO_2(C_{1-4}$ alkyl), $N(C_{1-4}$ alkyl)$SO_2(C_{1-4}$ alkyl), $SO_2(C_{1-4}$ alkyl), $SO_2NH_2$, phenyl, benzyl, and phenoxy;

$R^c$ is, independently at each occurrence, selected from the group consisting of: =O and $R^b$;

$R^d$ is, independently at each occurrence, selected from the group consisting of: =O, halogen, OH, $C_{1-6}$ alkyl substituted with 0-1 OH, $C_{1-4}$ alkoxy, $C_{1-4}$ haloalkyl, $C_{1-4}$ haloalkoxy, $CF_3$, $OCF_3$, $OCF_2CF_2H$, $OCH_2CF_3$, CN, $NH_2$, $NO_2$, $NH(C_{1-4}$ alkyl), $N(C_{1-4}$ alkyl)$_2$, $CO_2H$, $CO_2(C_{1-4}$ alkyl), $CO(C_{1-4}$ alkyl), $NHCO(C_{1-4}$ alkyl), —$CH_2NHCO(C_{1-4}$ alkyl), $CONH_2$, $CONH(C_{1-4}$ alkyl), $CON(C_{1-4}$ alkyl)$_2$, $SO_2(C_{1-4}$ alkyl), $SO_2NH_2$, —$SO_2NH(C_{1-4}$ alkyl), —$SO_2NH(C_{3-6}$ cycloalkyl), —$NHSO_2(C_{1-4}$ alkyl), —$CH_2NHSO_2(C_{1-4}$ alkyl), $Si(C_{1-4}$ alkyl)$_3$, and phenyl optionally substituted with one or two substituents independently selected from: halogen, OH, $C_{1-4}$ alkyl, $C_{1-4}$ haloalkyl, $C_{1-4}$ alkyoxy, and $NHCO(C_{1-4}$ alkyl);

$R^e$ is, independently at each occurrence, selected from the group consisting of: H, $C_{1-4}$ alkyl, $CO(C_{1-4}$ alkyl), $CO_2(C_{1-4}$ alkyl), $CO_2$(benzyl), and —$(CH_2)_n$-(phenyl optionally substituted with 0-2 halogens);

$R^f$ is, independently at each occurrence, selected from the group consisting of: $C_{1-4}$ alkyl, $C_{2-4}$ alkenyl, $CO_2(C_{1-4}$ alkyl), $CONH_2$, $C_{3-6}$ cycloalkyl, phenyl, and benzyl;

$R^g$ is, independently at each occurrence, selected from the group consisting of: halogen, OH, $C_{1-4}$ alkyl, $C_{2-4}$ alkenyl, $C_{1-4}$ haloalkyl, $C_{1-4}$ alkyoxy, $CO_2(C_{1-4}$ alkyl), $C_{3-6}$ cycloalkyl, and phenyl;

m, at each occurrence, is selected from 0, 1, and 2;
n, at each occurrence, is selected from 0, 1, 2, 3, and 4; and
p, at each occurrence, is selected from 0, 1, and 2.

2. A compound according to claim 1, wherein:
$R^1$ is selected from the group consisting of: $C_{1-6}$ alkyl substituted with 0-2 $R^a$, $C_{2-6}$ alkenyl substituted with 0-2 $R^a$, and —$(CH_2)_n$—W—$R^{1a}$;

W is selected from the group consisting of: a bond, NH, $N(C_{1-4}$ alkyl), CO, CONH, $CON(C_{1-4}$ alkyl), $SO_2$, $NHCO_2$, and CHR;

$R^{1a}$ is selected from the group consisting of: $C_{3-6}$ cycloalkyl substituted with 0-3 $R^c$, phenyl substituted with 0-3 $R^b$, naphthyl substituted with 0-2 $R^b$, tetrahydronaphthyl substituted with 0-2 $R^b$, dihydroindenyl substituted with 0-2 $R^c$, and a 5- to 10-membered heterocycle comprising: carbon atoms and 1-4 heteroatoms selected from N, $NR^e$, O, and $S(O)_p$; and wherein said heterocycle is substituted with 0-3 $R^c$;

$R^2$ is selected from the group consisting of: H, halogen, $CF_3$, $OCF_3$, $C_{1-6}$ alkyl substituted with 0-2 $R^a$, $C_{2-6}$ alkenyl substituted with 0-2 $R^a$, —$CO_2(C_{1-4}$ alkyl), —$SO_2$(phenyl), —$(CH_2)_n$—$(C_{3-6}$ cycloalkyl substituted with 0-3 $R^c$), —$(CH_2)_n$-(phenyl substituted with 0-3 $R^b$), —$(CH_2)_n$-(naphthyl substituted with 0-3 $R^b$), and —$(CH_2)_n$-(5- to 10 membered heterocycle comprising: carbon atoms and 1-4 heteroatoms selected from N, $NR^e$, O, and $S(O)_p$), wherein said heterocycle is substituted with 0-3 $R^c$;

$R^3$ is selected from the group consisting of: H, halogen, $CF_3$, $OCF_3$, $C_{1-6}$ alkyl substituted with 0-2 $R^a$, and phenyl substituted with 0-2 $R^b$;

$R^4$ is selected from the group consisting of: $C_{5-6}$ cycloalkyl, phenyl, naphthyl, tetrahydronaphthyl, dihydroindenyl, and a 5- to 10-membered heterocycle comprising: carbon atoms and 1-4 heteroatoms selected from N, $NR^e$, O, and $S(O)_p$; and wherein each moiety is substituted with 0-3 $R^d$;

$R^5$ is selected from the group consisting of: OH, $O(C_{1-4}$ alkyl substituted with 0-1 $CO_2H$), CN, and $NR^7R^8$;

L is $X_1$—Y—$X_2$;

$X_1$ and $X_2$ are, independently at each occurrence, selected from the group consisting of: a bond, a hydrocarbon linker and a hydrocarbon-heteroatom linker; wherein said hydrocarbon linker and hydrocarbon-heteroatom linker may be substituted with 0-1 $R^g$; said hydrocarbon linker may be saturated or unsaturated and has one to five carbon atoms; and said hydrocarbon-heteroatom linker may be saturated or unsaturated and has zero to four carbon atoms and one group selected from O, —CO—, S, —SO—, —$SO_2$—, NH, and $N(C_{1-4}$ alkyl);

Y is selected from the group consisting of: $C_{3-7}$ carbocycle and a 4- to 10-membered heterocycle comprising: carbon atoms and 1-4 heteroatoms selected from N, $NR^e$, O, and $S(O)_p$; wherein each said carbocycle and heterocycle may be optionally substituted with one, two or three substituents independently selected from: halogen, OH, $C_{1-4}$ alkyl, $C_{1-4}$ haloalkyl, and $C_{1-4}$ alkyoxy;

alternatively, $R^4$-L- is

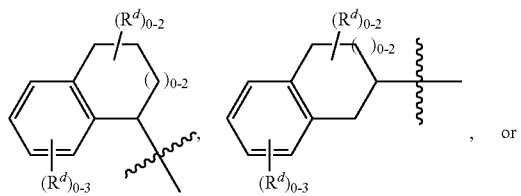

-continued

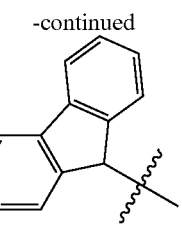

and n, at each occurrence, is selected from 0, 1, 2, and 3.

3. A compound according to claim 2, wherein:

$R^1$ is selected from the group consisting of: $C_{1-6}$ alkyl substituted with 0-2 $R^a$, $C_{2-6}$ alkenyl substituted with 0-2 $R^a$, and $-(CH_2)_n-W-R^{1a}$;

W is selected from the group consisting of: a bond, CO, CONH, CON($C_{1-4}$ alkyl), $SO_2$, and $CHR^f$;

$R^1a$ is selected from the group consisting of: $C_{3-6}$ cycloalkyl substituted with 0-3 $R^c$, phenyl substituted with 0-3 $R^b$, and a 5- to 6-membered heterocycle comprising: carbon atoms and 1-4 heteroatoms selected from N, $NR^e$, O, and $S(O)_p$; and wherein said heterocycle is substituted with 0-3 $R^c$;

$R^5$ is selected from the group consisting of: OH and $C_{1-6}$ alkoxy;

L is $X_1-Y-X_2$;

$X_1$ is selected from the group consisting of: a bond, a hydrocarbon linker and a hydrocarbon-heteroatom linker; wherein said hydrocarbon linker and hydrocarbon-heteroatom linker may be substituted with 0-1 $R^g$; said hydrocarbon linker has one to four carbon atoms and may be saturated or unsaturated; and said hydrocarbon-heteroatom linker may be saturated or unsaturated and has zero to three carbon atoms and one group selected from O, —CO—, S, —SO—, —$SO_2$—, NH, and N($C_{1-4}$ alkyl);

$X_2$ is selected from the group consisting of: a bond, a hydrocarbon linker and a hydrocarbon-heteroatom linker; wherein said hydrocarbon linker and hydrocarbon-heteroatom linker may be substituted with 0-1 $R^g$; said hydrocarbon linker has one to five carbon atoms and may be saturated or unsaturated; and said hydrocarbon-heteroatom linker may be saturated or unsaturated and has zero to four carbon atoms and one group selected from O, —CO—, S, —SO—, —$SO_2$—, NH, and N($C_{1-4}$ alkyl); and Y is, independently at each occurrence, selected from the group consisting of: $C_{3-6}$ cycloalkylene, phenylene, azetidinylene, pyrrolidinylene, piperidinylene, thiazolylene, and oxadiazolylene; wherein said phenylene may be optionally substituted with one or two substituents independently selected from: halogen, OH, $C_{1-4}$ alkyl, $C_{1-4}$ haloalkyl, and $C_{1-4}$ alkyoxy;

alternatively, $R^4$-L- is

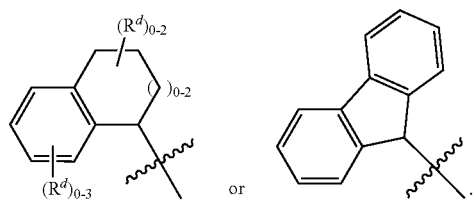

4. A compound according to claim 3, wherein:

$R^1$ is selected from the group consisting of: H, $C_{1-4}$ alkyl substituted with 0-1 $CF_3$, —$CH_2CO_2$($C_{1-4}$ alkyl), cyclopropyl, cyclopropylmethyl, phenyl, 4-$CF_3$-phenyl, 3-halo-4-$CO_2$($C_{1-4}$ alkyl)-phenyl, 2-($C_{1-4}$ alkoxy)-5-halo-phenyl, benzyl, 4-$CO_2$H-benzyl, 4-$CO_2$($C_{1-4}$ alkyl)-benzyl, 4-$SO_2$($C_{1-4}$ alkyl)-benzyl, 2-halo-phenethyl, 4-halo-phenethyl, 2-OH-phenethyl, —$SO_2$(phenyl), and pyrid-4-yl;

$R^2$ is selected from the group consisting of: H, halogen, $CF_3$, $OCF_3$, $C_{1-4}$ alkyl, $C_{2-4}$ alkenyl, —$SO_2$(phenyl), phenyl substituted with 0-2 $R^c$, naphthyl substituted with 0-2 $R^c$, and a heterocycle selected from: thienyl, oxadiazolyl, pyridyl, indolyl, quinolinyl, and isoquinolinyl; wherein said heterocycle is substituted with 0-2 $R^c$;

$R^3$ is selected from the group consisting of: H, $C_{1-4}$ alkyl and phenyl substituted with 0-2 $R^c$;

$R^4$ is selected from the group consisting of: phenyl substituted with 0-3 $R^d$, naphthyl, pyrrolidinyl, piperidinyl, morpholinyl,

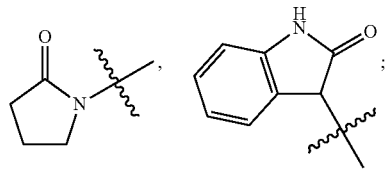 [SMILES: *N1CCCC1=O ; *C1C(=O)Nc2ccccc21]

L is selected from the group consisting of: —$(CH_2)_{0-2}$-phenylene-$C_{1-4}$ alkylene-, -phenylene-O—$C_{1-3}$ alkylene-, —O-phenylene-$C_{1-3}$ alkylene-, —O-phenylene-O—$C_{1-3}$ alkylene-, —S-phenylene-$C_{1-3}$ alkylene-, —NH-phenylene-$C_{1-3}$ alkylene-,

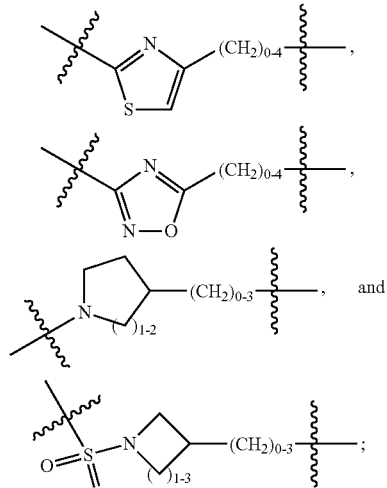

wherein each said alkylene may be straight or branched; and said phenylene may be optionally substituted with one or two substituents independently selected from: halogen, OH, $C_{1-4}$ alkyl, $C_{1-4}$ haloalkyl, and $C_{1-4}$ alkyoxy;

$R^d$ is, independently at each occurrence, selected from the group consisting of: halogen, $C_{1-6}$ alkyl, $C_{1-4}$ alkoxy, $C_{1-4}$ haloalkyl, $CF_3$, $OCF_3$, $CO_2$($C_{1-4}$ alkyl), $NO_2$, and phenyl optionally substituted with one or two substituents independently selected from: halogen, OH, $C_{1-4}$ alkyl, $C_{1-4}$ haloalkyl, and $C_{1-4}$ alkyoxy; and alternatively, R⁴-L- is

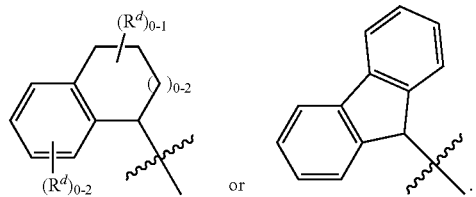

5. A compound according to claim 4, wherein the compound is of Formula (II):

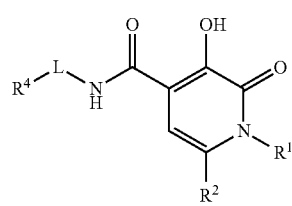

or a stereoisomer, a tautomer, or a pharmaceutically acceptable salt thereof, wherein:

R¹ is selected from the group consisting of: H, $C_{1-4}$ alkyl substituted with 0-1 $CF_3$, —$CH_2CO_2(C_{1-4}$ alkyl), cyclopropyl, cyclopropylmethyl, phenyl, 4-$CF_3$-phenyl, 3-halo-4-$CO_2(C_{1-4}$ alkyl)-phenyl, benzyl, 2-halo-benzyl, 4-$CO_2$H-benzyl, 4-$CO_2(C_{1-4}$ alkyl)-benzyl, 4-$SO_2$($C_{1-4}$ alkyl)-benzyl, 2-halo-phenethyl, 4-halo-phenethyl, 2-OH-phenethyl, and pyrid-4-yl;

R² is selected from the group consisting of: H, halogen, $C_{1-4}$ alkyl, $C_{2-4}$ alkenyl, $CF_3$, phenyl, 3-halo-phenyl, 4-halo-phenyl, 3-$C_{1-4}$ alkyl-phenyl, 3-$CF_3$-phenyl, 4-$CF_3$-phenyl, 3-$OCF_3$-phenyl, 4-$OCF_3$-phenyl, 4-OH-phenyl, 4-CN-phenyl, 3-$NH_2$-phenyl, 3-$N(C_{1-4}$ alkyl)$_2$-phenyl, 3-$CO_2$H-phenyl, 3-$CONH_2$-phenyl, 4-$CONH_2$-phenyl, 3-$CON(C_{1-4}$ alkyl)$_2$-phenyl, 4-$CON(C_{1-4}$ alkyl)$_2$-phenyl, 3-$NHSO_2(C_{1-4}$ alkyl)-phenyl, 4-$NHSO_2(C_{1-4}$ alkyl)-phenyl, 4-$SO_2(C_{1-4}$ alkyl)-phenyl, 3-$SO_2NH_2$-phenyl, 3-biphenyl, 4-biphenyl, 3-halo-4-halo-phenyl, 3-halo-5-halo-phenyl, 3-$C_{1-4}$ alkyl-4-halo-phenyl, 3-$CF_3$-5-halo-phenyl, 3-$CF_3$-4-halo-phenyl, 3-halo-4-$CF_3$-phenyl, 3-$CF_3$-4-OH-phenyl, 3,5-di$CF_3$-phenyl, 3-$OCF_2CHF_2$-5-halo-phenyl, 1-naphthyl, 2-naphthyl, thien-2-yl, thien-3-yl, 5-($C_{1-4}$ alkyl)-1,2,4-oxadiazol-3-yl, pyrid-4-yl, 1-$C_{1-4}$ alkyl-indol-5-yl, 3-quinolinyl, 5-quinolinyl, 6-quinolinyl, and 5-isoquinolinyl;

R⁴ is selected from the group consisting of: phenyl, 2-($C_{1-4}$ alkyl)-phenyl, 3-($C_{1-4}$ alkyl)-phenyl, 4-($C_{1-4}$ alkyl)-phenyl, 2-($C_{1-4}$ alkoxy)-phenyl, 3-($C_{1-4}$ alkoxy)-phenyl, 4-($C_{1-4}$ alkoxy)-phenyl, 2-halo-phenyl, 3-halo-phenyl, 4-halo-phenyl, 2-$CF_3$-phenyl, 3-$CF_3$-phenyl, 4-$CF_3$-phenyl, 3-$OCF_3$-phenyl, 4-$OCF_3$-phenyl, 3-$CO_2(C_{1-4}$ alkyl)-phenyl, 4-$CO_2(C_{1-4}$ alkyl)-phenyl, 2-$NO_2$-phenyl, 3-$NO_2$-phenyl, 4-$NO_2$-phenyl, 3-halo-4-halo-phenyl, 3-halo-5-halo-phenyl, 2-halo-6-halo-phenyl, 1-naphthyl, 2-naphthyl, pyrrolidin-1-yl, and morpholin-4-yl;

L is selected from the group consisting of: -(1,2-phenylene)-$C_{1-3}$ alkylene-, -(1,3-phenylene)-$C_{1-3}$ alkylene-, -(1,2-phenylene)-O—$C_{1-3}$ alkylene-, -(1,3-phenylene)-O—$C_{1-3}$ alkylene-, -(1,4-phenylene)-O—$C_{1-3}$ alkylene-, —O-(1,4-phenylene)-$C_{1-3}$ alkylene-, —O-(1,3-phenylene)-O—$C_{1-3}$ alkylene-, —O-(1,4-phenylene)-O—$C_{1-3}$ alkylene-, —NH-(1,3-phenylene)-$C_{1-3}$ alkylene-,

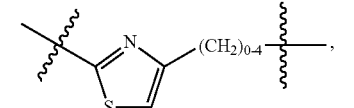

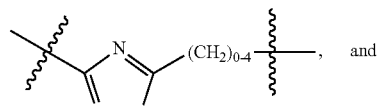

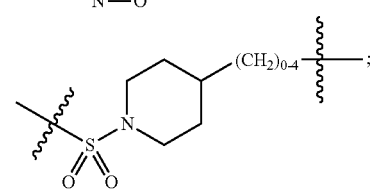

wherein each said alkylene may be straight or branched; and alternatively, R⁴-L- is

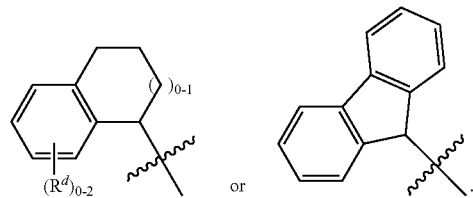

6. A compound according to claim 5, wherein:

R¹ is selected from the group consisting of: $C_{1-4}$ alkyl substituted with 0-1 $CF_3$, and cyclopropylmethyl;

R² is selected from the group consisting of: H, halogen, $CF_3$, and 3-$CF_3$-5-halo-phenyl;

R⁴ is selected from the group consisting of: phenyl, 4-halo-phenyl, 2-$CF_3$-phenyl, 3-halo-4-halo-phenyl, pyrrolidin-1-yl, and morpholin-4-yl;

L is selected from the group consisting of: 1,4-cyclohexylene, -(1,2-phenylene)-$CH_2$—, -(1,3-phenylene)-$CH_2$—, -(1,3-phenylene)-CH($C_{1-4}$ alkyl)-, -(1,2-phenylene)-O($CH_2$)$_3$—, -(1,3-phenylene)-O($CH_2$)$_3$—, -(1,4-phenylene)-O($CH_2$)$_3$—, —O-(1,4-phenylene)-$CH_2$—, —O-(1,3-phenylene)-O($CH_2$)$_3$—, —O-(1,4-phenylene)-O($CH_2$)$_3$—, —NH-(1,3-phenylene)-$CH_2$—,

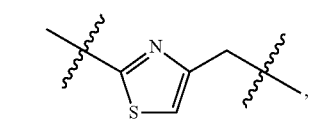

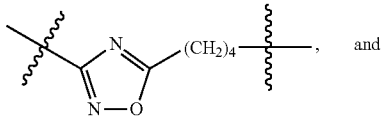

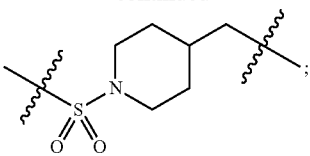

and
alternatively, $R^4$-L- is

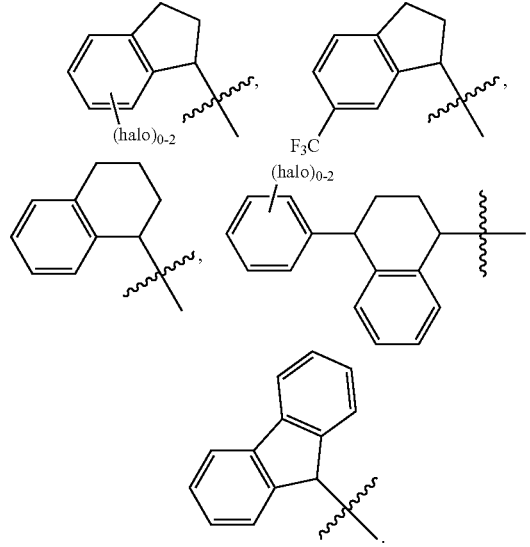

7. A compound according to claim 6, wherein:
$R^1$ is selected from the group consisting of: methyl, isobutyl, $CH_2CF_3$, $CH_2CH_2CF_3$, and cyclopropylmethyl;
$R^2$ is selected from the group consisting of: H, Cl, $CF_3$, and 3-$CF_3$-5-F-phenyl;
$R^4$ is selected from the group consisting of: phenyl, 4-F-phenyl, 4-Cl-phenyl, 2-$CF_3$-phenyl, 3,4-diCl-phenyl, pyrrolidin-1-yl, and morpholin-4-yl; and
L is selected from the group consisting of: 1,4-cyclohexylene, -(1,2-phenylene)-$CH_2$—, -(1,3-phenylene)-$CH_2$—, -(1,3-phenylene)-$CH(CH_3)$—, -(1,2-phenylene)-$O(CH_2)_3$—, -(1,3-phenylene)-$O(CH_2)_3$—, -(1,4-phenylene)-$O(CH_2)_3$—, —O-(1,4-phenylene)-$CH_2$—, —O-(1,3-phenylene)-$O(CH_2)_3$—, —O-(1,4-phenylene)-$O(CH_2)_3$—, —NH-(1,3-phenylene)-$CH_2$—,

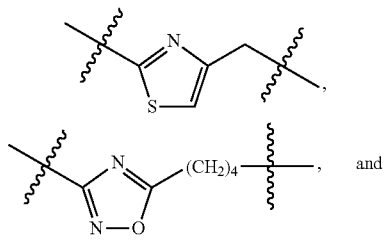

and
alternatively, $R^4$-L- is

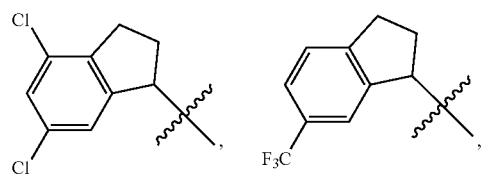

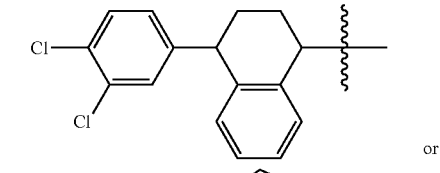

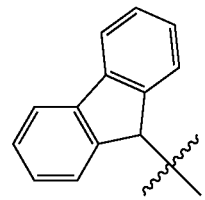

8. A compound according to claim 7, wherein:
$R^1$, $R^2$, $R^4$ and L are selected in concert from the group consisting of:

| $R^1$ | $R^2$ | $R^4$ | L |
| --- | --- | --- | --- |
| $CH_3$ | Cl | 4-Cl—Ph | 1,4-cyclohexylene |
| $CH_3$ | 3-$CF_3$-5-F—Ph | Ph | 1,4-cyclohexylene |

-continued

| R¹ | R² | R⁴ | L |
|---|---|---|---|
| CH₃ | H | 3,4-diCl—Ph | piperidine-N-SO₂ linker |
| CH₂CF₃ | H | Ph | cyclohexyl |
| CH₂CH₂CF₃ | H | Ph | cyclohexyl |
| CH₂-cyclopropyl | H | Ph | cyclohexyl |
| CH₃ | Cl | Ph | cyclohexyl |
| CH₃ | H | 4-F—Ph | -O-(1,4-phenylene)-CH₂- |
| CH₂CF₃ | H | 4-F—Ph | 1,2-phenylene-CH₂ |
| CH₃ | CF₃ | 4-Cl—Ph | 1,3-phenylene |
| CH₃ | H | Ph | 1,3-phenylene-CH₂ |
| CH₃ | H | Ph | -O-(1,3-phenylene)-O-(CH₂)₃- |
| i-Bu | H | 4-F—Ph | 1,3-phenylene-CH₂ |

-continued
| R¹ | R² | R⁴ | L |
|---|---|---|---|
| CH₃ | H | Ph | 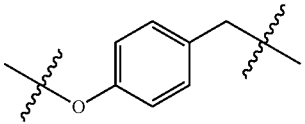 [SMILES: *Cc1ccc(O*)cc1] |
| CH₃ | H | Ph | 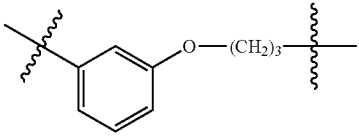 |
| CH₃ | H | 4-F—Ph | 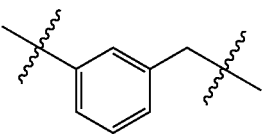 [SMILES: *Cc1cccc(*)c1] |
| CH₃ | H | Ph | 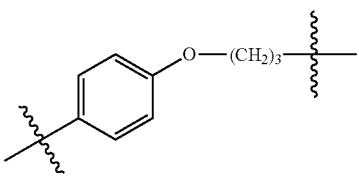 |
| CH₃ | H | Ph | 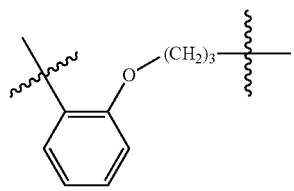 |
| CH₃ | H | Ph | 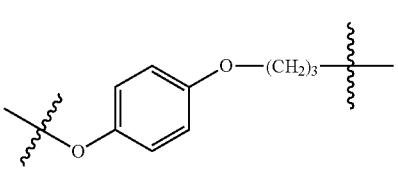 |
| CH₃ | H | 4-F—Ph | 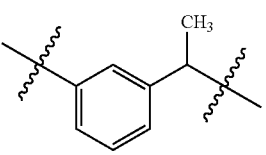 [SMILES: *c1cccc(C(*)C)c1] |
| CH₃ | H | Ph | 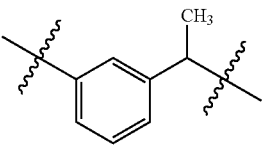 [SMILES: *c1cccc(C(*)C)c1] |
| CH₃ | H | 4-Cl—Ph | 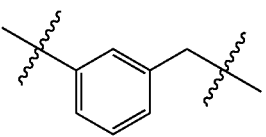 [SMILES: *Cc1cccc(*)c1] |

-continued

| R¹ | R² | R⁴ | L |
|---|---|---|---|
| CH₃ | H | Ph | (1,4-phenylene)-CH₂ |
| CH₃ | H | 2-CF₃—Ph | NH-(1,3-phenylene)-CH₂ |
| CH₃ | H | morpholin-4-yl | (1,3-phenylene)-CH(CH₃) |
| CH₃ | H | pyrrolidin-1-yl | (1,3-phenylene)-CH(CH₃) |
| CH₃ | H | 3,4-diCl—Ph | 1,2,4-oxadiazole-(CH₂)₄ |
| CH₃ | 3-CF₃-5-F—Ph | Ph | thiazole |

9. A compound according to claim 7, wherein:
  R¹ is selected from the group consisting of: methyl, isobutyl, and CH₂CF₃;
  R² is selected from the group consisting of: H, Cl, CF₃, and 3-CF₃-5-F-phenyl;
  R⁴ is selected from the group consisting of: phenyl, 4-F-phenyl, 4-Cl-phenyl, and 3,4-diCl-phenyl;
  L is selected from the group consisting of: 1,4-cyclohexylene, -(1,2-phenylene)-CH₂—, -(1,3-phenylene)-CH₂—, -(1,3-phenylene)-CH(CH₃)—, -(1,2-phenylene)-O(CH₂)₃—, -(1,3-phenylene)-O(CH₂)₃—, -(1,4-phenylene)-O(CH₂)₃—, —O-(1,4-phenylene)-CH₂—, —O-(1,3-phenylene)-O(CH₂)₃—, —O-(1,4-phenylene)-O(CH₂)₃—,

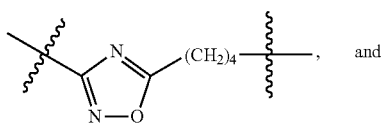

and

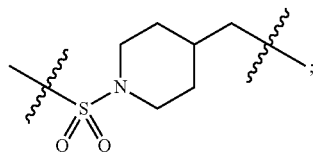

and alternatively, R⁴-L- is

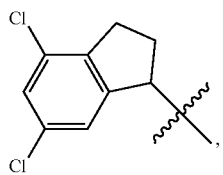, 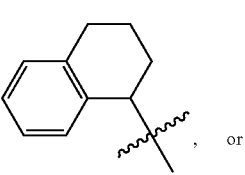, or

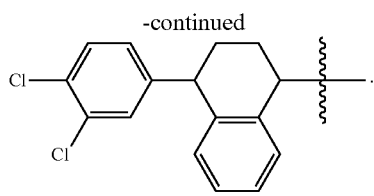

10. A compound according to claim 9, wherein:

R² is selected from the group consisting of: H, Cl, CF₃, and 3-CF₃-5-F-phenyl;

R⁴ is selected from the group consisting of: phenyl, 4-F-phenyl, 4-Cl-phenyl, and 3,4-diCl-phenyl;

L is selected from the group consisting of: 1,4-cyclohexylene, -(1,2-phenylene)-CH₂—, -(1,3-phenylene)-CH₂—, -(1,2-phenylene)-O(CH₂)₃—, -(1,3-phenylene)-O(CH₂)₃—, -(1,4-phenylene)-O(CH₂)₃—, —O-(1,4-phenylene)-CH₂—, —O-(1,3-phenylene)-O(CH₂)₃—, and

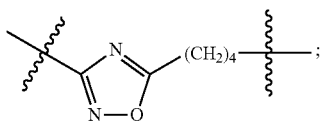

and alternatively, R⁴-L- is

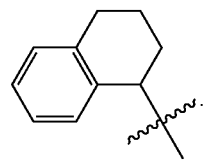 [SMILES: *C1CCCc2ccccc21]

11. A compound according to claim 1, wherein the compound is selected from the exemplified examples, or a stereoisomer, a tautomer, or a pharmaceutically acceptable salt thereof.

12. A pharmaceutical composition, comprising: a pharmaceutically acceptable carrier and a compound of claim 1.

13. A pharmaceutical composition, comprising: a pharmaceutically acceptable carrier and a compound of claim 5.

14. A pharmaceutical composition, comprising: a pharmaceutically acceptable carrier and a compound of claim 8.

\* \* \* \* \*